(12) United States Patent
Tegg

(10) Patent No.: US 8,556,850 B2
(45) Date of Patent: Oct. 15, 2013

(54) SHAFT AND HANDLE FOR A CATHETER WITH INDEPENDENTLY-DEFLECTABLE SEGMENTS

(75) Inventor: Troy T. Tegg, Elk River, MN (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 0 days.

(21) Appl. No.: 13/406,152

(22) Filed: Feb. 27, 2012

(65) Prior Publication Data

US 2012/0203169 A1  Aug. 9, 2012

Related U.S. Application Data

(63) Continuation-in-part of application No. 12/347,100, filed on Dec. 31, 2008, now Pat. No. 8,123,721, and a continuation-in-part of application No. 13/105,646, filed on May 11, 2011.

(60) Provisional application No. 61/333,641, filed on May 11, 2010.

(51) Int. Cl.
*A61M 25/092* (2006.01)

(52) U.S. Cl.
USPC ............................................. 604/95.04

(58) Field of Classification Search
USPC ............................................. 604/95.04
See application file for complete search history.

(56) References Cited

U.S. PATENT DOCUMENTS

| | | | |
|---|---|---|---|
| 4,924,092 A | 5/1990 | Crist, Jr. | |
| 5,108,368 A | 4/1992 | Hammerslag et al. | |
| 5,125,895 A | 6/1992 | Buchbinder et al. | |
| 5,125,896 A | 6/1992 | Hojeibane | |
| 5,170,803 A | 12/1992 | Hewson et al. | |
| 5,195,968 A | 3/1993 | Lundquist et al. | |
| 5,203,772 A | 4/1993 | Hammerslag et al. | |
| 5,254,088 A | 10/1993 | Lundquist et al. | |
| 5,273,535 A | 12/1993 | Edwards et al. | |
| 5,318,525 A | 6/1994 | West et al. | |
| 5,325,845 A | 7/1994 | Adair | |
| 5,342,299 A | 8/1994 | Snoke et al. | |
| 5,354,297 A | 10/1994 | Avitall | |
| 5,383,852 A | 1/1995 | Stevens-Wright | |
| 5,415,633 A * | 5/1995 | Lazarus et al. | 604/95.05 |
| 5,487,757 A | 1/1996 | Truckai et al. | |
| 5,531,721 A * | 7/1996 | Pepin et al. | 604/525 |
| 5,549,542 A | 8/1996 | Kovalcheck | |

(Continued)

FOREIGN PATENT DOCUMENTS

EP  0431206  7/1995

*Primary Examiner* — Aarti B Berdichevsky
(74) *Attorney, Agent, or Firm* — Dykema Gossett PLLC

(57) ABSTRACT

An elongate medical device with independently-deflectable segments and a handle for manually deflecting those segments can include a shaft having a distal segment and proximal segment, at least one proximal segment deflection wire adapted to deflect the proximal segment, at least one distal segment deflection wire adapted to deflect the distal segment independent of the proximal segment, and a handle portion. The handle portion may comprise a first manual actuation mechanism coupled to the at least one distal segment deflection wire and a second manual actuation mechanism coupled to the at least one proximal segment deflection wire. Actuation of the first manual actuation mechanism may impart a tensile force on the distal segment deflection wire to cause the distal segment to deflect, and actuation of the second manual actuation mechanism may impart a tensile force on the proximal segment to cause the proximal segment to deflect.

13 Claims, 35 Drawing Sheets

(56) References Cited

U.S. PATENT DOCUMENTS

| | | |
|---|---|---|
| 5,662,606 A | 9/1997 | Cimino et al. |
| 5,702,433 A | 12/1997 | Taylor et al. |
| 5,715,817 A | 2/1998 | Stevens-Wright et al. |
| 5,842,984 A | 12/1998 | Avitall |
| 5,853,409 A | 12/1998 | Swanson et al. |
| 5,860,974 A | 1/1999 | Abele |
| 5,861,024 A | 1/1999 | Rashidi |
| 5,876,340 A | 3/1999 | Tu et al. |
| 5,891,138 A | 4/1999 | Tu et al. |
| 5,897,554 A | 4/1999 | Chia et al. |
| 5,921,924 A | 7/1999 | Avitall |
| 5,931,577 A | 8/1999 | Ishibashi |
| 5,944,690 A | 8/1999 | Falwell et al. |
| 6,066,125 A | 5/2000 | Webster, Jr. |
| 6,071,274 A | 6/2000 | Thompson et al. |
| 6,071,279 A | 6/2000 | Whayne et al. |
| 6,076,012 A | 6/2000 | Swanson et al. |
| 6,211,936 B1 | 4/2001 | Nakamura |
| 6,233,476 B1 | 5/2001 | Strommer et al. |
| 6,241,727 B1 | 6/2001 | Tu et al. |
| 6,308,091 B1 | 10/2001 | Avitall |
| 6,330,473 B1 | 12/2001 | Swanson et al. |
| 6,402,746 B1 | 6/2002 | Whayne et al. |
| 6,430,426 B2 | 8/2002 | Avitall |
| 6,454,758 B1 | 9/2002 | Thompson et al. |
| 6,497,667 B1 | 12/2002 | Miller et al. |
| 6,582,536 B2 | 6/2003 | Shimada |
| 6,690,963 B2 | 2/2004 | Ben-Haim et al. |
| 6,942,661 B2 | 9/2005 | Swanson |
| 7,130,700 B2 | 10/2006 | Gardeski et al. |
| 7,197,354 B2 | 3/2007 | Sobe |
| 7,263,397 B2 | 8/2007 | Hauck et al. |
| D550,356 S | 9/2007 | Anderson et al. |
| 7,386,339 B2 | 6/2008 | Strommer et al. |
| 7,507,229 B2 * | 3/2009 | Hewitt et al. ............... 604/527 |
| 7,715,204 B2 | 5/2010 | Miller |
| 7,785,252 B2 * | 8/2010 | Danitz et al. ............... 600/142 |
| 7,848,789 B2 | 12/2010 | Govari et al. |
| 7,901,358 B2 | 3/2011 | Mehi et al. |
| 8,123,721 B2 * | 2/2012 | Tegg ........................ 604/95.04 |
| 2002/0077590 A1 | 6/2002 | Ponzi et al. |
| 2002/0087166 A1 | 7/2002 | Brock et al. |
| 2002/0087169 A1 | 7/2002 | Brock et al. |
| 2004/0153049 A1 | 8/2004 | Hewitt et al. |
| 2005/0038467 A1 | 2/2005 | Hebert et al. |
| 2005/0107737 A1 | 5/2005 | McDaniel |
| 2005/0267461 A1 | 12/2005 | Cao et al. |
| 2008/0234660 A2 | 9/2008 | Cumming et al. |
| 2008/0312536 A1 | 12/2008 | Dala-Krishna |
| 2009/0105640 A1 | 4/2009 | Bednarek et al. |
| 2009/0264817 A1 * | 10/2009 | Flach et al. ............... 604/95.04 |
| 2010/0004592 A1 | 1/2010 | Butler |
| 2010/0130924 A1 * | 5/2010 | Martin et al. ............. 604/95.04 |
| 2010/0262075 A1 * | 10/2010 | Danitz et al. ............. 604/95.04 |
| 2010/0280449 A1 * | 11/2010 | Alvarez et al. ............ 604/95.04 |
| 2011/0264074 A1 | 10/2011 | Tegg et al. |
| 2011/0282176 A1 * | 11/2011 | Tegg ........................ 600/374 |
| 2012/0029334 A1 | 2/2012 | Tegg |

* cited by examiner

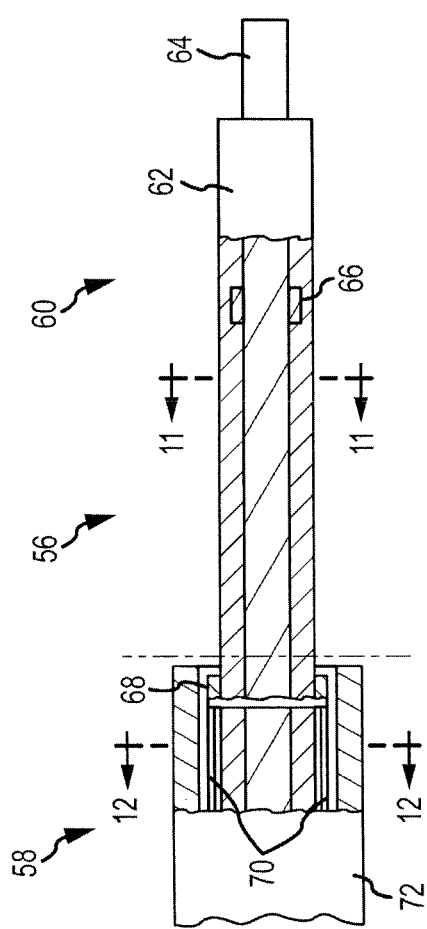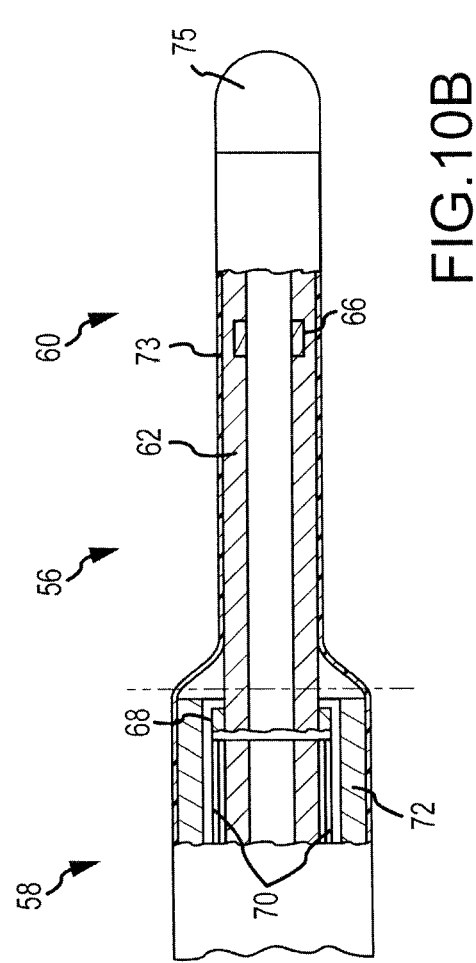

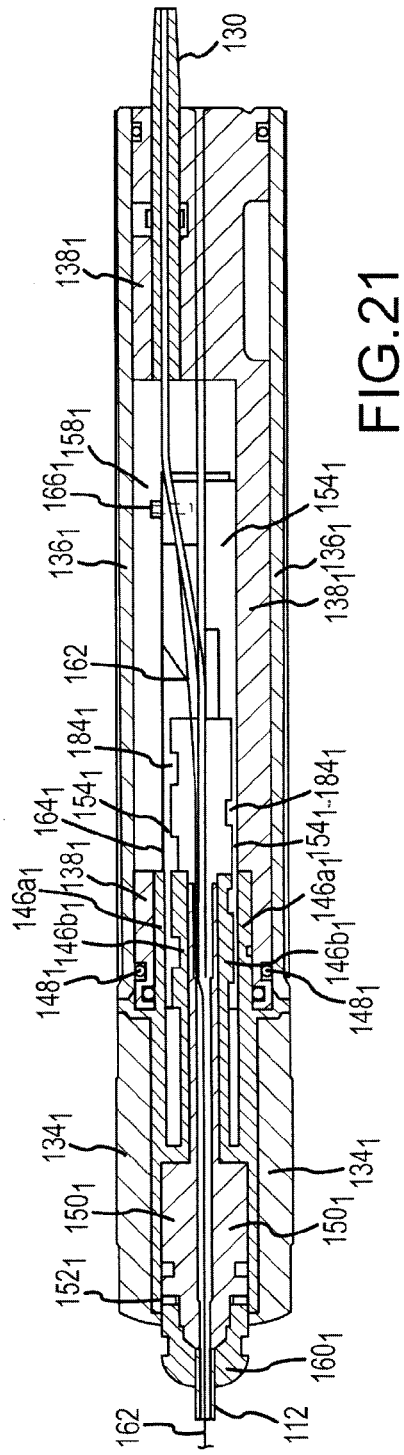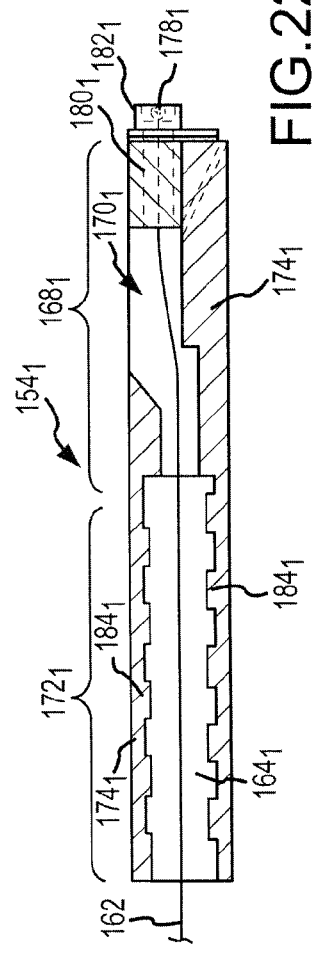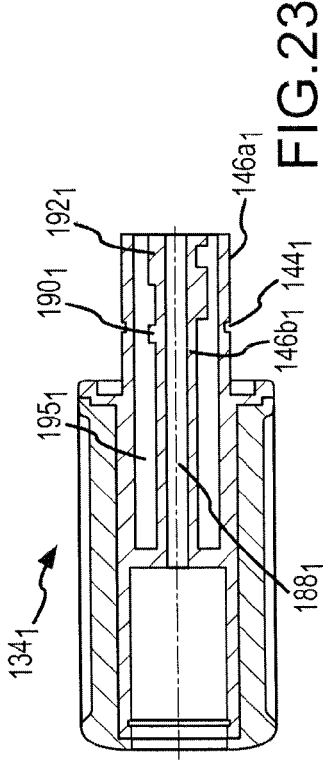

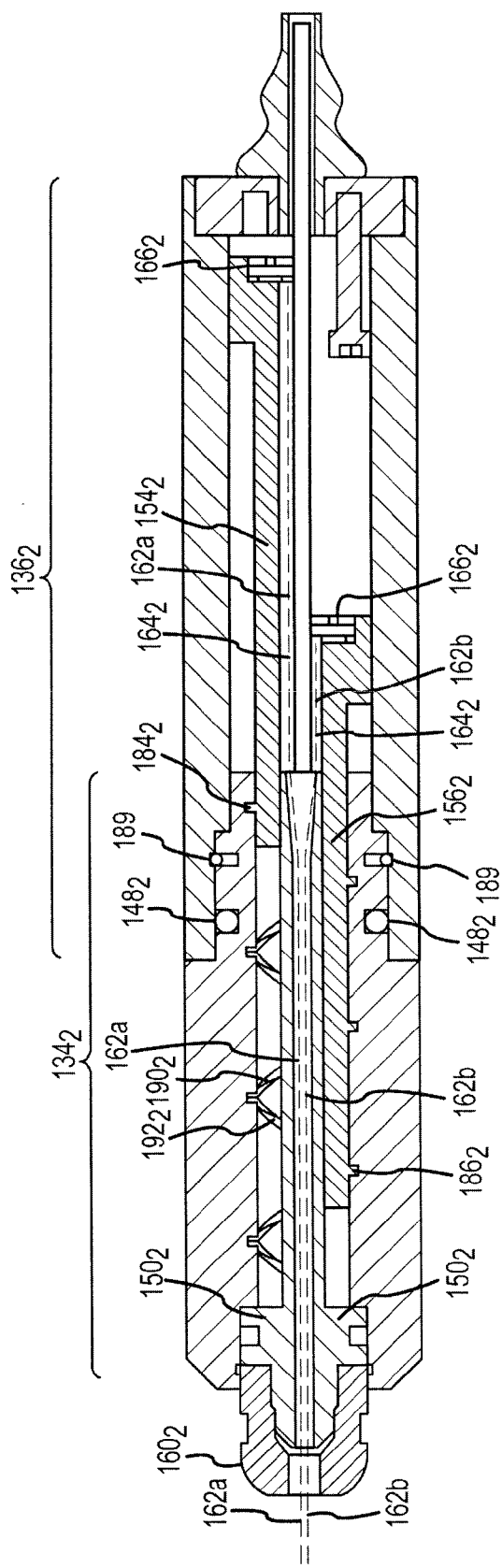
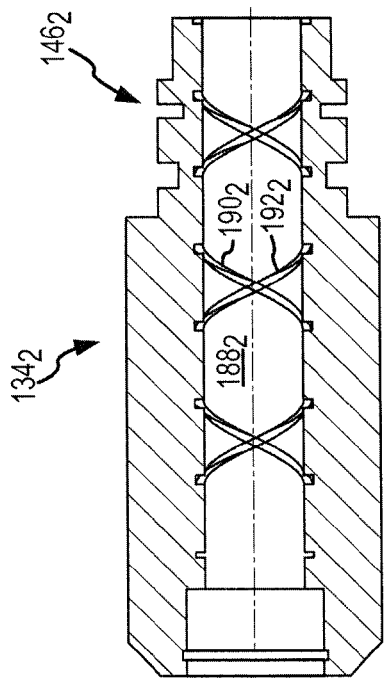

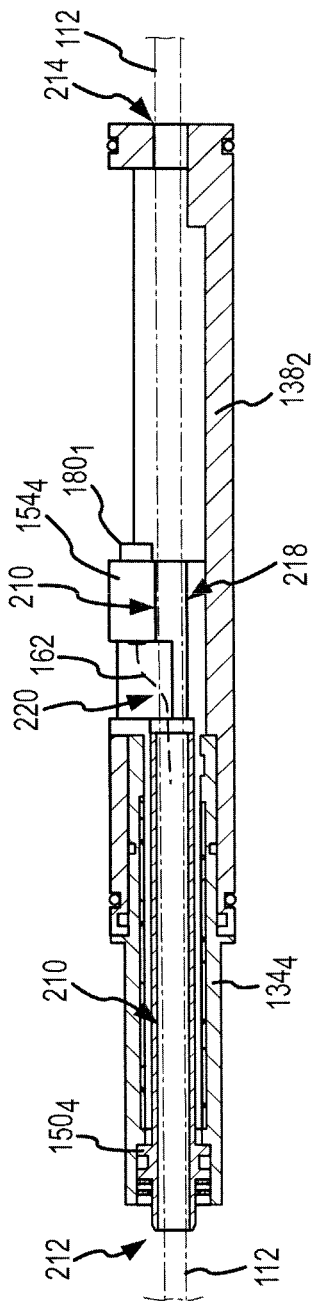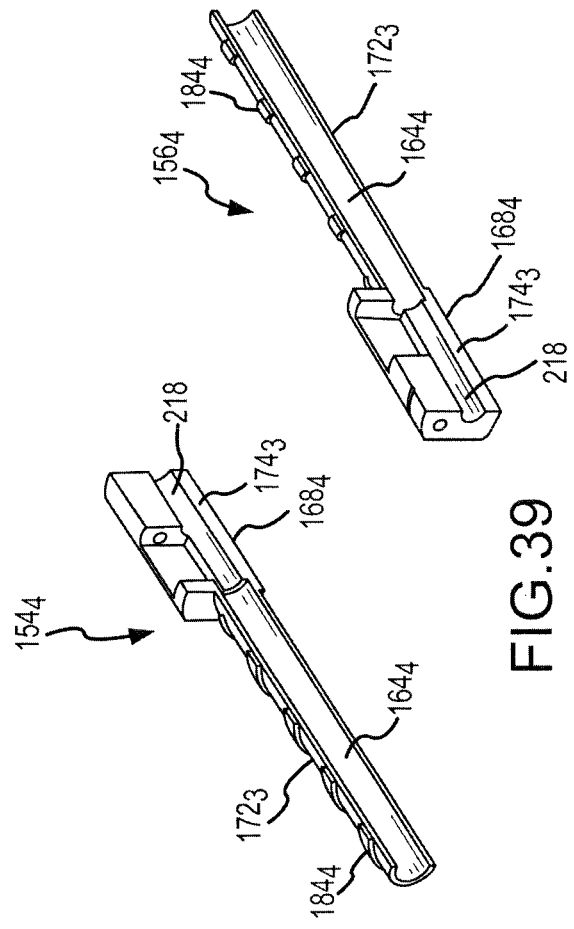
FIG.38
FIG.39

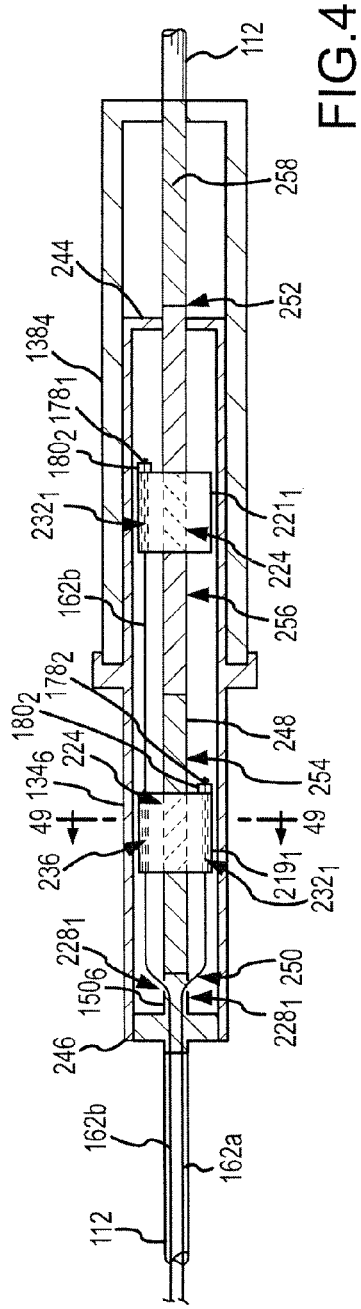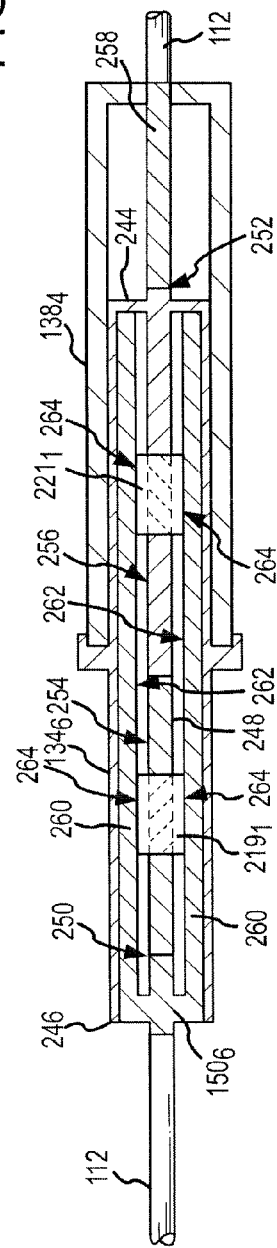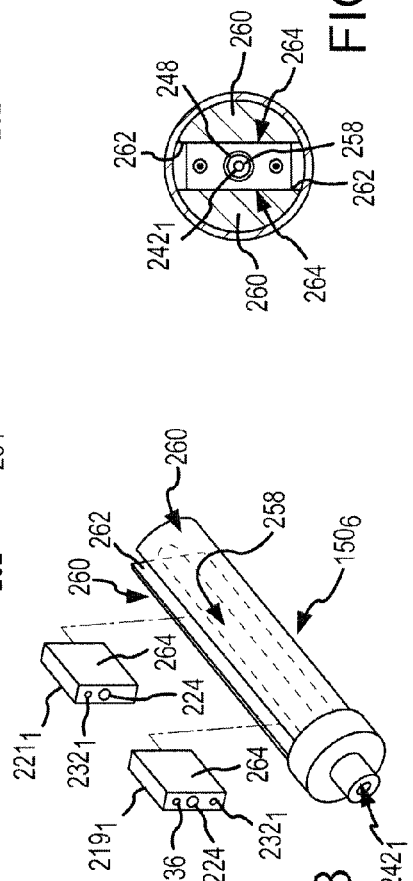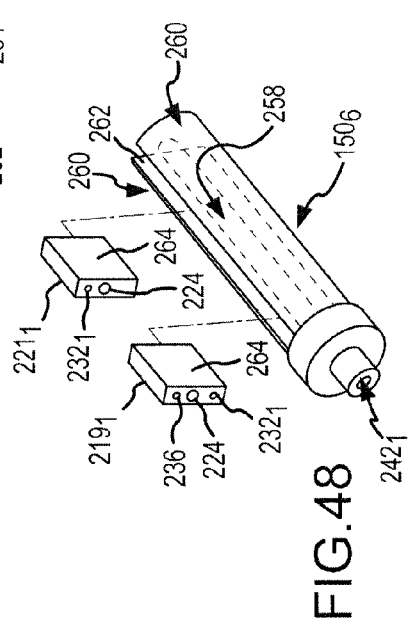
FIG. 46
FIG. 47
FIG. 48
FIG. 49

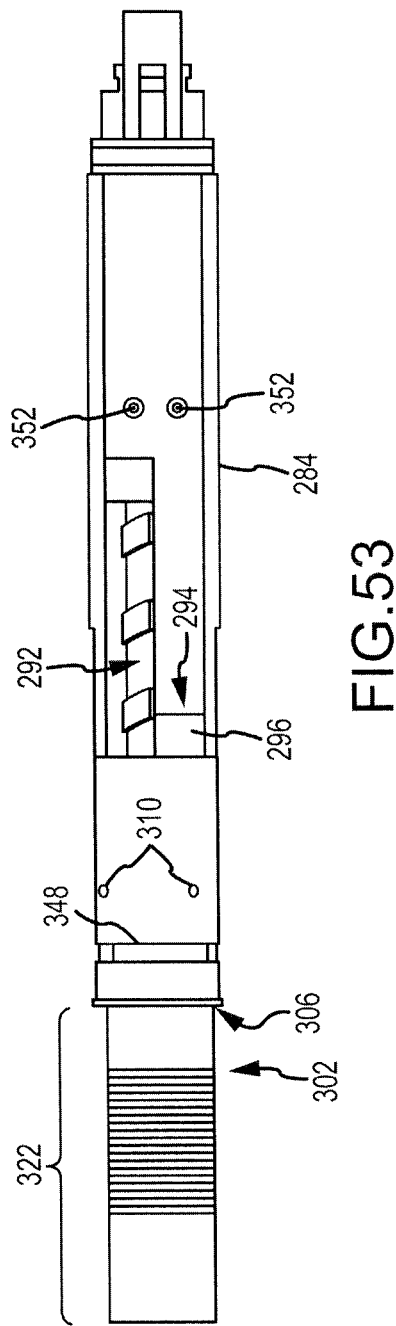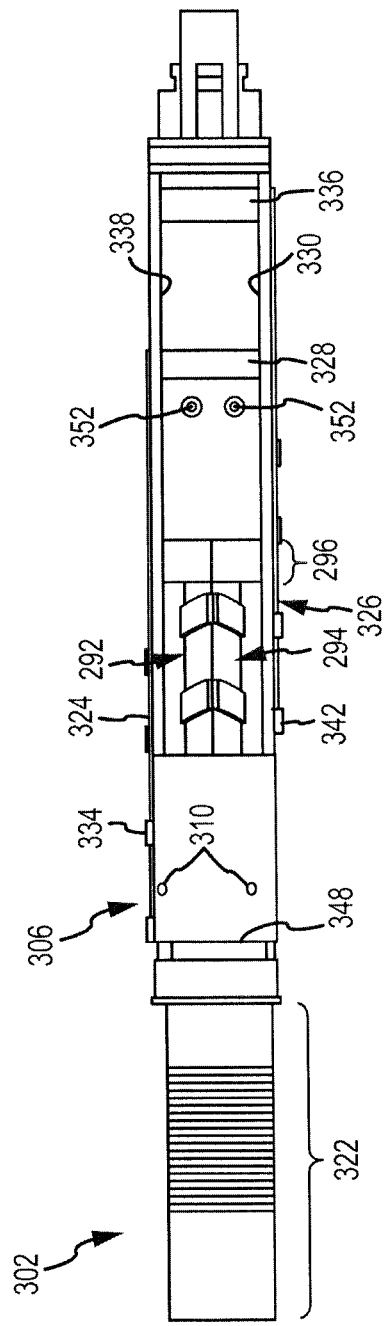
FIG.53
FIG.54

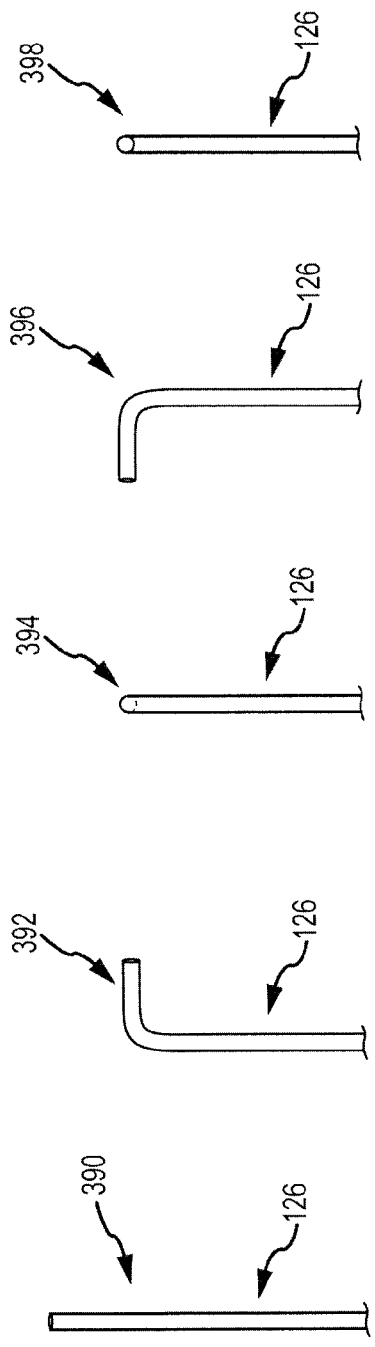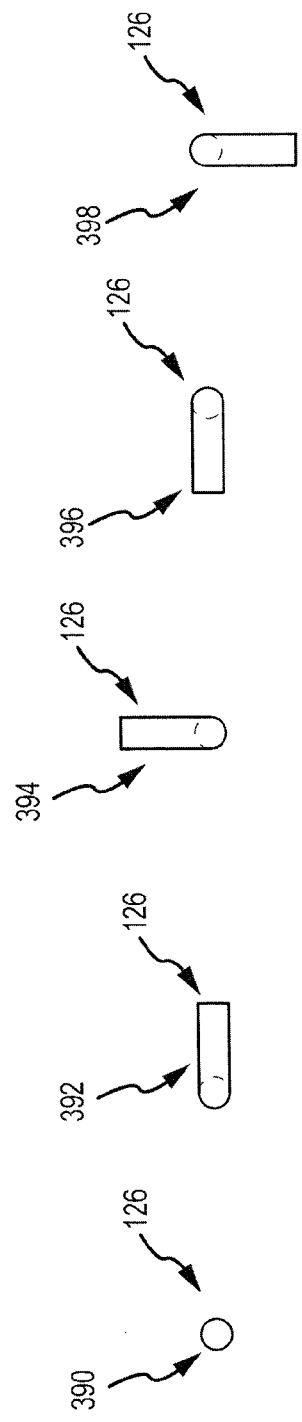

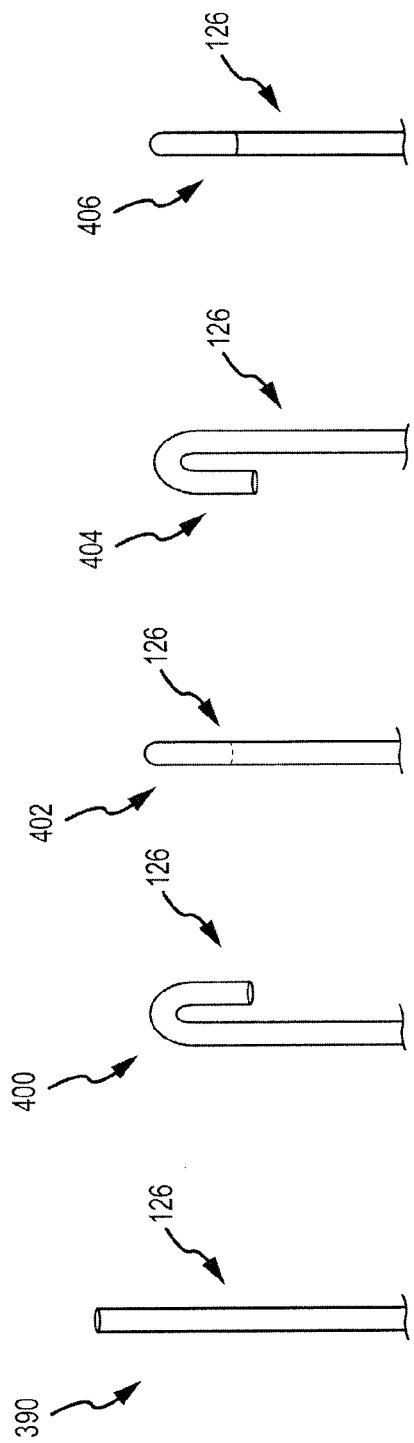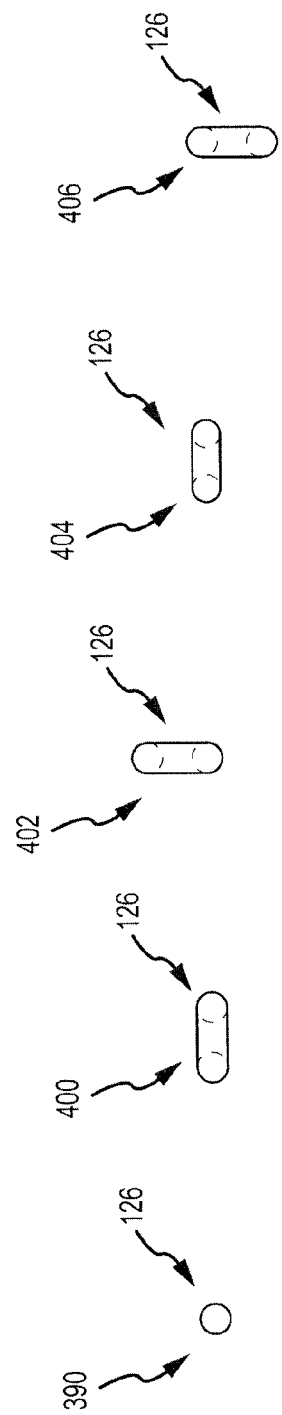

SHAFT AND HANDLE FOR A CATHETER WITH INDEPENDENTLY-DEFLECTABLE SEGMENTS

CROSS-REFERENCE TO RELATED APPLICATIONS

This application is a continuation-in-part of U.S. application Ser. No. 12/347,100, filed Dec. 31, 2008, now pending (the '100 application); and this application is a continuation-in-part of U.S. application Ser. No. 13/105,646, filed May 11, 2011, now pending (the '646 application), which claims priority to U.S. provisional application No. 61/333,641, filed May 11, 2010 (the '641 application). The '100 application, the '646 application, and the '641 application are all hereby incorporated by reference as though fully set forth herein.

BACKGROUND OF THE INVENTION a. Field of the Invention

The instant disclosure relates to elongate medical devices. Specifically, the instant disclosure relates to the design and construction of elongate medical devices with independently-deflectable shaft segments and handles for deflecting those shaft segments.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter typically carries one or more electrodes, which may be used for ablation, diagnosis, or the like.

To increase the ability to move and navigate a catheter within a patient's body, steerable catheters have been designed. Steerable catheters are often manipulated by selectively tensioning one or more pull wires (or deflection wires) running along the length of the catheter, typically offset from a central axis of the catheter, thereby deflecting the distal end of the steerable catheter in one or more planes. These pull wires are often attached to a metallic catheter component located at the distal end of the catheter, such as one of the electrodes carried on the distal end of the catheter or a pull ring incorporated in the catheter.

Steerable catheters often have a steering mechanism near the distal end of the catheter. This steering mechanism typically includes a pull ring and one or more pull wires (or deflection wires) attached thereto and extending proximally towards an actuator that can place the wire or wires in tension. Placing a pull wire in tension causes the distal end of the catheter to deflect in at least one plane. In this fashion, the catheter can be navigated through the tortuous path of a patient's vasculature to a target site. Because of the length of the path that a catheter may need to travel to reach a target site, however, deflectability of only the distal end of the catheter may not provide the practitioner with as great a level of steerability as the practitioner might desire.

In addition, once the catheter has been positioned at the target site, it often becomes necessary for the catheter to assume a particular shape in order to perform its desired function (e.g., a spiral shape for electrophysiological mapping of the ostium of a pulmonary vein). Deflectability of only the distal end of the catheter may not provide the practitioner with the flexibility to deform the catheter into all desirable shapes.

Like known catheter shafts, known control handles for controlling deflection of catheter bodies have several drawbacks that adversely impact the handles' ability to be operated. First, the control handles are often excessively bulky. Second, the control handles are often inadequate with respect to their ability to provide finely controlled deflection adjustment for the distal end of the catheter body. Third, the control handles often provide inadequate deflection wire travel for a desired medical procedure. Fourth, the control handles often have a mechanical advantage that is less than desirable and, as a result, require significant effort to operate on the part of a user. Fifth, once a desired body distal end deflection has been reached, the control handles typically require the physician to take a conscious step to maintain the catheter at the desired deflection. Sixth, the wire displacement mechanisms within the control handles have a tendency to permanently deform the deflection wires. Seventh, the wire displacement mechanisms within the control handles typically make it difficult, if not impossible, to provide a lumen that runs uninterrupted from the proximal end of the control handle to the distal end of the catheter body.

There is therefore a need for a catheter that minimizes or eliminates one or more of the problems set forth above.

BRIEF SUMMARY OF THE INVENTION

To address one or more of the problems set forth above, it may be desirable to provide an elongate medical device with independently-deflectable segments and a handle for manually deflecting those segments. Such an elongate medical device may include a shaft having a distal segment and proximal segment, at least one proximal segment deflection wire adapted to deflect the proximal segment, at least one distal segment deflection wire adapted to deflect the distal segment independent of the proximal segment, and a handle portion. The handle portion may comprise a first manual actuation mechanism coupled to the at least one distal segment deflection wire and a second manual actuation mechanism coupled to the at least one proximal segment deflection wire. Actuation of the first manual actuation mechanism may impart a tensile force on the distal segment deflection wire to cause the distal segment to deflect, and actuation of the second manual actuation mechanism may impart a tensile force on the proximal segment to cause the proximal segment to deflect.

In another embodiment, an elongate medical device may include a shaft comprising a distal segment and a proximal segment, a distal segment deflection member configured to deflect the distal segment independent of said proximal segment, a proximal segment deflection member configured to deflect the proximal segment, and a handle. The distal segment deflection member may have a distal end coupled with the shaft distal segment and a proximal end, and the proximal segment deflection member may have a distal end coupled with the shaft proximal segment and a proximal end. The handle may be coupled to the proximal segment deflection member proximal end and the distal segment deflection member proximal end, and may be configured to control the deflection of the shaft proximal segment and the shaft distal segment.

An embodiment of a catheter shaft that may be used, for example, in one or more of the embodiments above may include a proximal segment having a proximal segment wall and defining a proximal segment lumen and a distal segment. The shaft can further include at least one deflection wire lumen extending through the proximal segment wall and at least one proximal segment deflection wire configured to deflect the proximal segment. Each of the at least one proximal segment deflection wire may extend through a respective one of the at least one deflection wire lumen. The shaft can further include at least one distal segment deflection wire extending through the proximal segment lumen, the at least one distal segment deflection wire configured to deflect the distal segment.

BRIEF DESCRIPTION OF THE DRAWINGS

FIGS. 10A and 10B are partial cross-sectional views of, respectively, a manufacturing build-up that may be used to make an embodiment of a catheter body, and the finished embodiment.

FIG. 21 is a cross-sectional view of an embodiment of the interior of the catheter handle of FIG. 15, taken substantially along line 21-21 of FIG. 15.

FIG. 22 is a cross-sectional view of the slide of the catheter handle of FIG. 21.

FIG. 23 is a cross-sectional view of an embodiment of the interior of the adjusting knob of the catheter handle of FIG. 15, taken substantially along line 23-23 of FIG. 15.

FIG. 27 is a cross-sectional view of the catheter handle of FIG. 26, taken substantially along line 27-27 of FIG. 26.

FIG. 28 is a cross-sectional view of the adjusting knob of the catheter handle of FIG. 26, taken substantially along line 28-28 in FIG. 26.

FIG. 38 is a cross-sectional view of the catheter control handle of FIG. 37 taken substantially along line 38-38 in FIG. 37.

FIG. 39 is an isometric view of the slides of the handle of FIG. 37.

FIG. 46 is a cross-sectional view of an embodiment of a catheter handle similar to the handle shown in FIG. 40, taken substantially along a line similar to line 46-46 of FIG. 40.

FIG. 47 is a cross-sectional view of the catheter handle of FIG. 46, taken substantially along a line similar to line 47-47 in FIG. 40.

FIG. 48 is an isometric view of an embodiment of a wire guide, such as may be used with the catheter handle of FIG. 46.

FIG. 49 is a cross-sectional view of the catheter handle of FIG. 46, taken substantially along line 49-49 in FIG. 46.

FIGS. 53-55 are top views of an embodiment of a multi-directional catheter control handle in various states of sub-assembly.

FIGS. 59A-59E and FIGS. 60A-60E show respective side and top views of a distal portion of a partially-deflected catheter, sheath, medical device, or other flexible elongate member.

FIGS. 61A-61E and FIGS. 62A-62E show respective side and top views of a distal portion of a more-fully-deflected catheter, sheath, medical device, or other flexible elongate member.

DETAILED DESCRIPTION OF THE INVENTION

Figure 1:
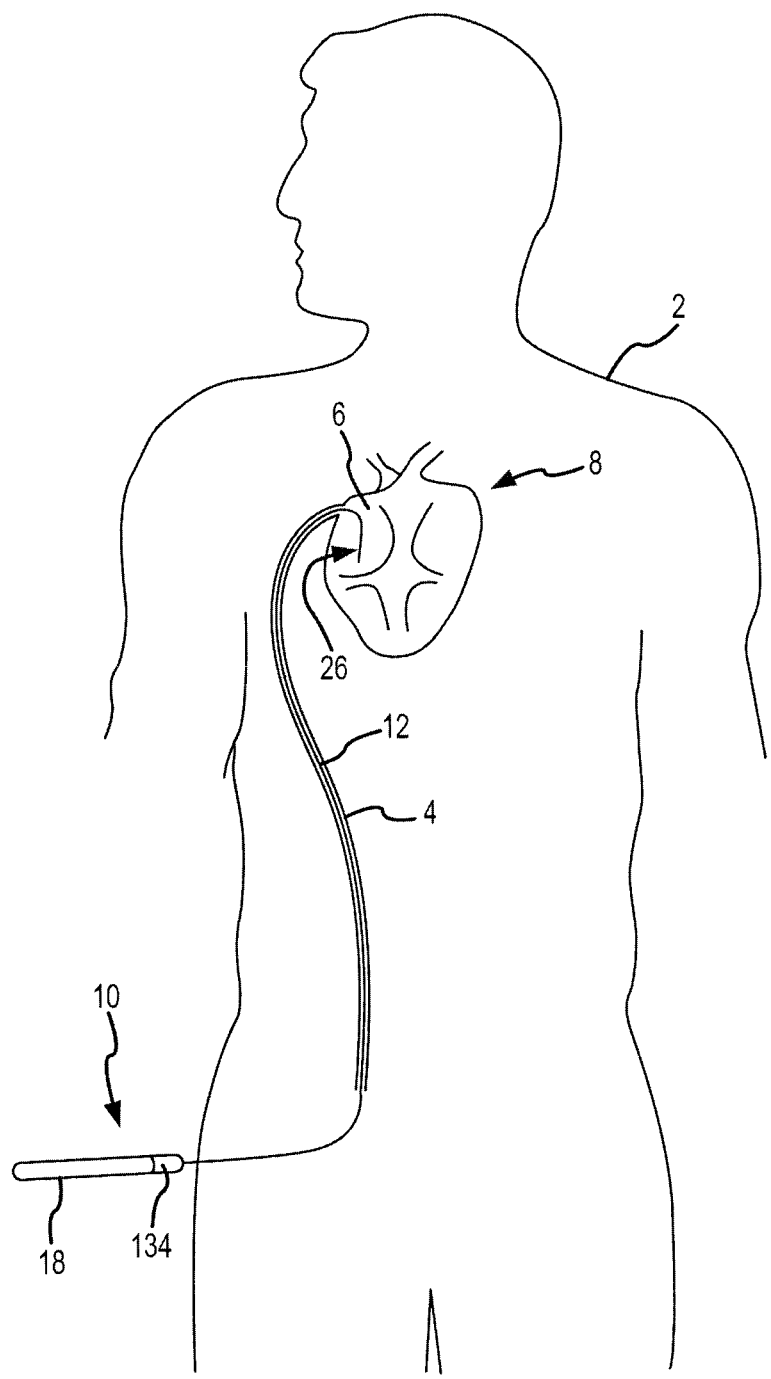
FIG. 1 is a diagrammatic view of a catheter being employed in a surgical procedure on a patient.

Referring now to the Figures, in which like reference numerals refer to the same or similar features in the various views, FIG. 1 is a diagrammatic view of a patient 2 with a body lumen 4 providing access to a chamber 6 of a heart 8. FIG. 1 also shows an elongate medical device 10 being used for a medical procedure on the heart 8. Throughout this disclosure, the terms elongate medical device, catheter, and flexible elongate member are meant to be interchangeable except where noted otherwise and include, without limitation, catheters, sheaths, and similar medical devices. The elongate medical device 10 includes a shaft 12 with a distal end 26 and a control handle 18 having an adjustment knob 134. The shaft 12 can be inserted into the body of the patient 2 intravenously via the body lumen 4, percutaneously, or via other avenues for entering the patient's body and guided through the body of the patient 2 so that the distal end 26 can be disposed in the heart chamber 6 to, for example only, perform an ablation procedure, mapping procedure, or other treatment or diagnostic procedure. The shaft 12 may include a number of features, such as deflection wires and pull rings, as will be detailed herein, to enable a physician to advance the distal end 26 of the elongate medical device 10 to an intended destination, such as a heart chamber 6, other portion of the heart 8, another organ, or another location in the body. The handle 18 may also include a number of features for advancing and guiding the shaft 12, such as one or more adjustment knobs 134, other external manual actuation mechanisms, and internal components for translating force on an actuating mechanism into tension on a deflection wire. In an embodiment, the features of the elongate medical device 10 may allow for independent deflection of two segments of catheter shaft 12, multi-directional deflection of the distal end 26, or both.

It may be desirable to deflect a catheter shaft 12 in multiple directions and/or to deflect several segments of the shaft 12 independently to improve guidance and positioning of the distal end 26 for diagnostic and/or therapeutic procedures on a heart chamber 6 or other target. Accordingly, the present disclosure describes a number of embodiments of a steerable or deflectable catheter suitable for use in the human vasculature for known medical procedures, such as cardiac diagnostic and therapeutic procedures including, without limitation, electrophysiological mapping and cardiac ablation. The disclosure first will describe, generally in conjunction with FIGS. 2-14, various embodiments of a deflectable catheter shaft 12 that, in an embodiment, allow for independent deflection of two segments of the shaft 12, as well as methods for manufacturing those shaft embodiments. Next, generally in conjunction with FIGS. 15-62, various embodiments of a control handle 18 for advancing and deflecting one or more catheter shaft segments will be described. Though generally described separately, the shaft embodiments of FIGS. 2-14 can be combined with appropriate handle embodiments from FIGS. 15-62 to construct a catheter with a desired number and configuration of deflection wires and deflectable segments.

Figure 2:
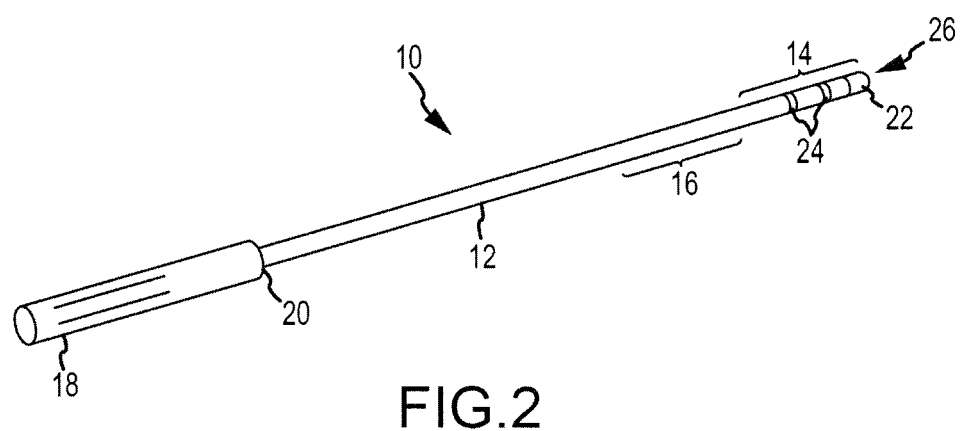
FIG. 2 is an isometric view of an embodiment of a catheter.

FIG. 2 is an isometric view of an embodiment of a steerable electrophysiology catheter 10 that includes an elongate catheter body or shaft 12 having a distal segment 14 and a proximal segment 16. As described in further detail below, distal segment 14 and proximal segment 16 may be advantageously independently deflectable—that is, distal segment 14 can be deflected independent of proximal segment 16 and vice-versa. This desirably imparts additional flexibility to catheter 10, for example by permitting catheter 10 to be deflected into configurations that would not otherwise be attainable. A handle 18 may be coupled to a proximal end 20 of catheter body 12 to control catheter 10, for example to control the deflection of distal segment 14 and proximal segment 16.

A plurality of electrodes, such as tip electrode 22 and ring electrodes 24, may be located near the distal end 26 of catheter body 12, for example within distal segment 14 as illustrated. Of course, it is within the scope of the present invention for electrodes to be present within proximal segment 16 in addition to or instead of within distal segment 14. By way of example only, electrodes 22, 24 may be used to deliver ablating energy to a tissue surface during an ablation procedure, for example to treat atrial fibrillation, or to measure electrophysiological characteristics during a diagnostic procedure, for example to map conduction pathways on a patient's heart. One of ordinary skill in the art will appreciate how to attach electrodes 22, 24 to catheter body 12.

One suitable method of manufacturing catheter body 12 will be described with reference to FIGS. 3-5. As they are assembled, the catheter components will be collectively referred to as a "catheter assembly."

Figure 3:
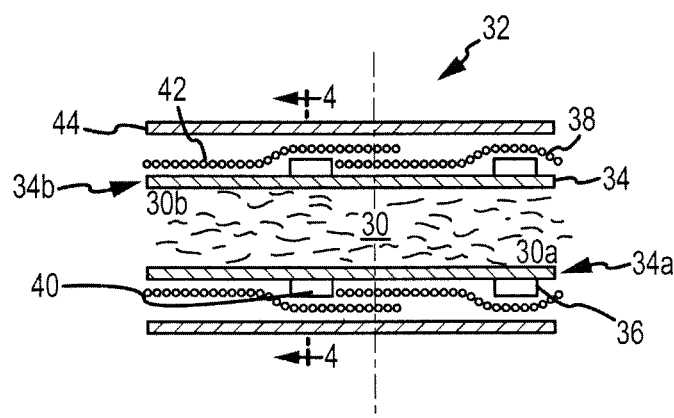
FIG. 3 is a longitudinal cross-sectional view of a an embodiment of a catheter body prior to the application of a reflow lamination process.

FIG. 3 is a longitudinal cross-sectional view of a catheter assembly prior to the application of heat to melt process the outer layer. As depicted in FIG. 3, a mandrel 30, which may be round in cross-section, is a component of catheter assembly 32, and may be the first component thereof during manufacture of catheter body 12. An inner layer 34 is placed on mandrel 30. Inner layer 34 may be knotted at one end (e.g., the distal end) and then fed onto mandrel 30. Of course, mandrel 30 and inner layer 34 may have any shape consistent with the desired final lumen configuration and/or intended use of catheter 10.

Mandrel 30 has a distal segment 30a and a proximal segment 30b. Likewise, inner layer 34 has a distal segment 34a and a proximal segment 34b. For the sake of illustration only, distal segments 30a, 34a and proximal segments 30b, 34b are shown as divided by a dashed vertical line. The actual location of the division between distal segments 30a, 34a and proximal segments 30b, 34b can be varied as desired for a particular configuration and/or intended use of catheter 10. For example, the distal segment can be made longer than the proximal segment if a higher degree of deflection is desired in the distal segment than in the proximal segment. Alternatively, the distal segment can be made shorter than the proximal segment if a higher degree of deflection is desired in the proximal segment than in the distal segment.

In an embodiment of the invention, inner layer 34 is an extruded polytetrafluoroethylene (PTFE) tubing, such as TEFLON® brand tubing, which is available commercially. In other forms, inner layer 34 may be made of other melt processing polymers, including, without limitation, etched polytetrafluoroethylene, polyether block amides, nylon, and other thermoplastic elastomers. One such elastomer is PEBAX®, made by Arkema, Inc. PEBAX® of various durometers may be used, including, without limitation, PEBAX® 30D to PEBAX® 70D. According to one aspect of the invention, inner layer 34 is made of a material with a melting temperature higher than that of an outer layer, which will be further described below, such that inner layer 34 will withstand melt processing of the outer layer.

A distal segment steering mechanism may then be formed about distal segment 34a of inner layer 34. In some embodiments, the distal segment steering mechanism will include at least one distal segment pull ring 36 to which one or more distal segment deflection wires may be attached. One of ordinary skill in the art will appreciate that these deflection wires may be connected to distal segment pull ring 36 prior to or after melt processing of catheter assembly 32. In some embodiments of the invention, the distal segment deflection wires are attached after melt processing of catheter assembly 32.

Optionally, a first wire reinforcing layer 38 may be formed over inner layer 34, and optionally also about the distal segment steering mechanism (e.g., distal segment pull ring 36). It is contemplated that first wire reinforcing layer 38 may be a braided wire assembly formed about distal segment 34a and at least a portion of proximal segment 34b of inner layer 34 that serves to both reinforce catheter body 12 and to transmit torque along the length of catheter body 12. Such an assembly may be formed of stainless steel wire, including for example 0.003" high tensile stainless steel wire, and may be formed in a standard braid pattern and density, for example, about 16 wires at about 45 to about 60 picks per inch ("PPI") density. Alternatively, a braid may be used that is characterized by a varying braid density. For example, the braided wire assembly may be characterized by a braid density that varies along the length of inner layer 34. The braid density nearer distal end 26 of catheter body 12 may be greater or less than the braid density at more proximal locations along catheter body 12. As but one example, the braid density near distal end 26 of catheter body 12 may be about 10 PPI, while the braid density at more proximal locations may be as high as about 50 PPI. As another example, the braid density near distal end 26 may be about 20% to about 35% of the braid density at more proximal locations. One of ordinary skill in the art will appreciate how to select a suitable braided wire assembly for a particular application of catheter 10.

First wire reinforcing layer 38 may be formed separately on a disposable core. One or more portions of first wire reinforcing layer 38 may be heat tempered and cooled before incorporation into catheter assembly 32 though methods that are known to those of ordinary skill in the art. The action of heat tempering may help to release the stress on the wire and help reduce radial forces. It is also contemplated that first wire reinforcing layer 38 may be formed directly on catheter assembly 32, for example by passing catheter assembly 32 through a braiding machine during assembly thereof. In still other embodiments, distal segment pull ring 36 is formed about first wire reinforcing layer 38.

A proximal segment steering mechanism may then be formed about proximal segment 34b of inner layer 34. In some embodiments, the proximal segment steering mechanism will include at least one proximal segment pull ring 40 to which one or more proximal segment deflection wires may be attached. Like the distal segment deflection wires described above in connection with the distal segment steering mechanism, one of ordinary skill in the art will appreciate that these deflection wires may be connected to proximal segment pull ring 40 prior to or after melt processing of catheter assembly 32. In some embodiments of the invention, the proximal segment deflection wires are attached after melt processing of catheter assembly 32. Of course, proximal segment pull ring 40 may be formed directly about proximal segment 34b of inner layer 34 (as shown in FIG. 3) or about a more proximal portion of first wire reinforcing layer 38.

Optionally, a second wire reinforcing layer 42 may be formed over inner layer 34, and, in some aspects of the invention, also about the proximal segment steering mechanism (e.g., proximal segment pull ring 40). In certain embodiments, second wire reinforcing layer 42 is a braided wire assembly formed about proximal segment 34b and at least a portion of distal segment 34a of inner layer 34 that serves to both reinforce catheter body 12 and to transmit torque along the length of catheter body 12. In some embodiments of the invention, first and second wire reinforcing layers 38, 42 overlap adjacent the boundary between distal segment 34a and proximal segment 34b of inner layer 34. The description of first wire reinforcing layer 38 herein (e.g., suitable materials, braid densities, and the like) applies to second wire reinforcing layer 42 as well.

An outer layer 44 is then placed over catheter assembly 32 (e.g., inner layer 34; first and second wire reinforcing layers 38, 42 (if present); distal segment pull ring 36; and proximal segment pull ring 40). According to some aspects of the invention, outer layer 44 is made of one or more polymeric materials, such as any of the polymeric materials described above in connection with inner layer 34. Outer layer 44 may be made of either single or multiple sections or segments of tubing that may be either butted together or overlapped with each other, and the sections may vary in hardness and in length as desired for a particular application or intended function of catheter 10. For example, the hardness of outer layer 44 may decrease distally or proximally, or may provide a segment of increased hardness between two segments of lesser hardness. The various segments will be bonded together in subsequent processing, resulting in a catheter body that has longitudinally varying stiffness, which may be desirable in certain applications of catheter 10.

It is also contemplated for outer layer 44 to include more than one concentrically-arranged layer, for example two or more layers of melt-processing polymeric material, which may vary radially in hardness. That is, a first, inner layer of outer layer 44 may have a first hardness, while a second, outer layer of outer layer 44 may have a second hardness. If a radially-varying outer layer 44 is utilized, the second, outer layer of outer layer 44 may have a lower hardness than the first, inner layer of outer layer 44 to facilitate an atraumatic catheter body 12.

Figure 4:
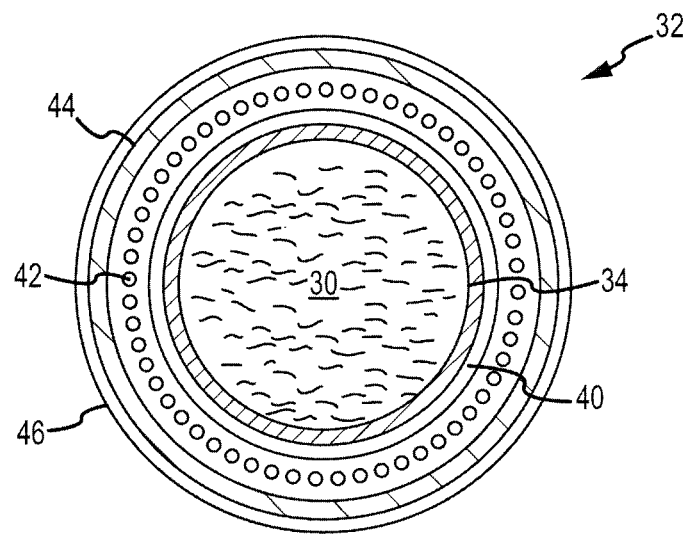
FIG. 4 is a cross-sectional view of a catheter body taken along line 4-4 in FIG. 3.

FIG. 4 depicts a cross-section of catheter assembly 32 taken along line 4-4 in FIG. 3 before lamination of the materials by heating. In one embodiment, a layer of heat shrink 46 is placed over the top of outer layer 44 prior to lamination. Heat shrink 46 may be a fluoropolymer or polyolefin material.

Figure 5:
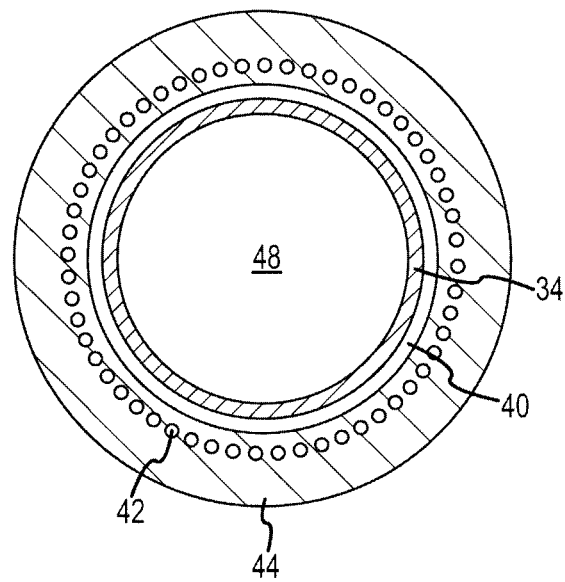
FIG. 5 is the cross-sectional view of FIG. 4 after the application of a reflow lamination process.

FIG. 5 depicts catheter assembly 32 after a lamination process. Catheter assembly 32 may be laminated by heating catheter assembly 32 until the material comprising outer layer 44 flows and redistributes around the circumference thereof as depicted in FIG. 5. Heat shrink 46 has a higher melting temperature than outer layer 44. During the melt process, heat shrink 46 retains its tubular shape and forces the liquefied outer layer 44 material into first and second wire reinforcing layers 38, 42 (if present), around distal segment pull ring 36 and proximal segment pull ring 40 (e.g., as described below), and into contact with inner layer 34. Catheter assembly 32 may then be cooled.

Mandrel 30 may be removed from catheter assembly 32, leaving behind a lumen 48 as illustrated in FIG. 5, which depicts a catheter body 12 made in accordance with the method described above subsequent to the application of heat for the lamination process. Optionally, heat shrink 46 may be left in place around outer layer 44 even after mandrel 30 is removed, such that heat shrink 46 becomes the outermost layer of catheter body 12. If heat shrink 46 is removed, outer layer 44 becomes the outermost layer of catheter body 12. The result is a substantially circular and unitary catheter body 12 with a generally circular central lumen 48. First and second wire reinforcing layers 38, 42, distal segment pull ring 36, and proximal segment pull ring 40 are substantially embedded within outer layer 44 material as illustrated in FIG. 4.

Figure 6:
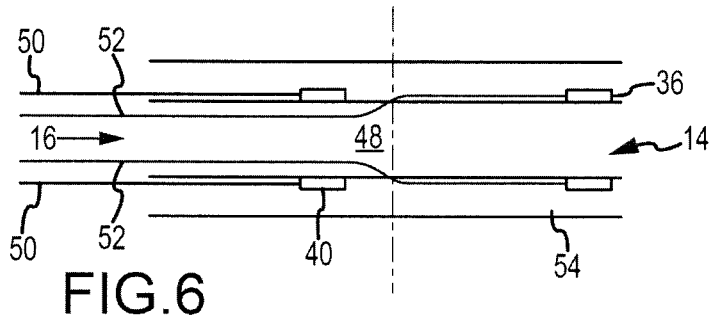
FIG. 6 is a simplified longitudinal cross-sectional view of an embodiment of a catheter body having independently-deflectable segments.
Figure 7:
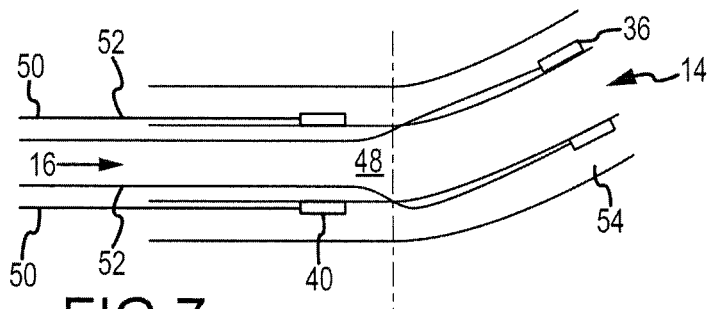
FIG. 7 depicts the catheter body of FIG. 6 with the distal segment deflected independent of the proximal segment.

As shown in FIG. 6, at least one proximal segment deflection wire 50 and at least one distal segment deflection wire 52 may then be placed into catheter body 12 and attached, respectively, to proximal segment pull ring 40 and distal segment pull ring 36 (if not placed prior to lamination of catheter assembly 32). As with FIG. 3, FIG. 6 shows a dashed vertical line separating distal segment 14 and proximal segment 16 for the sake of illustration. In addition, for the sake of clarity, first and second wire reinforcing layers 38, 42 are not shown in FIG. 6 and the laminated combination of inner layer 34 and outer layer 44 is shown as a substantially unitary wall 54.

In the embodiment depicted in FIG. 6, a pair of distal segment deflection wires 52 are connected to distal segment pull ring 36 and extend proximally (e.g., towards handle 18, not shown in FIG. 6). Within at least part of proximal segment 16 of catheter shaft 12, distal segment deflection wires 52 extend through lumen 48. As depicted, distal segment deflection wires enter wall 54 within proximal segment 16 and extend through wall 54 within distal segment 14, where they terminate at a connection to distal segment pull ring 36. Routing distal segment deflection wires 52 through lumen 48 in at least part of proximal segment 16 is desirable in that it reduces the complexity of wall 54 within proximal segment 16. Of course, it is within the scope of the invention for distal segment deflection wires 52 to enter wall 54 at a more proximal location than that depicted in FIG. 6, including extending entirely through wall 54 within proximal segment 16. Distal segment deflection wires 52 are adapted to deflect distal segment 14 in at least one plane independent of proximal segment 16 when placed in tension. As illustrated, distal segment deflection wires 52 will deflect distal segment 14 upward and downward (as shown FIGS. 7 and 9).

Figure 8:
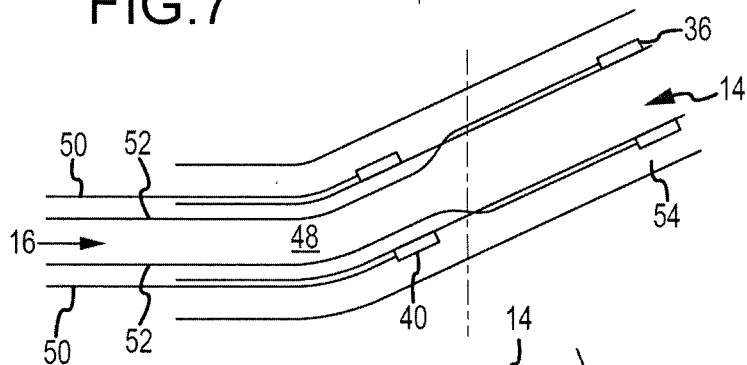
FIG. 8 depicts the catheter body of FIG. 6 with the proximal segment deflected independent of the distal segment.
Figure 9:
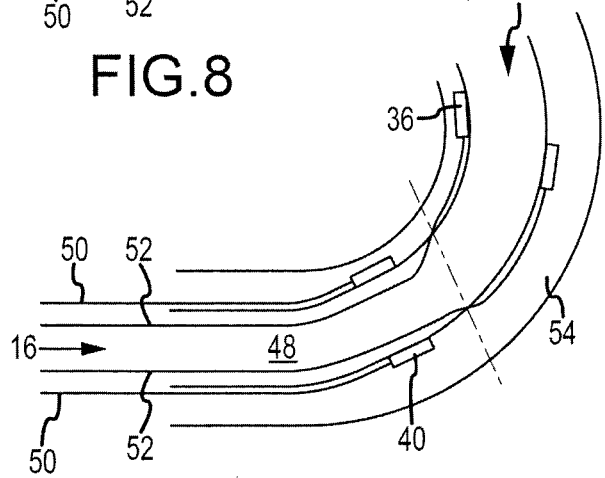
FIG. 9 depicts the catheter body of FIG. 6 with both the distal segment and the proximal segment deflected such that the catheter body assumes a partial spiral configuration.

A pair of proximal segment deflection wires 50 are connected to proximal segment pull ring 40 and extend proximally (e.g., towards handle 18, not shown in FIG. 6). As depicted, proximal segment deflection wires 50 extend entirely through wall 54. It is contemplated, however, that proximal segment deflection wires 50 may also extend at least partially through lumen 48. Proximal segment deflection wires 50 are adapted to deflect proximal segment 16 in at least one plane independent of distal segment 14 (i.e., independent of deflection caused by distal segment deflection wires 52) when placed in tension. As illustrated, proximal segment deflection wires 50 will deflect proximal segment 16 upward and downward (as shown in FIGS. 8 and 9).

Deflection wires 50, 52 may have any desired cross-section, such as circular, flat, elliptical, or any other shape. For example, a flat wire may be used when it is desirable for the resultant catheter to favor deflection along one axis and yet be predisposed to resist deflection along a second, generally orthogonal axis. Flat wires may also be employed to good advantage where it is desirable to have a low-profile (e.g., thin) wall for the resultant catheter, thereby to maximize the size of lumen 48 relative to the overall size of the catheter.

Any or all of deflection wires 50, 52 may also be a shape memory alloy wire, such as a wire containing nickel and titanium (known commercially as NiTi or Nitinol); copper, aluminum, and nickel; or copper, zinc, and aluminum. The shape memory effect facilitates returning distal segment 14 and proximal segment 16 of catheter body 12 to their original, undeflected ("home") positions when wires 50, 52 are unloaded (e.g., not placed in tension via a suitable actuator (not shown) or manual actuation mechanism on handle 18 of catheter 10).

In alternative embodiments, wires 50, 52 may be covered with lubricious materials including silicone, TEFLON®, siloxane, and other lubricious materials before placement. Alternatively, wires 50, 52 may also be coated with a lubricious layer to promote slideability. It is also contemplated that wires 50, 52 may be manufactured with a smooth surface to promote slideability. Wires 50, 52 may also be disposed in tubes with a lubricous inner lining, as shown in the embodiment of FIGS. 10A-12.

FIG. 9 depicts the catheter body of FIG. 6 with both distal segment 14 and proximal segment 16 deflected, illustrating the advantageous flexibility of a catheter shaft constructed according to the present invention. One advantage of the present invention is that it allows catheter 10 to be introduced and navigated through a patient's vasculature in one configuration (e.g., a substantially straight configuration) and then conveniently deflected into a second configuration upon reaching a target site. One of ordinary skill in the art will appreciate that, by providing additional deflection wires and/or by changing the location of distal segment pull ring 36 and/or proximal segment pull ring 40, distal end 26 of catheter body 12 can be steered through a patient's vasculature to a target site and then formed into any number of shapes. Examples of such shapes include spirals and C-shaped curves, both of which may be desirable in the creation of pulmonary vein isolation lesions.

FIGS. 10A-12 illustrate a second embodiment of a catheter shaft having independently-deflectable segments and a method for manufacturing the shaft. The embodiment illustrated in FIGS. 10A-12 may be referred to as a "catheter-on-catheter" assembly because its manufacture involves adding a proximal shaft segment to a completed distal shaft segment, as will be further described below. The embodiment shown in FIGS. 10A-12 can be used with an appropriate handle such as the embodiment shown in FIGS. 50-58.

FIG. 10A is a partial cross-sectional side view, with portions cut away, of a catheter assembly 56 in an intermediate stage of build-up for a "catheter-on-catheter" construction. The catheter assembly 56 includes a proximal segment 58 and a distal segment 60, which will respectively become proximal and distal segments of a finished catheter shaft after a reflow lamination process, disposed on a grooved mandrel 64 (shown in partial cross-section). For the sake of illustration only, proximal segment 58 and distal segment 60 are shown as divided by a dashed vertical line. The distal segment 60 includes a shaft 62 (shown in partial cross-section), a distal pull ring 66 embedded in the shaft 62, and two pull wires (shown in FIG. 11), also embedded in the shaft 62. The proximal segment 58 includes a proximal pull ring 68 (shown in partial cross-section), proximal pull wires 70, and an outer layer 72 (shown in partial cross-section).

The construction of a "catheter-on-catheter" assembly may begin with the manufacture of the inner catheter—i.e., the catheter shaft 62 forming distal segment 60. The catheter shaft 62 may be manufactured according to a method similar to that described above in conjunction with FIGS. 2-9, or by another method known in the art. Accordingly, the distal segment 60 may include other features not shown in FIG. 10A, such as a wire braid reinforcing layer, one or more electrodes (e.g., sensing or ablation electrodes) or other sensors, or other features known in the art.

The catheter shaft 62 also includes, as noted above, distal segment pull wires (shown in FIGS. 11 and 12). The distal segment pull wires may be embedded in a portion of the wall of the shaft 62 to extend from the distal pull ring 66 proximally through the wall of the shaft 62. At a point proximal of the distal pull ring 66, the distal deflection wires may transition through the wall of the shaft 62 and extend proximally through the center lumen of the shaft, similar to the configuration shown in FIGS. 6-9, for connection to a catheter handle at the proximal end of the finished shaft.

The grooved mandrel 64 may be placed through the center of finished catheter shaft 62. If the distal segment deflection wires extend through the center lumen of the shaft 62 (i.e., are not entirely embedded within the wall of the shaft 62), they may be threaded into grooves in the mandrel 64 so that the distal deflection wires do not become embedded in the wall of the proximal segment 58 during reflow lamination.

After the shaft 62 is placed on the mandrel 64, the proximal pull ring 68 may be placed about the shaft 62. As noted above, the deflected shape of the completed shaft can be affected by the positions of the proximal and distal pull rings. Accordingly, the axial location for the proximal pull ring 68 may be selected according to the desired deflection position of the proximal segment.

Proximal pull wires 70 may be placed over the shaft 62 and coupled to the proximal pull ring 68 by, for example only, welding. The proximal pull wires 70 may be placed in respective protective sheaths (shown in FIG. 12) so that the pull wires 70 do not become immovably embedded in the proximal segment 58 during reflow lamination. Each protective sheath may be lined on its interior surface with a lubricous material, such as TEFLON®, to allow the pull wires 70 to slide within the sheath with minimal friction. The proximal pull wires 70 (i.e., the protective sheaths) may also be bonded to the shaft 62 with adhesive or another means known in the art so that the proximal pull wires do not shift position during reflow lamination. The proximal pull wires 70 may be extended proximally through the assembly for connection to an appropriate handle. In an embodiment, the proximal pull wires 70 may be connected to the same handle as the distal pull wires. An embodiment of an appropriate handle for such a configuration is shown in FIGS. 50-58.

An outer layer 72 may be placed on top of and about the shaft 62, the proximal pull ring 68, and the proximal pull wires 70. The outer layer 72 may include an extruded PTFE tubing, such as TEFLON® brand tubing, which is available commercially. In other forms, the outer layer 72 may be made of other melt processing polymers, including, without limitation, etched polytetrafluoroethylene, polyether block amides, nylon, and other thermoplastic elastomers. One such elastomer is PEBAX®, made by Arkema, Inc. PEBAX® of various durometers may be used, including, without limitation, PEBAX® 30D to PEBAX® 70D.

The outer layer 72 may be made of either single or multiple sections or segments of tubing that may be either butted together or overlapped with each other, and the sections may vary in hardness and in length as desired for a particular application or intended function of the completed catheter. For example, the hardness of the outer layer 72 may decrease distally or proximally, or may provide a segment of increased hardness between two segments of lesser hardness. The outer layer 72 may also include more than one concentrically-arranged layer, for example two or more layers of melt-processing polymeric material, which may vary radially in hardness. That is, a first, inner layer of outer layer 72 may have a first hardness, while a second, outer layer of outer layer 72 may have a second hardness. If a radially-varying outer layer 72 is utilized, the second, outer layer of outer layer 72 may have a lower hardness than the first, inner layer of outer layer 72 to facilitate an atraumatic catheter body.

FIG. 10B is a cross-sectional view of catheter 56 of FIG. 10A in a further stage of manufacture, with portions broken away. In the illustrated embodiment, a distal tip RF ablation electrode 75 is incorporated into the catheter assembly 56. To complete the manufacture of the catheter-on-catheter assembly, a layer of heat shrink 73 may be placed about the proximal catheter assembly 56, and catheter assembly 56 may be exposed a reflow lamination process. During reflow, the outer layer 72 and the shaft 62 may melt and flow together to form a unitary shaft in which the proximal pull ring 68 and the proximal pull wires 70 can be embedded. However, depending on the properties of outer layer 72 and shaft 62 (e.g., the respective melting points of their materials), outer layer 72 and shaft 62 may remain distinguishable from, though affixed to, each other after reflow lamination. In an alternate embodiment, the heat shrink 73 may be placed only around the proximal segment 58, and only the proximal segment 58 can be exposed to reflow lamination.

Either before or after reflow lamination, one or more sensor and electrodes, such as the distal tip electrode 75, can be added to the catheter assembly 56. The distal tip electrode 75, along with any other sensors and electrodes included in the catheter assembly 56, can be used for diagnostic and/or therapeutic procedures such as, for example only, an RF ablation procedure. The distal tip electrode 75 can be joined to the catheter assembly 56 through a means known in the art such as, for example only, an adhesive.

Figure 11:
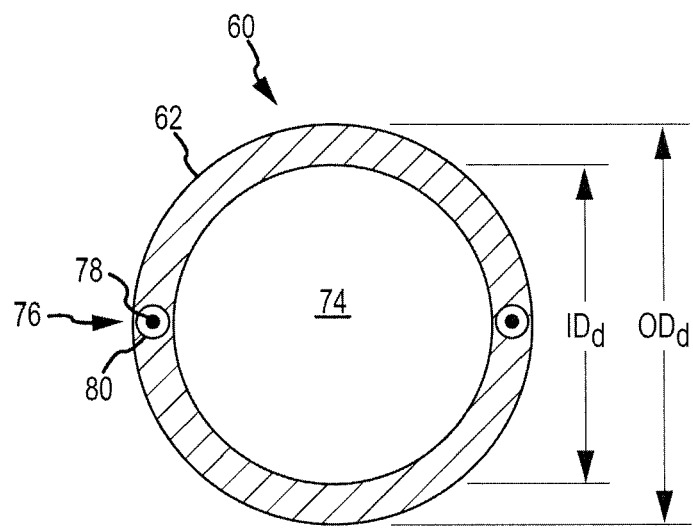
FIG. 11 is a cross-sectional view of the catheter body of FIG. 10A, taken substantially along line 11-11, after a reflow lamination process and the removal of the center mandrel.

FIG. 11 is a cross-sectional view of the distal segment 60 of the catheter assembly shown in FIG. 10A after the removal of the mandrel 64. The distal segment includes a shaft 62 defining a center lumen 74, and two distal pull wire assemblies 76, each of which includes a pull wire 78 and a protective sheath 80. Each pull wire assembly 76 is embedded in the wall of the shaft 62, i.e., disposed between the inner diameter $ID_d$ and outer diameter $OD_d$ of the shaft 62. Within the wall of the shaft 62, each sheath 80 defines a deflection wire lumen for a distal segment deflection wire 78.

Figure 12:
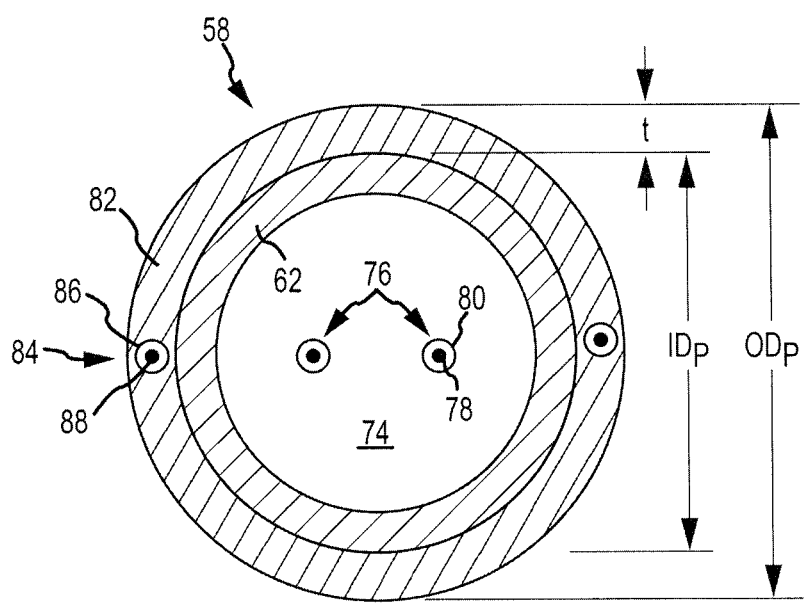
FIG. 12 is a cross-sectional view of the catheter body of FIG. 10A, taken substantially along line 12-12, after a reflow lamination process and the removal of the center mandrel.

FIG. 12 is a cross-sectional view of the proximal segment 58 of the catheter assembly shown in FIG. 10A after a reflow lamination process and the removal of the mandrel 64. After reflow, the proximal segment 58 includes an outer shaft portion 82, an inner shaft 62, two proximal deflection wire assemblies 84, each of which includes a protective sheath 86 and a deflection wire 88, and two distal deflection wire assemblies 78, each including a deflection wire 78 and a protective sheath 80, extending through the center lumen 74. Within the wall of the outer shaft portion 82, each sheath 86 defines a deflection wire lumen for a proximal segment deflection wire 88.

As noted above, the shaft 62 and outer layer 72 may reflow together into a unitary shaft, in an embodiment, or may remain separately identifiable (though affixed) layers after reflow, in another embodiment. FIG. 12 illustrates the latter. Accordingly, the outer shaft portion 82 may include material both from shaft 62 and outer layer 72, or may comprise only material from outer layer 72, as shown. In either embodiment, outer shaft portion 82 may add an identifiable thickness t to the catheter assembly 56 between an inner diameter $ID_p$ and an outer diameter $OD_p$ of the outer shaft portion 82.

A practical consequence of a catheter-on-catheter construction is that the outer diameter of the proximal segment $OD_p$ may be larger than the outer diameter of the distal segment $OD_d$. Accordingly, in an embodiment, it may be desirable to minimize the radial thickness t of the outer shaft portion 82 to minimize the total radial size (i.e., the outer diameter $OD_p$) of the proximal segment 58. One way that the thickness t of the outer shaft portion 82 can be minimized, as shown in FIGS. 10A-12, is by routing the distal segment deflection wire assemblies 76 through the lumen 74 of the proximal segment 58, rather than through the wall formed by outer shaft portion 82. In such an embodiment, the inner diameter $ID_p$ of the outer shaft portion 82 (which may also be the outer diameter of the distal segment 60) may be about 0.090 inches, the thickness t of the outer shaft portion 82 may be about 0.013-0.014 inches, and the outer diameter $OD_p$ of the outer shaft portion 82 may be about 0.116-0.118 inches. In addition, the diameter of the proximal deflection wire sheath 86 may be about 0.009 inches.

The proximal segment deflection wires 88 and distal segment deflection wires 78 can have a number of different shapes (i.e., in cross-section taken transverse to the central axis of the wire). The deflection wires 78, 88 can be substantially circular in cross-section, as shown in FIGS. 11 and 12, or can be "flat" with a substantially rectangular cross-section, or can have some other shape. Flat deflection wires may be used to reduce the outer diameter of the proximal segment 58 even further. In an embodiment, a flat deflection wire may have dimensions of about 0.012 inches wide by 0.004-0.006 inches thick.

Figure 13:
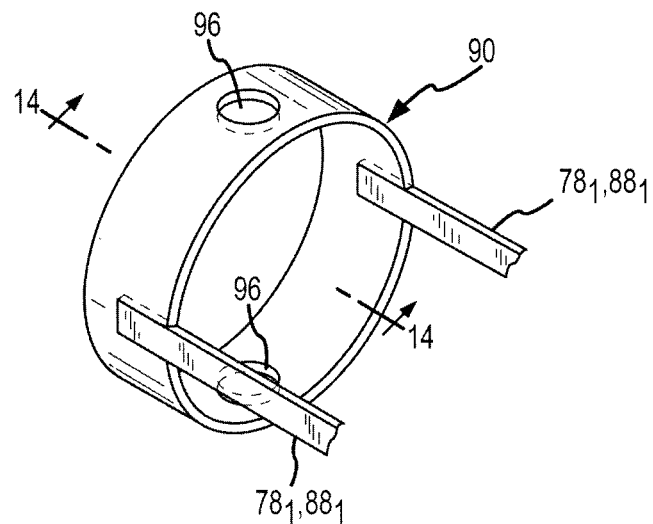
FIG. 13 illustrates an embodiment of a pull ring.
Figure 14:
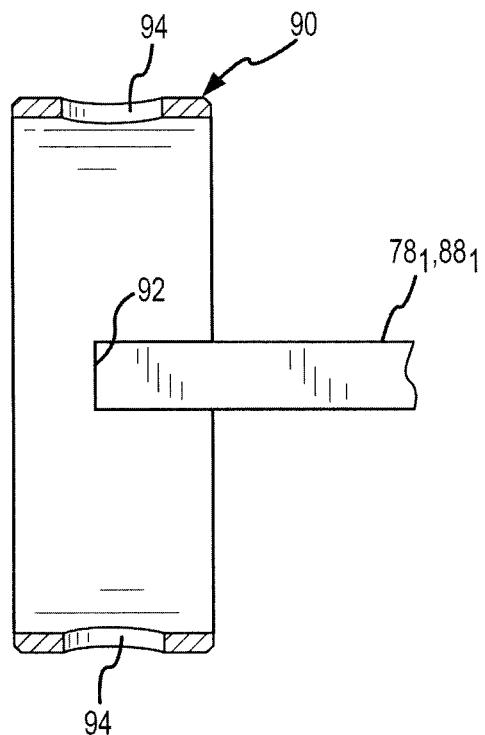
FIG. 14 is a cross-sectional view of the pull ring of FIG. 13, taken substantially along line 14-14.

FIGS. 13 and 14 illustrate a suitable pull ring 90 that may be employed as a distal segment pull ring 36, 66 and/or proximal segment pull ring 40, 68. The pull ring 90 is a generally circular band with a cross-sectional shape (measured orthogonally to a tangential line relative to the circle of the band) that is substantially rectangular. The rectangular cross-section is more clearly depicted in FIG. 14. The inner and outer dimensions of the pull ring 90 may be determined based on the application of the catheter being manufactured.

The pull ring 90 may have at least one slot 92 configured to accommodate a flat deflection wire (e.g., an embodiment of proximal segment deflection wire 78₁ or distal segment deflection wire 88₁). Wire 78₁, 88₁ may be secured within slot 92 by any technique that is appropriate given the materials of pull ring 90 and wire 78₁, 88₁. Acceptable techniques include, but are not limited to, soldering, brazing, laser welding and/or other welding and metallurgical bonding techniques.

Pull ring 90 may also contain one or more flow holes 96. During melt processing of catheter assembly 32, 56, the material of outer layer 44, 72 melts and flows through flow holes 96. Upon cooling, the material of outer layer 44, 72 bonds to pull ring 90 to provide better adhesion between pull ring 90 and the remaining components of catheter assembly 32, 56, thereby improving performance of the finished catheter. While the flow holes 96 are depicted as circular, other shapes may be used. The size, shape, and position of the flow holes 96 may be adjusted based on the materials being used to form inner layer 34 (or shaft 62) and/or outer layer 44, 72.

The pull ring may also be utilized with non-flat deflection wires. A pull ring according to this embodiment may be a circular band with a cross-sectional shape (measured orthogonally to a tangential line relative to the circle of the band) that is substantially rectangular. Such a pull ring may have at least one slot that is configured to accommodate a non-flat deflection wire (such as a round wire, e.g., deflection wires 78, 88). The tip of the non-flat deflection wire may be tapered to facilitate joinder with the pull ring. The non-flat deflection wire may be secured within the slot by any technique that is appropriate given the materials of the pull ring and the deflection wires.

Although several embodiments of a catheter shaft have been described above with a certain degree of particularity, those skilled in the art could make numerous alterations to the disclosed embodiments without departing from the spirit or scope of this invention. For example, though both the first and second wire reinforcing layers are described herein as braided wire assemblies, one of ordinary skill in the art will appreciate that other configurations of the first and second wire reinforcing layers, such as opposing helically-wound wire coils, may also be utilized to good advantage in the present invention.

As another example, though only two deflection wires spaced approximately 180 degrees apart in each of the proximal segment and the distal segment are shown and described above, it is contemplated that any number of deflection wires may be utilized. For example, each of the proximal segment and the distal segment may have four deflection wires spaced approximately 90 degrees apart.

In addition, some or all of the deflection wires may be attached directly to the wall of the catheter or to another metallic component of the catheter (e.g., a tip electrode) rather than to dedicated pull rings embedded in the wall of the catheter.

It is also contemplated that a catheter shaft 12 may be manufactured using techniques other than those described herein. For example, in some embodiments, an outer layer may be formed by extruding the outer layer over the rest of the catheter assembly. In other embodiments, the catheter assembly may be formed by using a combination of heat and a press that has a mold for defining the final shape of the catheter shaft.

One of ordinary skill in the art will also appreciate that a catheter assembly may also be provided with various tips, electrodes, and the like suitable for a particular application of a catheter either before or after reflow lamination (i.e., melt processing).

A catheter shaft manufactured according to the embodiments and methods described above can be combined with an appropriate handle for separately manipulating the proximal and distal segments of the catheter shaft. Embodiments of such a handle—i.e., a handle for separately manipulating two sets of two deflection wires each—will be discussed in conjunction with FIGS. 50-62. First, in conjunction with FIGS. 15-49, the operation of various embodiments of a handle configured for independently manipulating a single pair of deflection wires will first be discussed to more generally illustrate various aspects of a catheter control handle.

Figure 15:
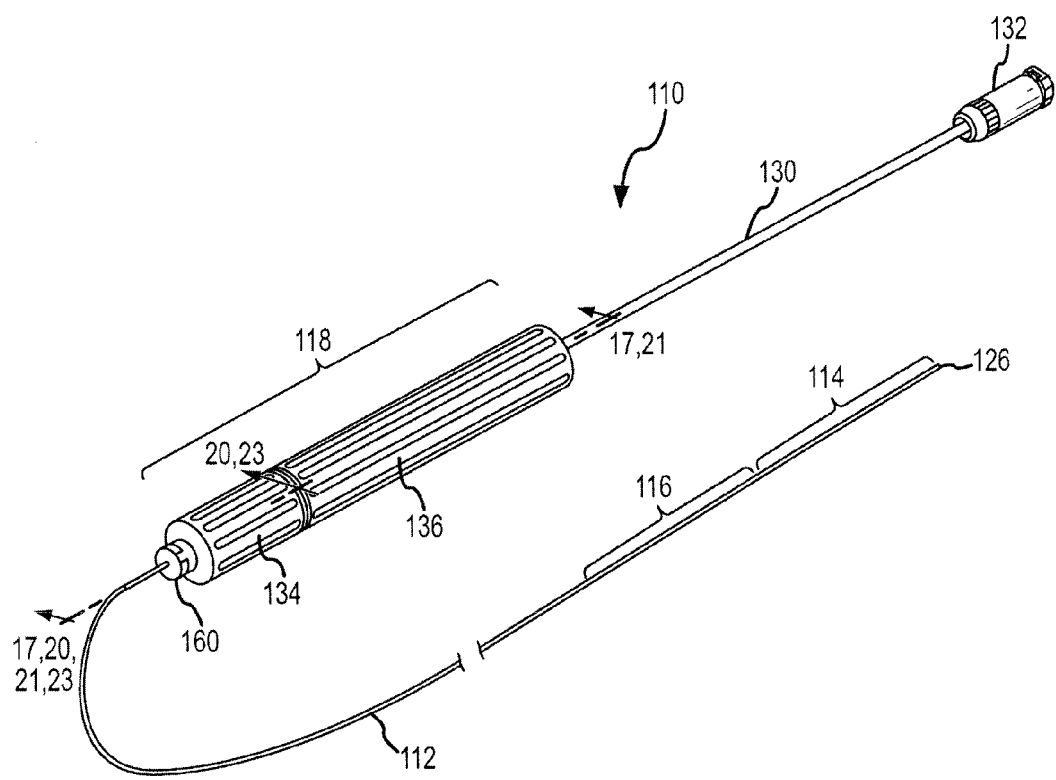
FIG. 15 is an isometric view of an embodiment of a catheter.

FIG. 15 is an isometric view of an embodiment of a catheter 110 having a control handle 118 and a flexible tubular body 112 having a proximal segment 116, a distal segment 114, and a distal end 126. As shown in FIG. 15, in one embodiment, the distal end of the handle 118 is connected to the catheter body 112 and the proximal end of the handle 118 is connected to tubing 130 that contains electrical wire and extends to an electrical connector 132. The handle 118 includes an adjusting knob 134 and a handle grip 136. As will become clear from this specification, the handle 118 of the present invention is advantageous in that it is compact and allows a user to manipulate the catheter body's extreme distal end 126 in a bi-directional manner by pivoting the adjusting knob 134 relative to the handle grip 136 in one direction or the other about the longitudinal axis of the handle 118. Furthermore, in one embodiment, the handle 118 has a lumen that runs uninterrupted from the proximal end of the handle 118 to the extreme distal end 126 of the catheter body 112. This lumen can be used, for example only, to provide contrast injection for guide wire insertion.

Figure 16:
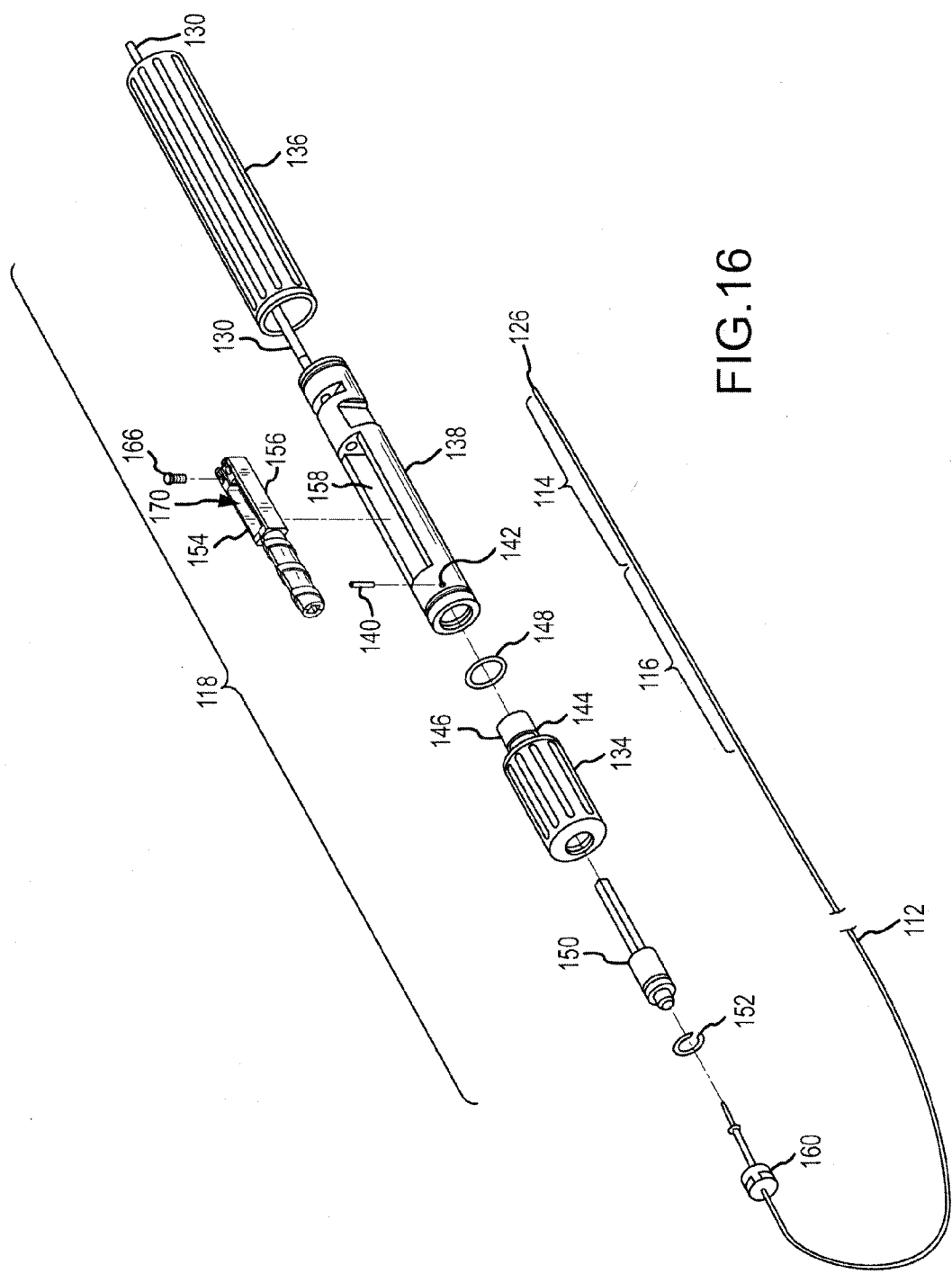
FIG. 16 is an exploded isometric view of the catheter handle shown in FIG. 15.
Figure 17:
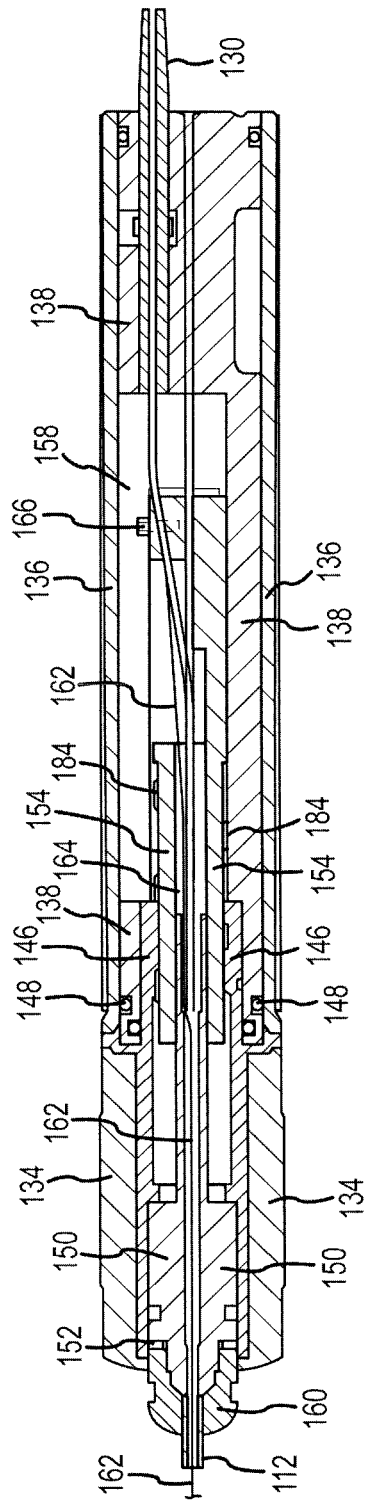
FIG. 17 is a cross-sectional view of an embodiment of the handle of FIG. 15 taken substantially along line 17-17 in FIG. 15.

For a more detailed discussion of the handle 118, reference is now made to FIGS. 16 and 17. FIG. 16 is an exploded isometric view of the handle 118 to show the various components of the handle 118. FIG. 17 is a cross-sectional view of the handle 118 taken along section line 17-17 of FIG. 15.

As shown in FIGS. 16 and 17, the adjusting knob 134 is pivotally attached to a mounting shaft (i.e., a slide base or base portion) 138 contained within the handle grip 136. To pivotally attach the knob 134 to the mounting shaft 138, a dowel pin 140 is inserted into a pinhole 142 in the distal end of the shaft 138 and mates with a groove 144 in a hub portion 146 of the knob 134. A silicone o-ring 148 exists between the hub portion 146 of the knob 134 and the distal end of the shaft 138.

As indicated in FIGS. 16 and 17, a wire guide 150 is positioned within the adjusting knob 134 and is held in place by a retaining ring 152. A right slide or member 154 and a left slide or member 156 are slideably positioned within a slot (i.e., a slide compartment) 158 in the mounting shaft 138. A catheter body-retaining nut 160 is used to secure the catheter body 112 to the distal end of the wire guide 150.

As illustrated in FIG. 17, a pair of deflection wires 162 extend from the extreme distal end 126 of the body 112, through the body 112, the wire guide 150 and a passage 164 formed between the two slides 154, 156, to a point near a proximal portion of the slides 154, 156. Each wire 162 then affixes to an individual slide 154, 156 via a retention screw 166.

Figure 18:
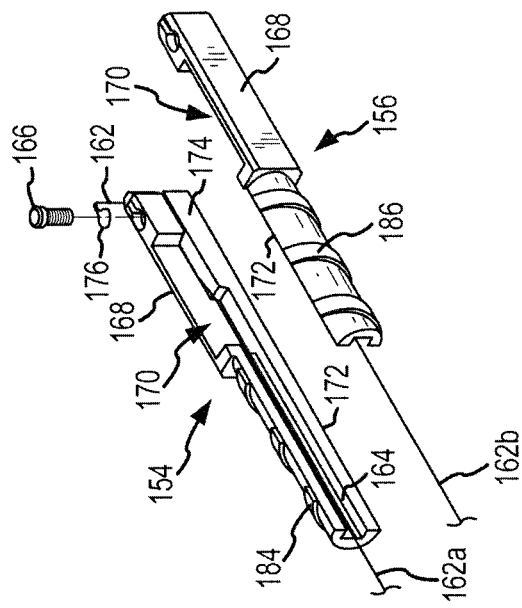
FIG. 18 is an exploded view of the right and left slides of FIG. 17 with their respective deflection wires attached.

For a more detailed discussion of the slides 154, 156 and their relationship to the deflection wires 162, reference is now made to FIG. 18, which is an isometric view of the deflection wires 162a, 162b attached to the right and left slides 154, 156. As shown in FIG. 18, the slides 154, 156, which are mirror images of each other, each have a rectangular box-like proximal portion 168 and a half-cylinder distal portion 172. Each proximal portion 168 has a generally planar outer sidewall and bottom wall. These planar surfaces slideably displace against the generally planar sides and bottom of the slot 158, which act as thrust surfaces for the slides 154, 156.

Each half-cylinder distal portion 172 is hollowed out along its longitudinal axis to form the passage 164 through which the deflection wires 162a, 162b and, as indicated in FIG. 18, the narrow proximal portion of the wire guide 150 extends when the slides 154, 156 are in the assembled handle 118. Each slide 154, 156 has a planar slide face 174 that is meant to slideably abut against the planar slide face 174 of the opposing slide 154, 156. Thus, as illustrated in FIG. 18, when the planar slide faces 174 of the slides 154, 156 abut against each other and the extreme proximal ends of each slide 154, 156 are flush with each other, the half-cylinder distal portions 172 of each slide 154, 156 combine to form a complete cylinder with a channel or passage 164 there through.

Figure 19:
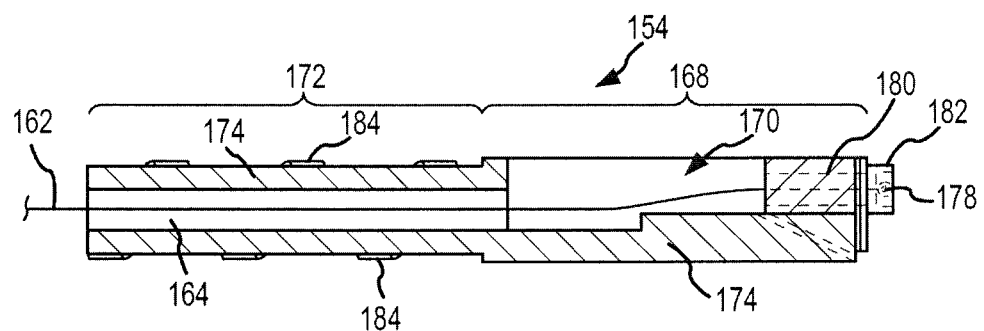
FIG. 19 is a cross-sectional view of an embodiment of a slide such as may be used in the catheter handle of FIG. 16.

As shown in FIG. 18, in one embodiment, the proximal end of each deflection wire 162a, 162b forms a loop 176 through which a retention screw 166 passes to secure the wire 162a, 162b to the proximal portion of the respective slide 154, 156. As indicated in FIG. 19, which is a side elevation of an exemplary slide 154, in one embodiment, the proximal end of each deflection wire 162 forms a knot 178. The wire 162 passes through a hollow tension adjustment screw 180 and the knot 178 abuts against the head 182 of the screw 180, thereby preventing the wire 162 from being pulled back through the screw 180. In one embodiment, the screw's longitudinal axis and the longitudinal axis of the slide 154, 156 are generally parallel. Each tension adjustment screw 180 is threadably received in the proximal end of its respective slide 154, 156. Tension in a wire 162 may be increased by outwardly threading the wire's tension adjustment screw 180. Conversely, tension in a wire 162 may be decreased by inwardly threading the wire's tension adjustment screw 180.

As can be understood from FIG. 18, in one embodiment where the wires 162a, 162b are intended to only transmit tension forces, the wires 162a, 162b may deflect or flex within an open area 170 defined in the proximal portion 168 of each slide 154, 156 when the slides 154, 156 displace distally. Similarly, as can be understood from FIG. 19, in another embodiment where the wires 162 are intended to only transmit tension forces, the wires 162 may slide proximally relative to the screw 180 when the slides 154, 156 displace distally.

As shown in FIG. 18, in one embodiment, the outer circumference of the half-cylinder distal portion 172 of the right slide 154 is threaded with a right-hand thread 184, and the outer circumference of the half-cylinder distal portion 172 of the left slide 156 is threaded with a left-hand thread 186. In one embodiment, the outer circumference of the half-cylinder distal portion 172 of the right slide 154 is threaded with a left-hand thread, and the outer circumference of the half-cylinder distal portion 172 of the left slide 156 is threaded with a right-hand thread.

Figure 20:
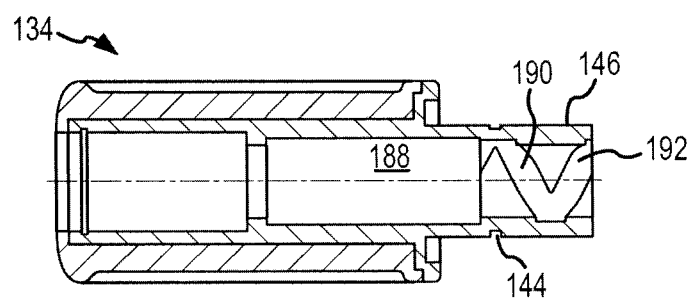
FIG. 20 is a cross-sectional view of the adjusting knob of the catheter of FIG. 15, taken substantially along line 20-20 in FIG. 15.

For a better understanding of the relationship of the slide threads 184, 186 to the rest of the handle 118, reference is now made to FIG. 20, which is a longitudinal sectional elevation of the adjusting knob 134 taken along section line 20-20 of FIG. 15. As indicated in FIG. 20, a cylindrical hole or shaft 188 passes through the knob 134 along the knob's longitudinal axis. In the hub portion 146 of the knob 134, the inner circumferential surface of the shaft 188 has both right hand threads 190 and left hand threads 192. These internal threads 190, 192 of the knob 134 mate with the corresponding external threads 184, 186 of the slides 154, 156. More specifically, the right internal threads 190 of the knob 134 mate with the right external threads 184 of the right slide 154, and the left internal threads 192 of the knob 134 mate with the left external threads 186 of the left slide 156.

Thus, as can be understood from FIGS. 16, 17, 18, and 20, in one embodiment, as the knob 134 is rotated clockwise relative to the longitudinal axis of the handle 118, the internal and external right threads 190, 184 engage and the internal and external left threads 192, 186 engage, thereby causing simultaneous opposed displacement of the right and left slides 154, 156 longitudinally within the slot 158 in the handle 118. Specifically, because of the threading arrangement of the knob 134 and the slides, 154, 156, the right slide 154 moves distally within the slot 158 and the left slide 156 moves proximally within the slot 158 when the knob 134 is rotated clockwise relative to the handle grip 136 of the handle 118. Conversely, when the knob 134 is rotated in a counter-clockwise manner relative to the handle grip 136 of the handle 118, the right slide 154 moves proximally within the slot 158 and the left slide 156 moves distally within the slot 158.

As can be understood from FIGS. 18 and 20, when the knob 134 is rotated such that the right slide 154 is urged distally and the left slide 156 is urged proximally, the deflection wire 162a connected to the right slide 154 is placed into compression and the deflection wire 162b connected to the left slide 156 is placed into tension. In an embodiment, this causes the proximal segment 116, distal segment 114, and/or extreme distal end 126 of the catheter body 112 to deflect in a first direction. Conversely, when the knob 134 is rotated such that the right slide 154 is urged proximally and the left slide 156 is urged distally, the deflection wire 162a connected to the right slide 154 is placed into tension and the deflection wire 162b connected to the left slide 156 is placed into compression. This causes the proximal segment 116, distal segment 114, and/or extreme distal end 126 of the catheter body 112 to deflect in a second direction that is opposite the first direction.

The control handle 118 of the present invention as described has several advantages. First, the handle 118 is compact and may be operated with a single hand. Second, the threaded slides 154, 156 and knob 134 allow a physician to make fine, controlled adjustments to the bend in the distal end 126 of the catheter body 112. Third, once the knob 134 is rotated so as to cause a bend in the distal end 126 of the catheter body 112, the threads 184, 186, 190, 192 interact to maintain the bend without requiring any action on the physician's part. Fourth, because the slides 154, 156 simply displace distally and proximally along the longitudinal axis of the handle 118, they are less likely to permanently deform the wires 38 as compared to the wire displacement mechanisms in some prior art handles. Fifth, the threads 184, 186, 190, 192 are mechanically advantageous in that they provide increased deflection wire travel and reduced actuation effort for the physician, as compared to some prior art handles.

While FIGS. 16-20 depict an embodiment where the slides 154, 156 have external threads 184, 186 and the knob 134 has internal threads 190, 192, in other embodiments the threading arrangement is reversed. For a discussion of one such embodiment, reference is made to FIGS. 21-23. FIG. 21 is a longitudinal sectional elevation of the handle $118_1$ taken along section line 21-21 of FIG. 15. FIG. 22 is a side elevation of an exemplary slide employed in the embodiment depicted in FIG. 21. FIG. 23 is a longitudinal sectional elevation of the adjusting knob taken along section line 23-23 of FIG. 15.

A comparison of the embodiment depicted in FIGS. 21-23 to the embodiment depicted in FIGS. 17, 19 and 20 reveals that the two embodiments are generally the same, except as will be described in the following discussion of FIGS. 21-23. Reference numbers utilized in FIGS. 21-23 pertain to the same or similar features identified by the same reference numbers in FIGS. 17, 19 and 20, though successive embodiments of features are distinguished with subscript.

As shown in FIG. 21, the adjusting knob $134_1$ is pivotally attached to a mounting shaft (i.e., a slide base or base portion) $138_1$ contained within the handle grip $136_1$. A wire guide $150_1$ is positioned within the adjusting knob $134_1$. Like the embodiment depicted in FIG. 16, the embodiment illustrated in FIG. 21 includes a right slide or member $154_1$ and a left slide or member $156_1$ that are slideably positioned within a slot (i.e., a slide compartment) $158_1$ in the mounting shaft $138_1$.

As can be understood from FIG. 22, the slides $154_1$, $156_1$, which are mirror images of each other, each have a rectangular box-like proximal portion $168_1$ and a distal portion $172_1$ that may be rectangular or half-cylindrical. Each proximal portion $168_1$ has a generally planar outer sidewall and bottom wall. These planar surfaces slideably displace against the generally planar sides and bottom of the slot $158_1$, which act as thrust surfaces for the slides $154_1$, $156_1$.

Each distal portion $172_1$ is hollowed out to form half of a cylindrical passage $164_1$ that is created when the slides $154_1$, $156_1$ are abutted against each other in a side-by-side relationship. Thus, each distal portion $172_1$ of each slide $154_1$, $156_1$ includes an inner circumferential surface, which when combined with the inner circumferential surface of the other slide $154_1$, $156_1$, defines the cylindrical passage $164_1$.

As indicated in FIG. 22, in one embodiment, the inner circumferential surface of the right slide $154_1$ is threaded with a right-hand thread $184_1$. Similarly, as can be understood from FIG. 22, the inner circumferential surface of the left slide $156_1$ is threaded with a left-hand thread $186_1$. Thus, the distal portion $172_1$ of each slide $154_1$, $156_1$ is equipped with internal threads. In another embodiment, the inner circumferential surface of the right slide $154_1$ is threaded with a left-hand thread $186_1$. Similarly, the inner circumferential surface of the left slide $156_1$ is threaded with a right-hand thread $184_1$.

As indicated in FIG. 23, the knob $134_1$ includes an outer hub $146a_1$ surrounding an inner hub $146b_1$. A space 195 exists between, and is defined by, the inner and outer hubs $146a_1$, $146b_1$. The space 195 is adapted to receive the distal ends $172_1$ of each slide $154_1$, $156_1$. The outer circumferential surface of the inner hub $146b_1$ has both right hand threads $190_1$ and left hand threads $192_1$. These external threads $190_1$, $192_1$ of the knob $134_1$ mate with the corresponding internal threads $184_1$, $186_1$ of the slides $154_1$, $156_1$. More specifically, the right external threads $190_1$ of the knob $134_1$ mate with the right internal threads $184_1$ of the right slide $154_1$, and the left external threads $192_1$ of the knob $134_1$ mate with the left internal threads $186_1$ of the left slide $156_1$.

As can be understood from FIG. 21, in one embodiment, as the knob $134_1$ is rotated clockwise relative to the longitudinal axis of the handle $118_1$, the internal and external right threads $184_1$, $190_1$ engage and the internal and external left threads $186_1$, $192_1$ engage, thereby causing simultaneous opposed displacement of the right and left slides $154_1$, $156_1$ longitudinally within the slot $158_1$ in the handle $118_1$. Specifically, because of the threading arrangement of the knob $134_1$ and the slides $154_1$, $156_1$, the right slide $154_1$ moves distally within the slot $158_1$ and the left slide $156_1$ moves proximally within the slot $158_1$ when the knob $134_1$ is rotated clockwise relative to the handle grip $136_1$ of the handle $118_1$. Conversely, when the knob $134_1$ is rotated in a counterclockwise manner relative to the handle grip $136_1$ of the handle $118_1$, the right slide $154_1$ moves proximally within the slot $158_1$ and the left slide $156_1$ moves distally within the slot $158_1$.

As can be understood from FIG. 21, when the knob $134_1$ is rotated such that the right slide $154_1$ is urged distally and the left slide $156_1$ is urged proximally, the deflection wire 162 connected to the right slide $154_1$ is placed into compression and the deflection wire 162 connected to the left slide $156_1$ is placed into tension. This causes the extreme distal end 126 of the catheter body 112 to deflect in a first direction. Conversely, when the knob $134_1$ is rotated such that the right slide $154_1$ is urged proximally and the left slide 156 is urged distally, the deflection wire 162 connected to the right slide $154_1$ is placed into tension and the deflection wire 162 connected to the left slide $156_1$ is placed into compression. This causes the extreme distal end 126 of the catheter body 112 to deflect in a second direction that is opposite the first direction.

Figure 24:
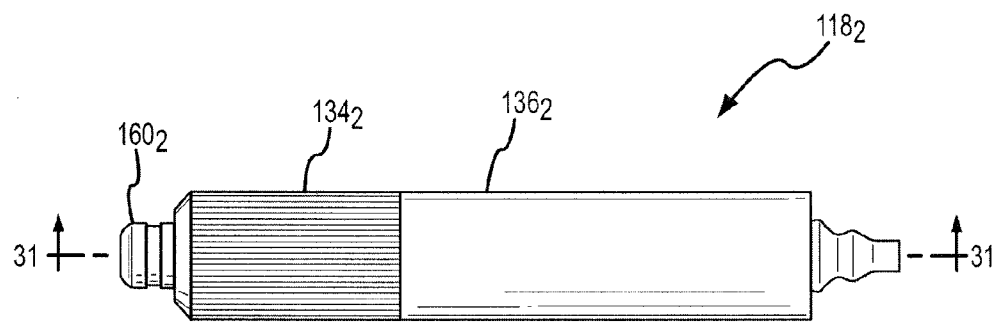
FIG. 24 is a side view of an embodiment of a catheter handle.
Figure 25:
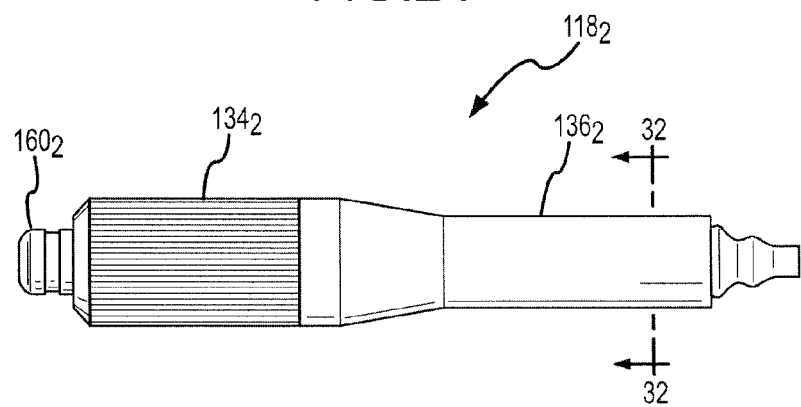
FIG. 25 is a side view of the catheter handle depicted in FIG. 24.
Figure 26:
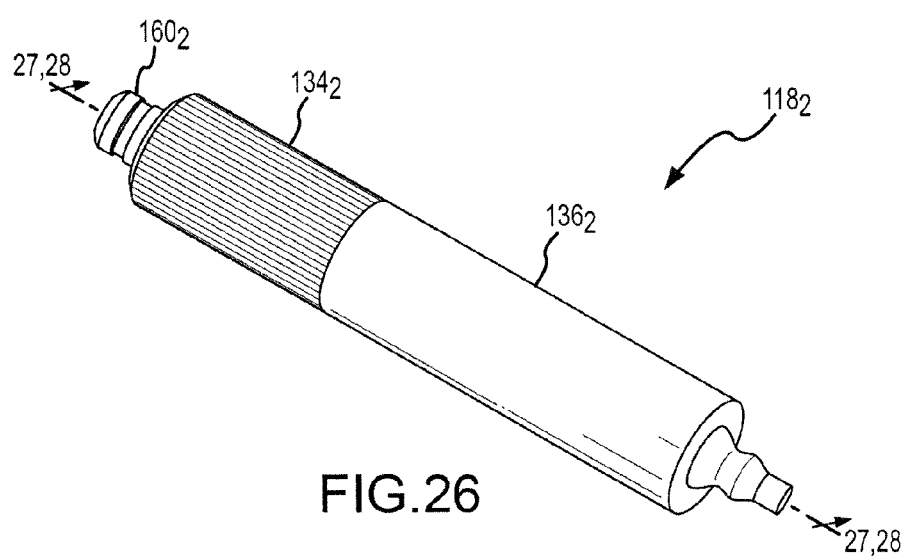
FIG. 26 is an isometric view of the catheter handle depicted in FIG. 24.

For a detailed discussion of another embodiment of a catheter handle $118_2$, reference is now made to FIGS. 24-26. FIG. 24 is a plan view of the handle $118_2$. FIG. 25 is a side elevation of the handle $118_2$. FIG. 26 is an isometric view of the distal end of the handle $118_2$.

As shown in FIGS. 24-26, the handle $118_2$ includes an adjusting knob $134_2$ on its distal end and a handle grip $136_2$ on its proximal end. As can be understood from FIGS. 24-26, in one embodiment, the knob $134_2$ has a generally circular cross-section and the handle grip $136_2$ has a generally oval cross-section. In one embodiment, both the knob $134_2$ and the handle grip $136_2$ have generally circular cross-sections. The oval cross-section of the handle grip $136_2$ is advantageous because it provides the physician with a tactile indication of the catheter's rotational position.

For a more detailed discussion of the components of the handle $118_2$, reference is now made to FIG. 27, which is a longitudinal sectional plan view of the handle $118_2$ taken along section line 27-27 of FIG. 26. As shown in FIG. 27, an o-ring $148_2$ is located between the handle grip $136_2$ and a groove in the knob $134_2$. The knob $134_2$ is pivotally affixed to the handle grip $136_2$ via a rotating retaining-ring 189 that resides within grooves in both the knob and the handle grip $136_2$.

As illustrated in FIG. 27, a catheter body-retaining nut $160_2$ is threadably affixed to the distal end of a wire guide $150_2$ that extends along the axial center of the knob $134_2$. As indicated in FIG. 27 and more clearly shown in FIG. 28, which is a longitudinal sectional plan view of the knob $134_2$ taken along section line 28-28 in FIG. 26, a cylindrical hole or shaft $188_2$ passes through the knob $134_2$ along the knob's longitudinal axis. The inner circumferential surface of the shaft $188_2$ has both right hand threads $190_2$ and left hand threads $192_2$ that extend towards the distal end of the knob $134_2$ from a hub portion $146_2$ of the knob $134_2$. As shown in FIG. 28, in one embodiment, the knob $134_2$ is a singular integral piece.

Figure 29:
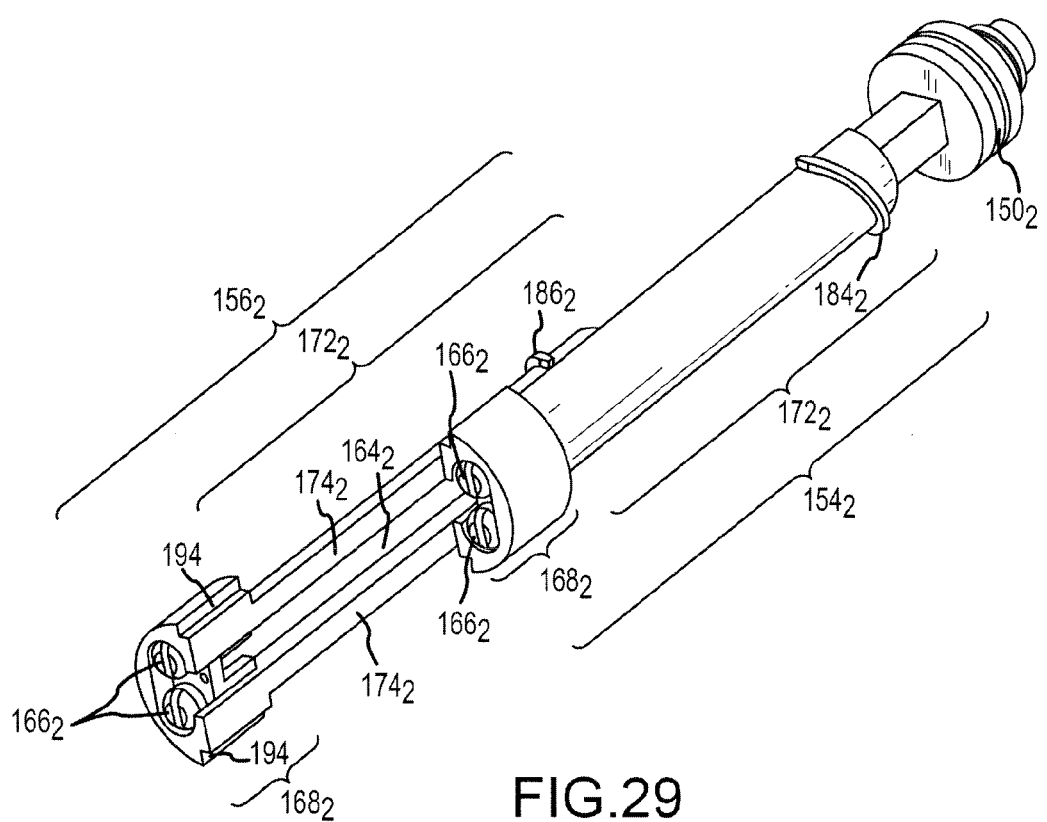
FIG. 29 is a right side isometric view of an embodiment of two slides, such as may be used in the catheter handle of FIG. 26, disposed about a wire guide.
Figure 30:
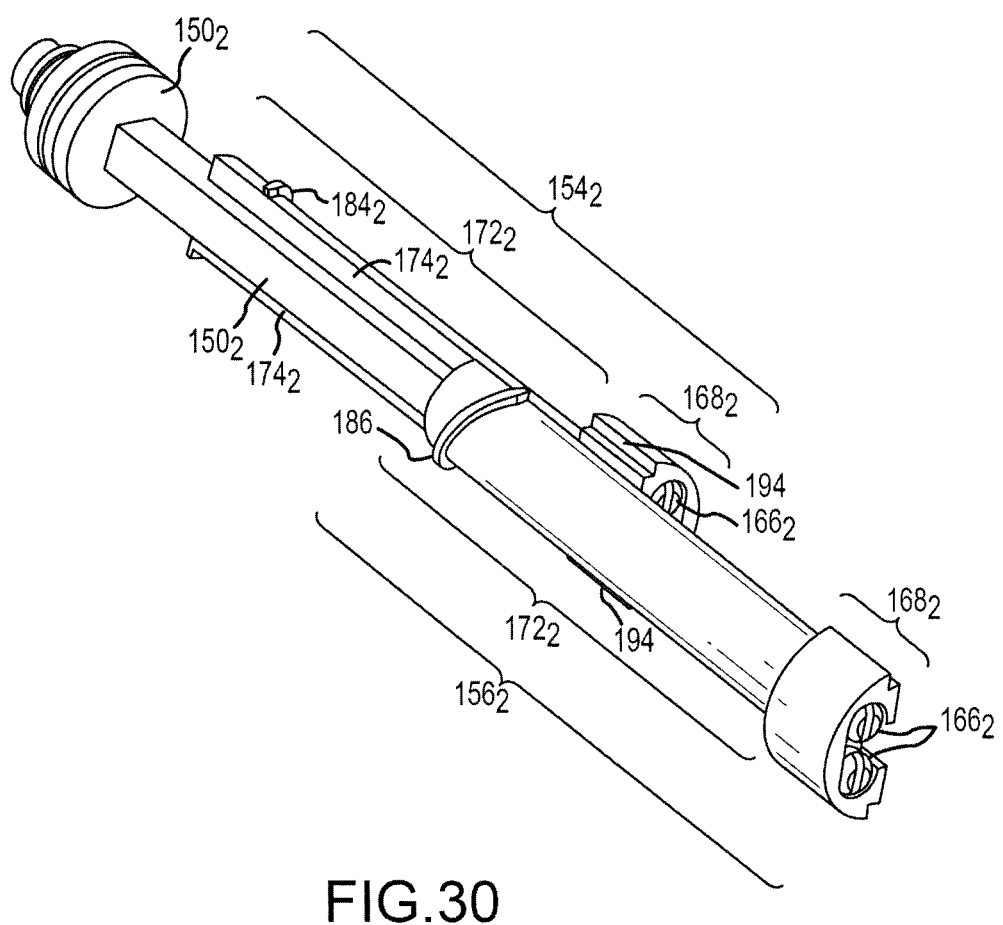
FIG. 30 is a left side isometric view of the slides of FIG. 29, disposed about a wire guide.

As indicated in FIG. 27, a right slide $154_2$ and a left slide $156_2$ are longitudinally displaceable within the handle $118_2$ and about the proximal end of the wire guide $150_2$. As shown in FIGS. 29 and 30, which are, respectively, a right side isometric view of the slides $154_2$, $156_2$ displaced about the wire guide $150_2$ and a left side isometric view of the slides $154_2$, $156_2$ displaced about the wire guide $150_2$, each slide $154_2$, $156_2$ has a planar slide face $174_2$ that abuts and slideably displaces against the slide face $174_2$ of the opposed slide $154_2$, $156_2$. Also, each slide $154_2$, $156_2$ has a channel that combines with the channel of the opposed slide $154_2$, $156_2$ to form a passage $164_2$ through which the proximal end of the wire guide $150_2$ passes as the slides $154_2$, $156_2$ displace about the wire guide $150_2$. As shown in FIG. 27, the passage $164_2$ formed by the channels also provides a pathway along which the deflection wires 162a, 162b (represented by dashed lines in FIG. 27) travel from a proximal portion of the slides $154_2$, $156_2$, through the wire guide $150_2$, and onward to the extreme distal end 126 of the catheter body 112.

As indicated in FIGS. 29 and 30, each slide $154_2$, $156_2$ has a half-cylinder distal portion $172_2$ and a shorter and wider half-cylinder proximal portion $168_2$. The right slide $154_2$ has a right-handed thread $184_2$ on its distal portion $172_2$. Similarly, the left slide $156_2$ has a left-handed thread $186_2$ on its distal portion $172_2$. Thus, as can be understood from FIG. 27, when the knob $134_2$ is rotated in a clockwise direction relative to the handle grip $136_2$ the right handed threads $190_2$ within the knob $134_2$ engage the right handed threads $184_2$ of the right slide $154_2$, and the left handed threads $192_2$ within the knob $134_2$ engage the left handed threads $186_2$ of the left slide $156_2$. As a result, the right slide $154_2$ is distally displaced within the handle $118_2$ and the left slide $156_2$ is proximally displaced within the handle $118_2$. Accordingly, the deflection wire 162a attached to the right slide $154_2$ is pushed (i.e., subjected to a compressive force) and the deflection wire 162b attached to the left slide $156_2$ is pulled (i.e., subjected to a tension force). Conversely, if the knob is rotated counter-clockwise, the opposite displacement of the slides $154_2$, $156_2$ and deflection wires 162a, 162b will occur.

As indicated in FIG. 27, each deflection wire 162a, 162b is attached to the proximal portion $168_2$ of its respective slide $154_2$, $156_2$ via retention screws $166_2$. The retention screws, which are more clearly illustrated in FIGS. 29 and 30, are threadably mounted in the proximal portions $168_2$.

As shown in FIGS. 29 and 30, each half-cylindrical proximal portion $168_2$ of a slide $154_2$, $156_2$ has an upper and lower planar notch 194 adjacent their respective planar slide faces $174_2$. The function of these notches 194 may be understood by referring to FIGS. 31 and 32.

Figure 31:
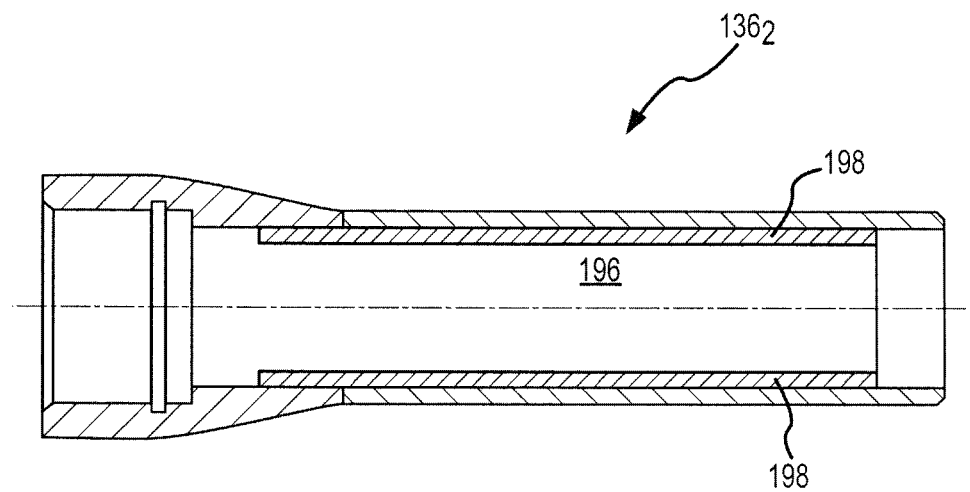
FIG. 31 is a cross-sectional view of the handle grip of FIG. 24, taken substantially along line 31-31 in FIG. 24.
Figure 32:
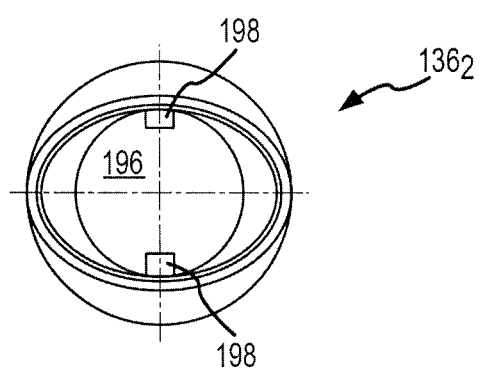
FIG. 32 is a cross-sectional view of the handle grip of FIG. 25 taken substantially along line 32-32 in FIG. 25.

FIG. 31 is a longitudinal section elevation of the handle grip $136_2$ taken along section line 31-31 in FIG. 24. FIG. 32 is a latitudinal section elevation of the handle grip $136_2$ taken along section line 32-32 in FIG. 25. As shown in FIGS. 28 and 29, the handle grip $136_2$ is one integral piece having an interior cylindrical void 196 in which the proximal portions $168_2$ of the slides $154_2$, $156_2$ may displace as indicated in FIG. 27.

As shown in FIGS. 31 and 32, upper and lower ribs 198 extend from the walls that form the interior cylindrical void 196. The ribs 198 run longitudinally along a substantial portion of the cylindrical void's length. As can be understood from FIGS. 29-32, the upper planar notches 194 on the proximal portions $168_2$ of the slides $154_2$, $156_2$ interface with, and displace along, the upper rib 198 as the slides $154_2$, $156_2$ displace within the cylindrical void 196. Similarly, the lower planar notches 194 on the proximal portions $168_2$ of the slides $154_2$, $156_2$ interface with, and displace along, the lower rib 198 as the slides $154_2$, $156_2$ displace within the cylindrical void 196. Thus, the ribs 198 act as thrust surfaces for the slides $154_2$, $156_2$.

Figure 33:
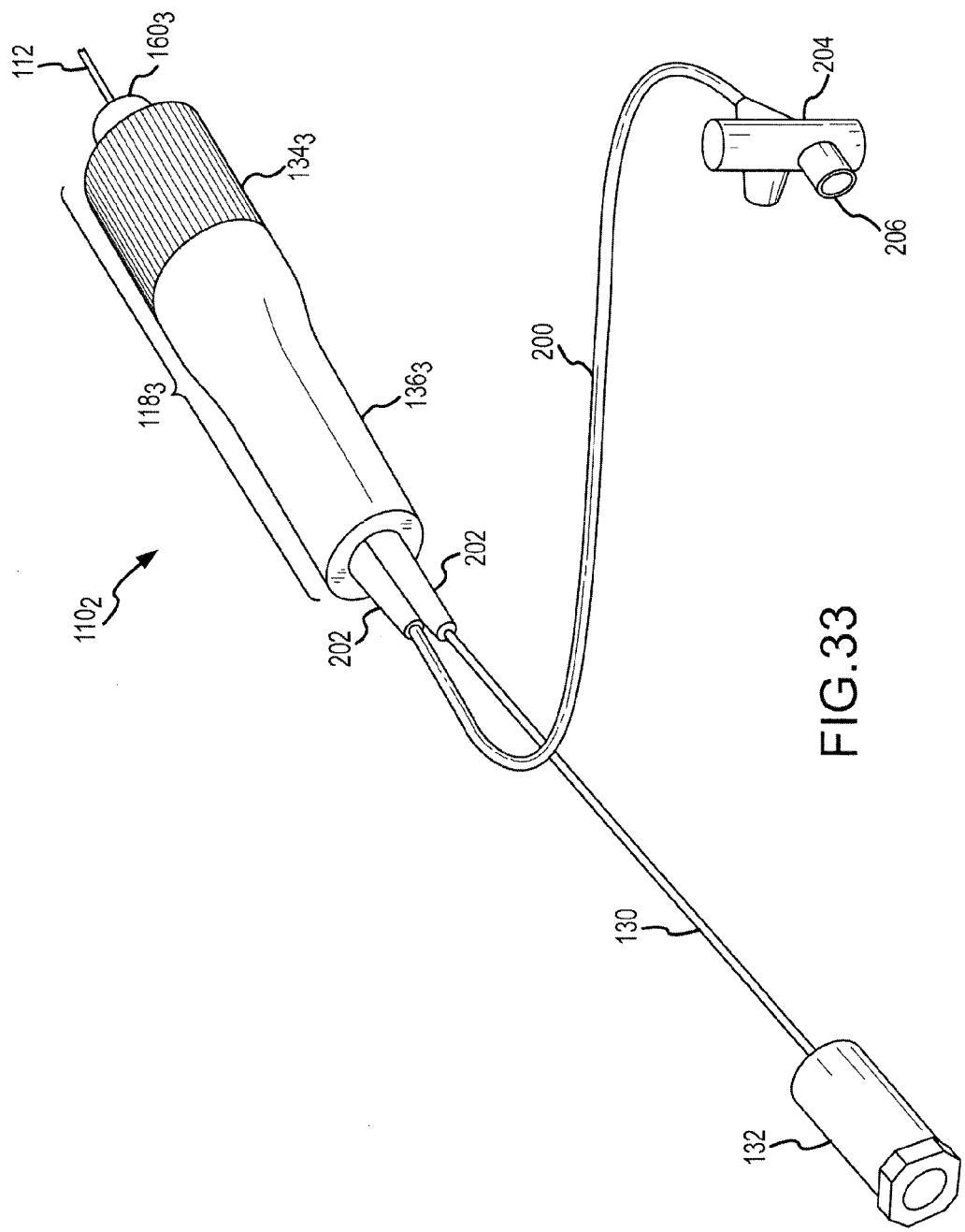
FIG. 33 is an isometric view of an embodiment of a control handle for a catheter.

For a detailed discussion of another embodiment of the handle $118_2$ depicted in FIGS. 24-32, reference is now made to FIG. 33. FIG. 33 is an isometric view of the distal end of a control handle $118_3$ for a catheter $110_2$ wherein the handle $118_3$ and catheter body 112 have a through lumen 200. As shown in FIG. 33, in one embodiment, the lumen 200 and the electrical wire tube 130, which extends to the electrical connector 132, pass through strain reliefs 202 and into the proximal end of the handle grip $136_3$. In one embodiment, the lumen 200 terminates at its proximal end with a stopcock 204. In one embodiment, the stopcock 204 has a hemostasis seal 206 that can be utilized for guide wire insertion. While a long flexible length of lumen 200, as depicted in FIG. 33, provides motion isolation while inserting contrast from a syringe, in one embodiment, the lumen 200 does not extend from the handle grip $136_3$. Instead, the stopcock 204 or luer fitting is simply attached to the lumen 200 where it exits the proximal end of the handle grip $136_3$.

Figure 34:
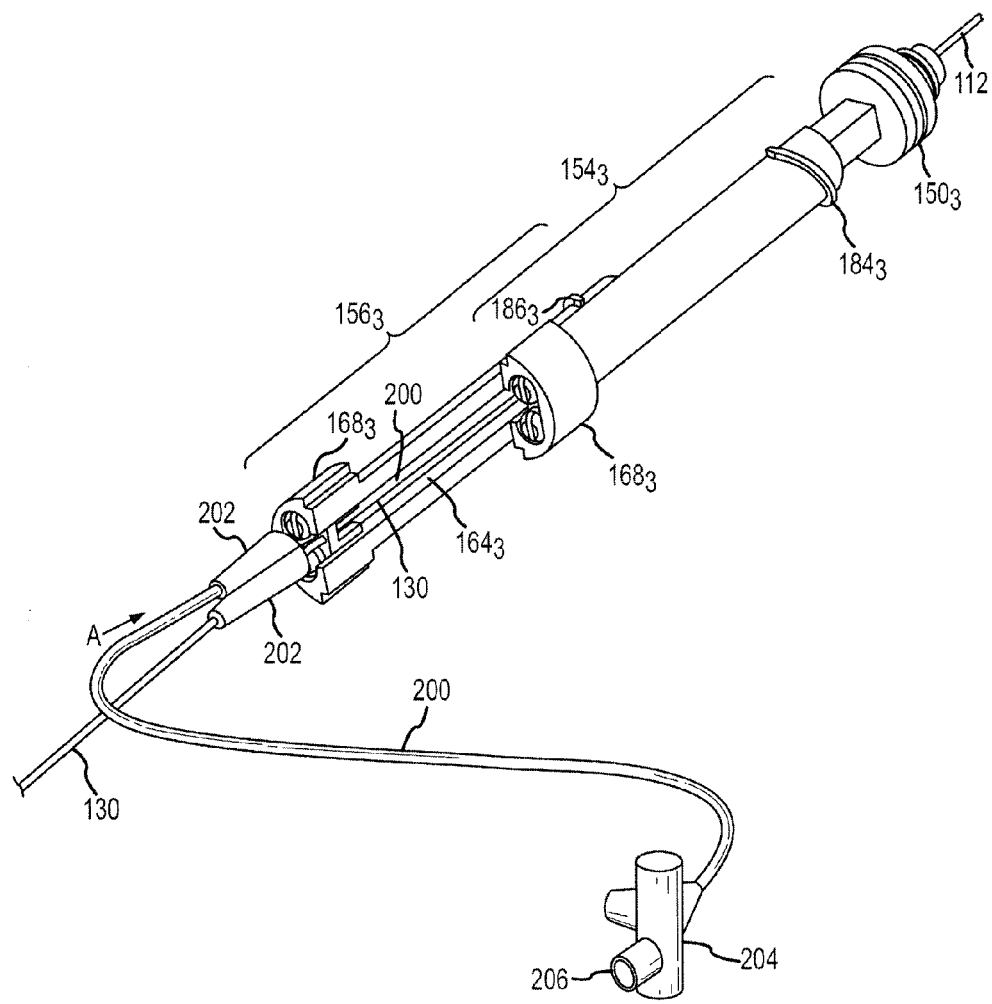
FIG. 34 is an isometric view of a portion of the interior of the control handle of FIG. 33.
Figure 35:
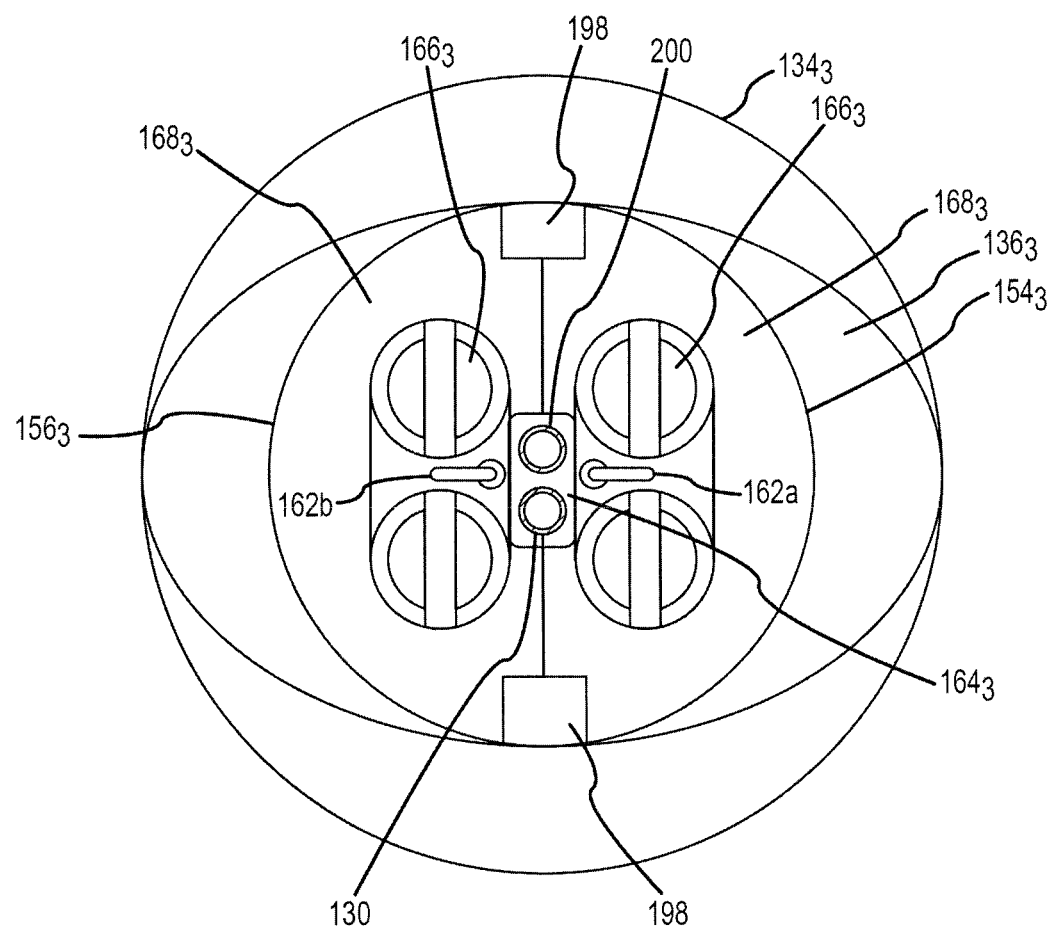
FIG. 35 is a proximal end view of the interior shown in FIG. 34 as viewed from the perspective of arrow A in FIG. 34.
Figure 36:
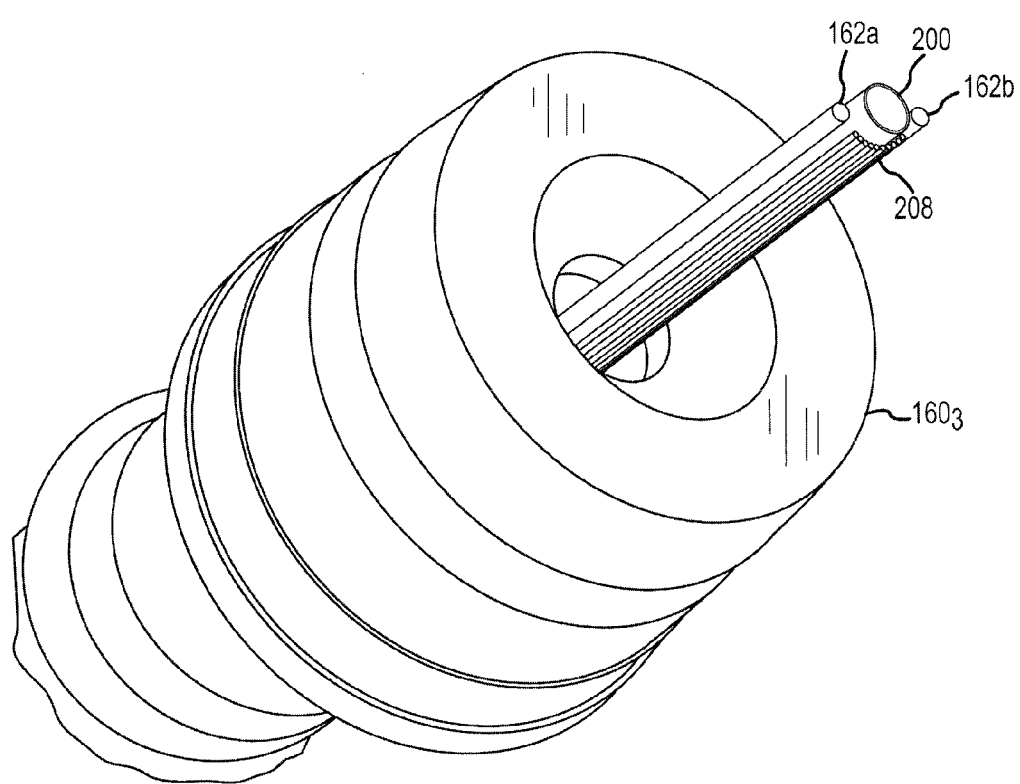
FIG. 36 is an isometric view of the distal end of the control handle of FIG. 33.

For a better understanding of the path of the lumen 200, reference is now made to FIGS. 34-36. FIG. 34 is an isometric view of the slides $154_3$, $156_3$, the wire guide $150_3$, the wire tubing 130, and the lumen 200 illustrating the path the lumen 200 takes through the handle $118_3$. FIG. 35 is an elevation view of the extreme proximal end surfaces of the slides $154_3$, $156_3$ as viewed from arrow A in FIG. 34 and illustrating the path the lumen 200 and wire tubing 130 take into the passage formed by the channels $164_3$ of the slides $154_3$, $156_3$. FIG. 36 is an isometric view of the lumen 200, deflection wires 162a, 162b, and electrical wires 208 of the wire tube 130 exiting the catheter body-retaining nut $160_3$ on the distal end of the handle $118_3$.

As shown in FIGS. 34 and 35, the lumen 200 and the wire tubing 130 pass through their respective reliefs 202 and into the passage formed by the channels $164_3$ in each slide $154_3$, $156_3$. In one embodiment, soon after the wire tubing 130 and the lumen 200 enter the passage $164_3$, the wires 208 of the wire tubing 130 exit the wire tubing 130 and are dispersed about the outer circumference of the lumen 200 as depicted in FIG. 36.

As illustrated in FIG. 34, in another embodiment, after the wire tube 130 and lumen 200 enter the passage 164$_3$, the wire tube 130 and the lumen 200 continue on their pathway to the distal end 126 of the catheter body 112 by passing, in a side-by-side arrangement, through the remainder of the passage 164$_3$ formed into the slides 154$_3$, 156$_3$ and into an internal passage that extends along the longitudinal axis of the wire guide 150$_3$. Near the end of the wire guide 150$_3$, the wire 208 exists the wire tube 130. The wire 208, lumen 200 and deflection wires 162a, 162b then pass into the catheter by exiting the catheter body-retaining nut 160$_3$ of the handle as indicated in FIG. 36.

Figure 37:
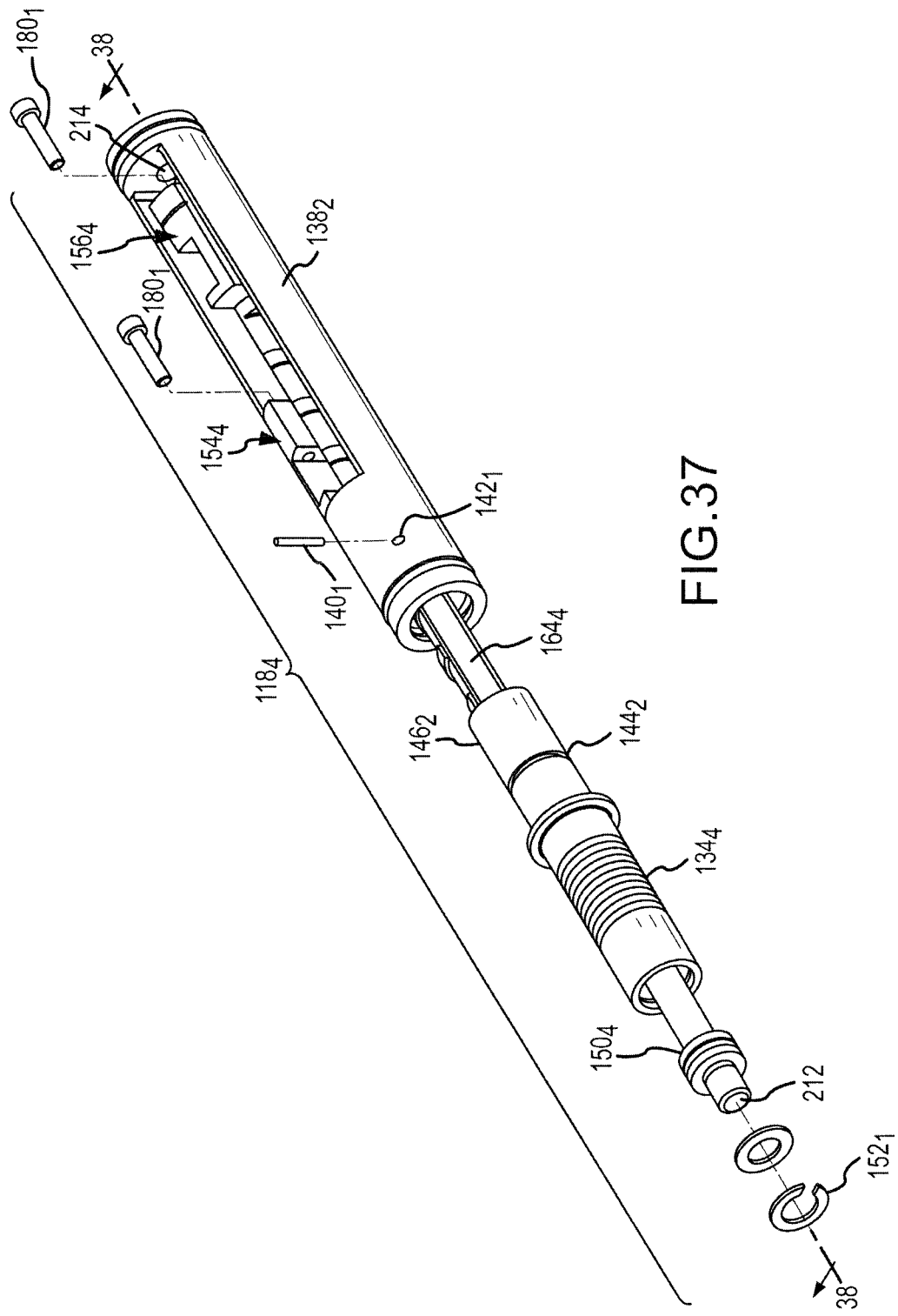
FIG. 37 is an exploded view of an embodiment of a catheter control handle.

For a detailed discussion of another embodiment of the handle 118, reference is now made to FIG. 37, which is an isometric view of the handle 118$_4$ exploded to show its various components. As can be understood from FIG. 37, the features of the handle 118$_4$ depicted in FIG. 37 are similar to the features of the handle 118 depicted in FIG. 16, except the handle 118$_4$ depicted in FIG. 37 is configured to have a relatively large, generally uniform in diameter, pathway extend the full length of the handle 118$_4$ (i.e., from the distal opening 212 in the wire guide 150$_4$, through the passage 164$_4$ defined in the slides 154$_4$, 156$_4$ and through an exit hole 214 in the proximal end of the shaft 138$_2$).

The configuration of the handle 118$_4$ that allows a relatively large generally uniform in diameter pathway to pass through the length of the handle 118$_4$, as depicted in FIG. 37, is more clearly shown in FIG. 38, which is a longitudinal sectional elevation taken along section line 38-38 in FIG. 37. As illustrated in FIG. 38, in one embodiment, the pathway 210, which includes the passage through the wire guide 150$_4$ and the passage 164$_4$ through the slides 154$_4$, 156$_4$, is large enough that the catheter body 112 itself may pass through the pathway 210 and be connected to the proximal end of the shaft 138$_2$ at the exit hole 214. Thus, in one embodiment, to prevent the catheter body 112 from rotating with the adjusting knob 134$_4$, the catheter body 112 is affixed to the shaft 138$_2$ at the exit hole 214. In one embodiment, the catheter body 112 runs the full length of the handle 118$_4$ as depicted in FIG. 38, except the body 112 is affixed to the wire guide 150$_4$ at or near the distal opening 212. In other embodiments, the catheter body 112 is affixed to both the wire guide 150$_4$ at or near the distal opening 212 and the shaft 138$_2$ at the exit hole 214.

As can be understood from FIG. 38 and as more clearly depicted in FIG. 39, which is an isometric view of the slides 154$_4$, 156$_4$ oriented to show their portions of the passage 164$_4$ and their planar slide faces 174$_3$, the passage 164$_4$ is large enough in diameter to displace over the outer diameter of the wire guide 150$_4$. As shown in FIGS. 38 and 39, a catheter body passage 218 passes through the proximal portion 168$_4$ of each slide 154$_4$, 156$_4$, thereby allowing the slides 154$_4$, 156$_4$ to displace back and forth over the outer surface of the catheter body 112.

As indicated in FIG. 38, in one embodiment, the catheter body 112 has an opening 220 in its wall that allows the wires 162 to exit the body 112 and connect to the slides 154$_4$, 156$_4$. In one embodiment, the wires 162 connect to the slides 154$_4$, 156$_4$ via tension adjustment screws 180$_1$ as previously discussed.

Due to the configuration of the slides 154$_4$, 156$_4$, the wire guide 150$_4$ and the shaft 138$_2$, the catheter body 112 may run uninterrupted the full length of the handle 118$_4$. As a result, electrical wiring 208 (see FIG. 36) and a lumen 200 may be routed the full length of the handle 118$_4$ by way of the body 112.

Figure 40:
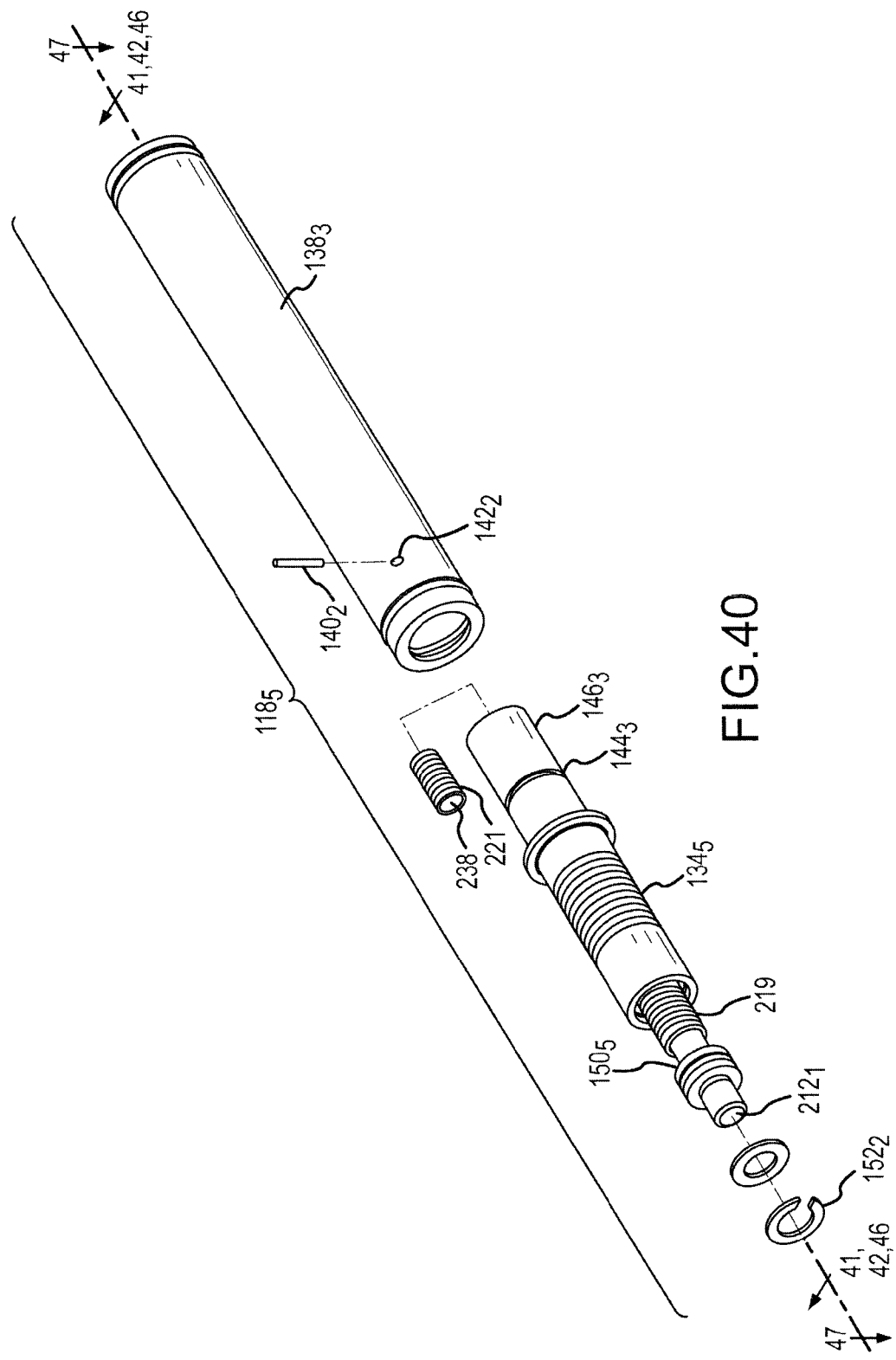
FIG. 40 is an exploded view of an embodiment of a catheter control handle.
Figure 41:
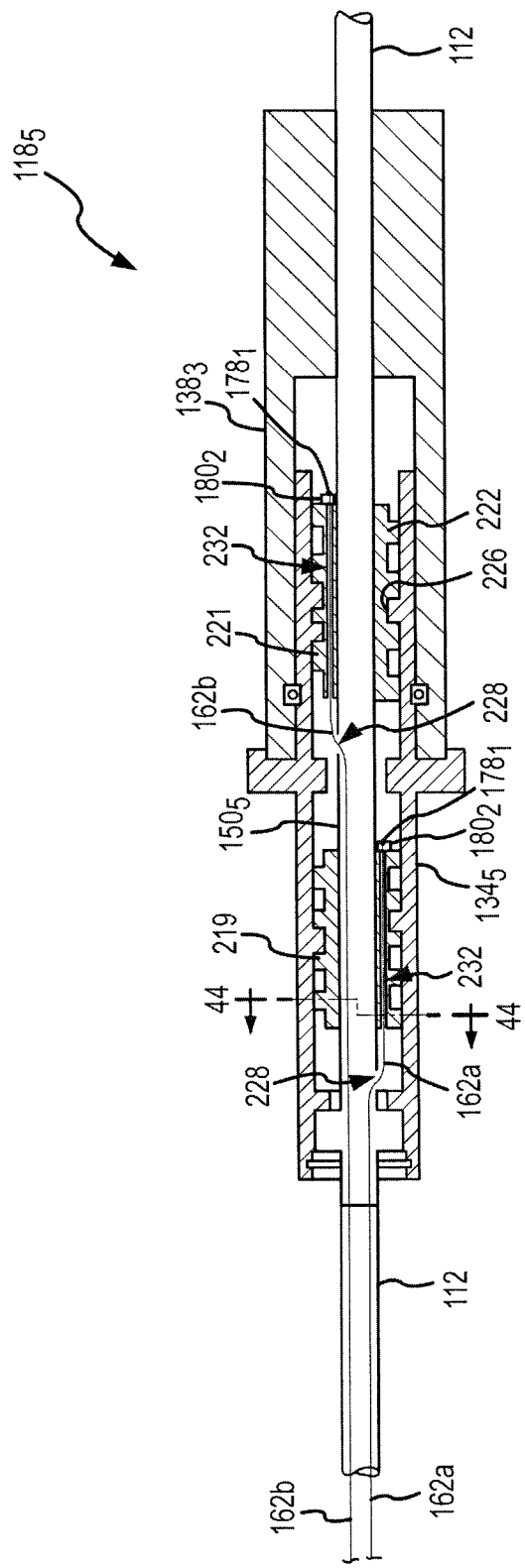
FIG. 41 is a cross-sectional view of the catheter handle of FIG. 40, taken substantially along line 41-41 of FIG. 40.

For a detailed discussion of another embodiment of the handle 118 of the present invention, reference is now made to FIGS. 40 and 41. FIG. 40 is an isometric view of the handle 118$_5$ exploded to show its various components. FIG. 41 is a longitudinal sectional elevation of the handle 118$_5$ taken along section line 41-41 of FIG. 40. Generally speaking, the features of the handle 118$_5$ depicted in FIGS. 40 and 41 are similar to the features of the handle 118$_4$ depicted in FIG. 37, except the two embodiments employ different slider arrangements. For example, the embodiments depicted in FIGS. 15-39 employ parallel slides or members 154, 156 (i.e., the slides 154, 156 exist within the handle 118 in a parallel or side-by-side arrangement). As will be understood from FIGS. 40 and 41 and the following Figures, in the embodiment of the handle 118$_5$ depicted in FIGS. 40 and 41, the slides or members 219, 221 exist within the adjustment knob 134$_5$ in a series arrangement (i.e., the slides 219, 221 are not parallel or side-by-side to each other, but are oriented end-to-end along a longitudinal axis of the handle 118$_5$).

As shown in FIGS. 40 and 41, the adjusting knob 134$_5$ is pivotally coupled to the distal end of the mounting shaft (i.e., base portion) 138$_3$. The wire guide 150$_5$ extends through the center of the adjusting knob 134$_5$ and the mounting shaft 138$_3$. The catheter body 112 is coupled to the distal end of the wire guide 150$_5$ and, in one embodiment, extends through the wire guide 150$_5$ and out of the proximal end of the mounting shaft 138$_3$.

As shown in FIGS. 40 and 41, a distal slide 219 is located in a distal portion of the adjusting knob 134$_5$, and a proximal slide 221 is located in a proximal portion (i.e., hub portion 146$_3$) of the adjusting knob 134$_5$. As illustrated in FIG. 41, the outer surface of each slide 219, 221 has threads 222 that mate with threads 226 on an interior surface of the adjusting knob 134$_5$.

As illustrated in FIG. 41, each deflection wire 162a, 162b travels along the interior of the wire guide 150$_5$ until it exits the wire guide 150$_5$ at a hole 228 in the sidewall of the wire guide 150$_5$. Each deflection wire 162a, 162b then extends to the slide 219, 221 to which the deflection wire 162a, 162b is attached. In one embodiment, in order to attach to a slide 219, 221, a deflection wire 162a, 162b passes through a passage 232 in the slide 219, 221 and attaches to a hollow tension adjustment screw 180$_2$ via a knot 178$_1$ as previously described.

Figure 42:
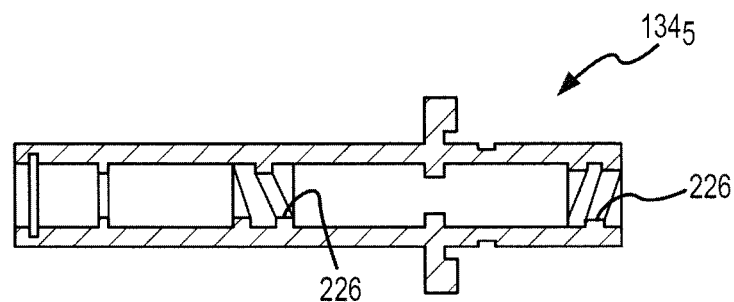
FIG. 42 is a cross-sectional view of the adjusting knob of the catheter handle of FIG. 40, taken substantially along line 42-42 of FIG. 40.
Figure 43:
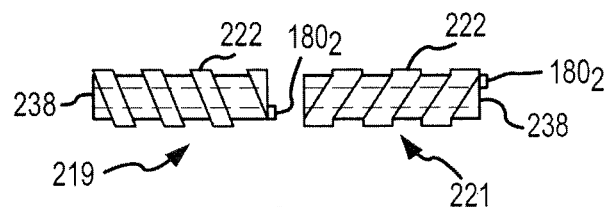
FIG. 43 is a side view of the slides of the catheter handle of FIG. 40.

For a better understanding of the orientation of the threads 222, 226, reference is now made to FIGS. 42 and 43. FIG. 42 is the same longitudinal sectional elevation of the adjusting knob 134$_5$ as it is depicted in FIG. 41, except the adjusting knob 134$_5$ is shown by itself. FIG. 43 is a side elevation of the slides 219, 221.

As shown in FIGS. 42 and 43, in one embodiment, the distal slide 219 has right hand threads 222 that engage right hand threads 226 in the distal portion of the adjusting knob 134$_5$, and the proximal slide 221 has left hand threads 222 that engage left hand threads 226 in the proximal portion of the adjusting knob 134$_5$. Thus, as can be understood from FIGS. 40-43, when the adjusting knob 134$_5$ is rotated relative to the mounting shaft 138$_3$ in a first direction about the longitudinal axis of the handle 118$_5$, the slides 219, 221 will converge along the wire guide 150$_5$, thereby causing the first wire 162 to be placed into tension and the second wire 162 to be compressed. As a result, the distal end 126 of the catheter body 112 will deflect in a first direction. Similarly, when the adjusting knob 134$_5$ is rotated in a second direction that is opposite from the first direction, the slides 219, 221 will diverge along the wire guide 150$_5$, thereby causing the first wire 162 to be compressed and the second wire 162 to be placed into tension. As a result, the distal end 126 of the catheter body 112 will deflect in a second direction generally opposite from the first direction.

Figures 44A, 44B:
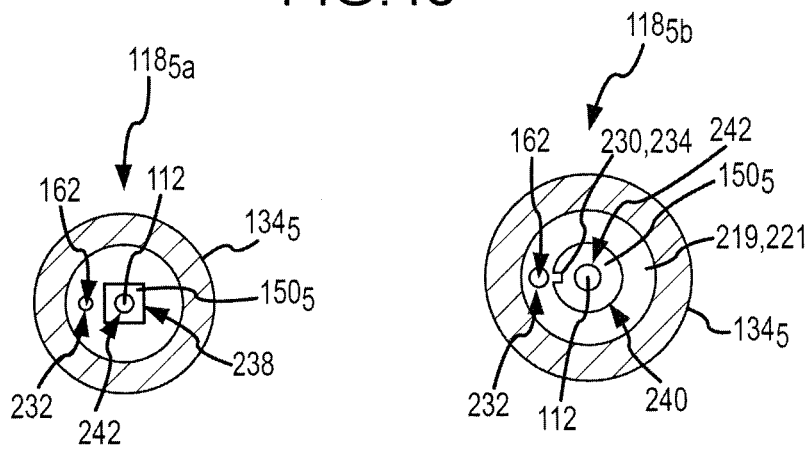
FIGS. 44A and 44B are cross-sectional views of embodiments of a catheter handle similar to the handle of FIG. 41, taken substantially along line 44-44 in FIG. 41.

In one embodiment, to prevent the slides 219, 221 from simply rotating around the wire guide $150_5$ when the adjusting knob $134_5$ is rotated, the slides 219, 221 and wire guide $150_5$ are configured such that the slides 219, 221 will displace along the wire guide $150_5$, but not rotationally around it. For example, as indicated in FIG. 44A, which is a latitudinal sectional elevation of the handle $118_5$ as taken along section line 44A-B-44A-B in FIG. 41, the wire guide $150_5$ has a square cross section that mates with a square hole 238 running the length of the slide 219, 221. The interaction between the square hole 238 and the square cross section of the wire guide $150_5$ prevents a slide 219, 221 from rotating about the wire guide $150_5$, but still allows the slide 219, 221 to displace along the length of the wire guide $150_5$.

Figure 45:
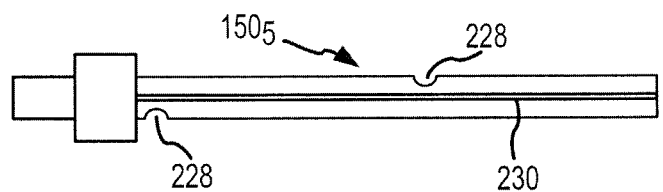
FIG. 45 is a side view of an embodiment of a wire guide equipped with a groove such as may be used in the catheter handle of FIG. 40.

In another embodiment, as shown in FIG. 44B, which is another embodiment of the same latitudinal sectional elevation depicted in FIG. 44A, each slide 219, 221 has a hole 240 with a circular cross section. Each hole 240 runs the length of its respective slide 219, 221 and includes a key 234 that extends into the hole 240 from the interior circumferential surface of the hole 240. The key 234 engages a groove or slot 230 that runs along the length of the wire guide $150_5$ as depicted in FIG. 45, which is a side elevation of one embodiment of the wire guide $150_5$. The interaction between the key 234 and the slot 230 prevents a slide 219, 221 from rotating about the wire guide $150_5$, but still allows the slide 219, 221 to displace along the length of the wire guide $150_5$.

As shown in FIGS. 44A and 44B, a hollow shaft 242 extends through the wire guide $150_5$. This allows a catheter body 112 with a lumen to extend completely through the handle $118_5$ as shown in FIG. 41.

For a detailed discussion of another embodiment of the handle 118 that is similar to the embodiment depicted in FIG. 40, reference is now made to FIGS. 46 and 47. FIG. 46 is a longitudinal sectional elevation of the handle $118_6$ as if taken through section line 46-46 of a handle similar to the handle $118_5$ of FIG. 40. FIG. 47 is a longitudinal sectional plan view of the handle $118_6$ as if taken through section line 47-47 of a handle similar to the handle $118_5$ in FIG. 40 and wherein section line 47-47 forms a plane that is perpendicular to the plane formed by section line 46-46 in FIG. 40.

As illustrated in FIGS. 46 and 47, the handle $118_6$ includes an adjusting knob $134_6$ pivotally coupled to the distal end of the mounting shaft (i.e., base portion) $138_4$. In one embodiment, the adjusting knob $134_6$ includes a proximal end 244, a distal end 246 and a threaded shaft 248, which is connected to the proximal end 244 and extends distally along the longitudinal axis of the adjusting knob $134_6$. The threaded shaft 248 includes a distal end 250, a proximal end 252, a series of right hand threads 254 along a distal portion of the shaft 248, and a series of left hand threads 256 along a proximal portion of the shaft 248.

As shown in FIGS. 46 and 47, a distal slide $219_1$ is located in a distal portion of the adjusting knob $134_6$, and a proximal slide $221_1$ is located in a proximal portion (i.e., a hub portion) of the adjusting knob $134_6$. Each slide has a hole 224 through which the threaded shaft 248 passes. The inner circumferential surface of the hole 224 for the distal slide $219_1$ has right hand threads that mate with the right hand threads 254 on the distal portion of the shaft 248. Similarly, the inner circumferential surface of the hole 224 for the proximal slide $221_1$ has left hand threads that mate with the left hand threads 256 on the proximal portion of the shaft 248. In other embodiments, the locations for the left and right threads are reversed.

As can be understood from FIG. 48, which is an isometric view of one embodiment of the wire guide $150_6$, a hollow center shaft 258 extends from the distal end of the wire guide $150_6$, through the threaded shaft 248 of the adjustment knob $134_6$, and to the proximal end of the base shaft $138_3$. Thus, in one embodiment, a catheter body 112 may be routed through the lumen 242 of the wire guide's hollow center shaft 258 to exit the proximal end of the handle $118_6$, as illustrated in FIGS. 46 and 47.

As illustrated in FIG. 46, each deflection wire 162a, 162b travels along the interior of the wire guide $150_6$ until it exits the wire guide $150_6$ at a hole 228 in the sidewall of the wire guide $150_6$. Each deflection wire 162a, 162b then extends to the slide $219_1$, $221_1$ to which the deflection wire 162a, 162b is attached. In one embodiment, in order to attach to a slide $219_1$, $221_1$, a deflection wire 162a, 162b passes through a passage 232 in the slide $219_1$, $221_1$ and attaches to a hollow tension adjustment screw $180_3$ via a knot $178_2$ as previously described herein.

In one embodiment, as shown in FIG. 46, the deflection wire 162b leading to the proximal slide $221_1$ passes through a second passage 236 in the distal slide $219_1$. The second passage 236 has sufficient clearance that the passage 236 may easily displace along the wire 162b when the distal slide $219_1$ displaces distally and proximally. The second passage 236 serves as a guide that stiffens the wire 162b and helps to reduce the likelihood that the wire 162b will bend when compressed.

As can be understood from FIGS. 46 and 47, when the adjusting knob $134_6$ is rotated relative to the mounting shaft $138_4$ in a first direction about the longitudinal axis of the handle $118_6$, the slides $219_1$, $221_1$ will converge along the threaded shaft 248, thereby causing the first wire 162a to be placed into tension and the second wire 162b to be compressed. As a result, the distal end 126 of the catheter body 112 will deflect in a first direction. Similarly, when the adjusting knob $134_6$ is rotated in a second direction that is opposite from the first direction, the slides $219_1$, $221_1$ will diverge along the threaded shaft 248, thereby causing the first wire 162a to be compressed and the second wire 162b to be placed into tension. As a result, the distal end 126 of the catheter body 112 will deflect in a second direction generally opposite from the first direction.

In one embodiment, to prevent the slides $219_1$, $221_1$ from simply rotating with the threaded shaft 248 within the adjusting knob $134_6$ when the adjusting knob $134_6$ is rotated, the slides $219_1$, $221_1$ and wire guide $150_6$ are configured such that the slides $219_1$, $221_1$ will displace along the threaded shaft 248, but not rotationally within the adjusting knob $134_6$. For example, as indicated in FIGS. 48 and 49, which is a latitudinal sectional elevation of the handle $118_6$ as taken along section line 49-49 in FIG. 46, the wire guide $150_6$ has right and left semicircular portions 260 that oppose each other and extend along the length of the hollow center shaft 258 of the wire guide $150_6$. As shown in FIG. 49, the generally planar opposed faces 262 of the semicircular portions 260 abut against the generally planar side faces 264 of the slides $219_1$, $221_1$. This interaction prevents a slide $219_1$, $221_1$ from rotating within the adjustment knob $134_6$ when the knob $134_6$ is rotated, but still allows the slide $219_1$, $221_1$ to displace along the length of the threaded shaft 248.

In still other embodiments shown in FIGS. 50-62, a multi-directional catheter control handle 266 may be used to maneuver the catheter body's distal end (or distal end portion or distal portion) into a variety of orientations, or to independently maneuver a distal segment and a proximal segment of a catheter shaft. The multi-directional catheter control handle 266 may provide even further maneuverability in comparison to the embodiments discussed with reference to FIGS. 15-49. The multi-directional catheter control handle 266 enhances maneuverability of the catheter body's distal end through the use of a first adjusting knob and a second adjusting knob, as opposed to one adjusting knob.

Although the multi-directional handle 266 will be described in terms of right/left (R/L) and anterior/posterior (A/P) deflection of a single catheter segment, application of the multi-directional handle 266 is not so limited. For example, as noted above, the multi-directional handle 266 may also find use with a catheter shaft with two independently-deflectable segments. Accordingly, it should be understood that the following discussion contemplates a catheter shaft with independently-deflectable segments, and descriptions of separate R/L deflection and A/P deflection also encompasses independent deflection of distal and proximal segments of a catheter shaft.

Figure 50:
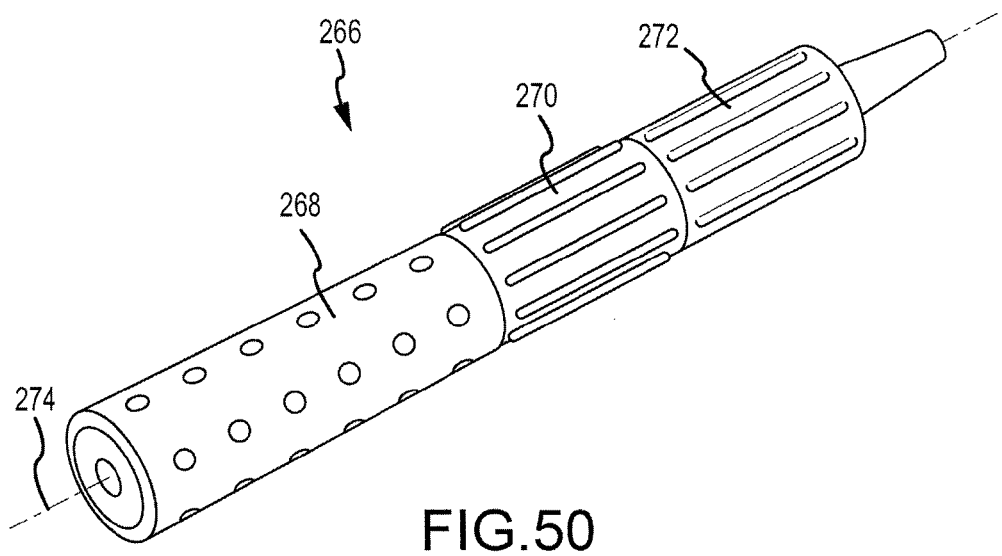
FIG. 50 is an isometric view of an embodiment of a multi-directional catheter control handle.

FIG. 50 shows one embodiment of the multi-directional catheter control handle 266 having a handle grip 268, an R/L adjusting knob 270, an A/P adjusting knob 272, and a longitudinal axis 274. With two adjusting knobs 270, 272, the multi-directional catheter control handle 266 may control at least two pairs of deflection wires that in turn control the orientation of the catheter body's distal end.

Figure 51:
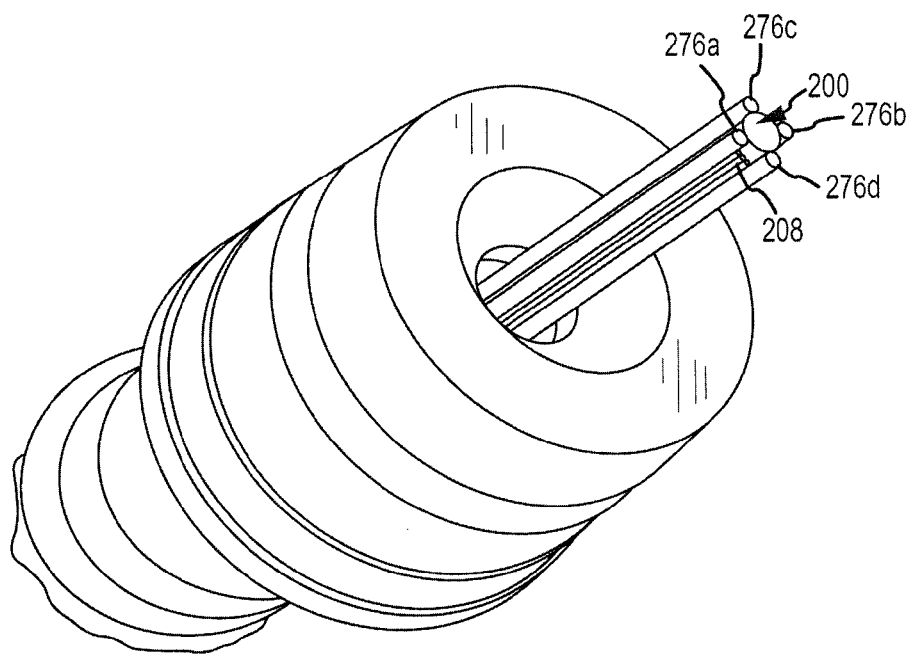
FIG. 51 is an isometric view of a portion of the catheter handle of FIG. 50.

FIG. 51, which has at least one component removed for purposes of clarity, shows how four deflection wires 276a through 276d may be oriented about the lumen 200 adjacent to electrical wires 208. The four deflection wires 276a through 276d may be operably coupled to the adjusting knobs 270, 272 and to the catheter body's distal end or to distal and proximal segments of the catheter body. In one embodiment, for example, the R/L adjusting knob 270 may control the movement of deflection wires 276a and 276b, and the A/P adjusting knob 272 may control the movement of deflection wires 276c and 276d. Rotating the R/L adjusting knob 270 thus deflects the distal end in right and left directions. Similarly, rotating the A/P adjusting knob 272 deflects the distal end in anterior and posterior directions. Movement of the distal end is discussed in more detail below. However, in addition to deflection in four "cardinal" directions (i.e., right, left, anterior, and posterior), one skilled in the art will recognize that rotating the adjusting knobs 270, 272 in combination or in sequence may orient the distal end at oblique angles in relation to the deflection wires 276 and/or in relation to the rest of the flexible elongate member. Accordingly, the maneuverability of the catheter's distal end is enhanced.

The four deflection wires 276a through 276d may also be coupled to proximal and distal segments of the catheter shaft such as, for example only, one of the embodiments illustrated in FIGS. 1-14. For example, in an embodiment, the deflection wires 276a and 276b may be coupled to a proximal segment of the catheter shaft, and deflection wires 276c and 276d may be coupled to the distal segment of the catheter shaft. In such an embodiment, the A/P adjusting knob 272 may act as a distal segment adjusting knob (i.e., a distal segment manual actuation mechanism) and the R/L adjusting knob 270 may act as a proximal segment adjusting knob (i.e., a proximal segment manual actuation mechanism). The deflection wires 276a through 276d may extend through the catheter shaft as shown in any of FIGS. 1-14, or in some other manner known in the art.

Figure 52:
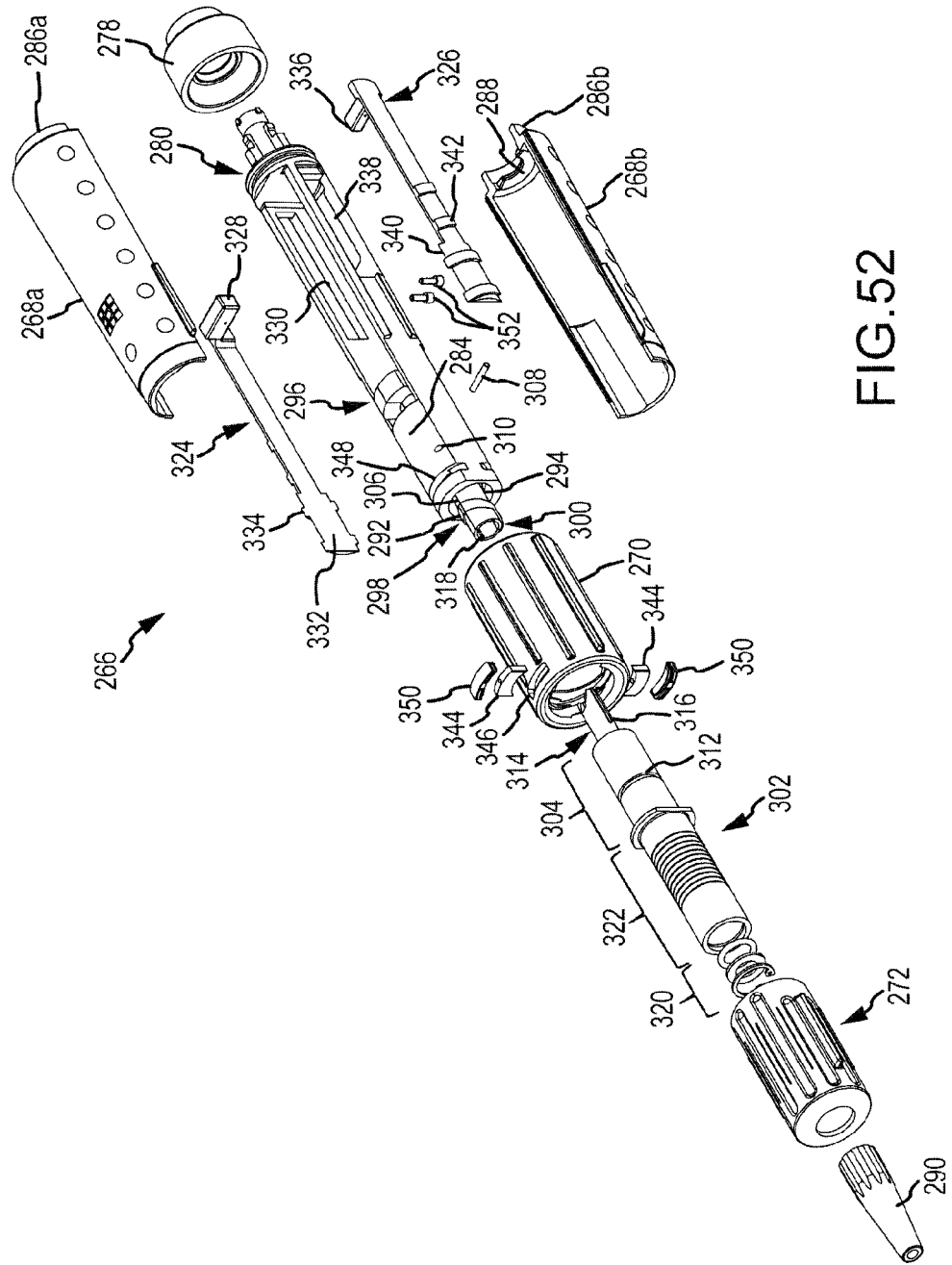
FIG. 52 is an exploded view of the catheter handle of FIG. 50.

The components of one embodiment of the multi-directional catheter control handle 266 that provide for enhanced maneuverability are shown in an exploded view in FIG. 52. These components can be categorized into three non-mutually exclusive groups: a first group of components that help achieve both R/L catheter deflection and A/P catheter deflection, a second group that is used primarily to achieve A/P catheter deflection, and a third group that is used primarily to achieve R/L catheter deflection. These groups merely facilitate discussion of the multi-directional catheter control handle 266 and by no means limit the functions, purposes, benefits, or the like of any given component. Also, particularly where users integrate R/L deflection and A/P deflection, components from all of these groups are used to deflect the catheter body's distal end.

The handle grip 268 is one such common component that is useful during both R/L and A/P deflection. The handle grip 268 is shown in two subparts 268a, 268b and is located near the proximal end of the multi-directional catheter control handle 266. Forming the handle grip 268 from two subparts 268a, 268b allows for quick access to internal components, if needed. An end cap 278 and a clip feature 280 may help retain the handle grip subparts 268a, 268b around a mounting shaft 284 that acts as a support member for a number of components of the handle 266. The end cap 278 may secure generally peripheral rims 286a, 286b extending from subparts 268a, 268b, respectively. The clip feature 280 may be configured to mate with an internal rim 288 on subparts 268a, 268b to further secure the handle grip 268 around the mounting shaft 284.

In addition, a nozzle-like projection 290 may be helpful during both R/L and A/P deflection. The nozzle-like projection 290 may provide strain relief for the flexible tubular body of a catheter that extends from the projection 290. Moreover, the nozzle-like projection 290 may have internal threads that mate with threads on a wire guide, as discussed below.

FIG. 52 also shows components of the multi-directional catheter control handle 266 that allow for A/P deflection of the catheter body's distal end. In particular, the handle 266 may include a first slide 292 and a second slide 294, which may resemble those slides shown in FIG. 18. The slides 292, 294 may be mirror images of each other and may include proximal portions 296 and distal portions 298. Deflection wires may operably attach to the proximal portions 296 of the first and second slides 292, 294. For example, a pair of deflection wires 276c, 276d of FIG. 51 may operably attach to the proximal portions 296 of the first and second slides 292, 294. Hence translation of the first and second slides 292, 294 may control the pair of deflection wires 276c, 276d and ultimately the catheter body's distal end, or a proximal segment or distal segment of the catheter body.

The deflection wires may be operably attached to the proximal portions 296 through a number of techniques including, for example, using a retention screw or soldering. In some embodiments, for example, the proximal portions 296 of the first and second slides 292, 294 may have holes through which the deflection wires may slidably extend. With regard to a single deflection wire, for example, a segment of the deflection wire that protrudes proximally beyond one of the proximal portions 296 may be attached to a mass of solder that cannot pass through a hole in the proximal portion 296. Translating the proximal portion 296 of a slide proximally from a "neutral position," as described further below, may translate the mass of solder and the attached deflection wire proximally. But when the proximal portion 296 is translated distally from the neutral position, the slidably attached deflection wire and the mass of solder may remain largely stationary. In these embodiments, rotation of the corresponding adjusting knob alters the tension in only one of the pair of deflection wires at a time. Some amount of slack in one of a pair of deflection wires can be advantageous where the distal end of the catheter is maneuvered into a variety of orientations using both the R/L adjusting knob 270 and the A/P adjusting knob 272.

Moreover, the distal portion 298 of the first slide 292 may contain right-handed square threads, while the distal portion 298 of the second slide 294 may contain left-handed square threads. By configuring the slides 292, 294 with square threads, the slides 292, 294 do not, or at least are less likely to, revert after displacement. Square threads have a self-locking property that makes them less susceptible to thread slippage or back-out. Similar to the slides shown in FIG. 29, the slides 292, 294 may be hollowed so as to form a passage 300 for various wires of the catheter including, for example, the lumen and deflection wires 276. And further, the slides 292, 294 may be positioned within the mounting shaft 284 such that they may translate, but are prevented from rotating due to the contours of their proximal portions 296 and the mounting shaft 284.

To translate the first and second slides 292, 294, an adjusting knob insert 302 with square internal threading may be provided. The adjusting knob insert 302 may be rotatably coupled to the mounting shaft 284 by inserting a hub portion 304 of the insert 302 into a distal opening 306 of the mounting shaft 284. A dowel pin 308 may be inserted into an angular pinhole 310 to secure a groove 312 on the hub portion 304. Once rotatably coupled, the adjusting knob insert 302 may rotate about the longitudinal axis 274, but is prevented from translating along the length of the mounting shaft 284. The adjusting knob insert 302 may have right-handed and left-handed internal threads similar to those shown in FIG. 28, except that the threads in the insert 302 may be square threads. Thus, the distal portions 298 of the first and second slides 292, 294 may be inserted within the adjusting knob insert 302, with the internal threads of the insert 302 engaging with the external threads, or parts thereof, of the slides 292, 294.

When the adjusting knob insert 302 rotates one way, the first slide 292 may translate in a direction opposite the second slide 294. When the adjusting knob insert 302 rotates the other way, each slide 292, 294 may translate, respectively, in a reverse direction. This back and forth translation of the slides 292, 294 is one aspect of the catheter handle 266 that allows for A/P deflection.

Still referring to FIG. 52, the multi-directional catheter control handle 266 may also include a wire guide 314 positioned within the adjusting knob insert 302 and the passage 300 formed by the first and second slides 292, 294. To prevent the wire guide 314 from rotating when the adjusting knob insert 302 rotates, the wire guide 314 may have projections 316 that can be inserted within slots 318 within the first and second slides 292, 294. Because the first and second slides 292, 294 do not rotate relative to the mounting shaft 284, neither does the wire guide 314 once the projections 316 are inserted within the slots 318. Further, at least one washer and a retaining ring 320 may hold a distal end (not shown) of the wire guide 314 in place within the adjusting knob insert 302. The distal end of the wire guide 314 may be threaded to allow for engagement with internal threads disposed in the nozzle-like projection 290. Yet further, the A/P adjusting knob 272 may be press-fitted onto a distal portion 322 of the adjusting knob insert 302. The A/P adjusting knob 272 may provide a more effective contact surface for a user of the handle 266 as opposed to the adjusting knob insert 302 itself In an alternative embodiment, the A/P adjusting knob 272 may be integral with the distal portion 322 of the adjusting knob insert 302 such that the A/P adjusting knob 272 need not be press-fitted onto the distal portion 322. In either case, internal threads may be said to be disposed within the A/P adjusting knob 272.

In addition, FIG. 52 shows components of the multi-directional catheter control handle 266 that allow for R/L deflection of the catheter body's distal end. In particular, a right slide 324 and a left slide 326 may be provided. The right slide 324 may include a proximal tab 328 that extends through a slot 330 in the mounting shaft 284 when a flat portion 332 of the right slide 324 is positioned against the mounting shaft 284. Once positioned, the right slide 324 and the proximal tab 328 may translate along a portion of the length of the mounting shaft 284. The right slide 324 may further include a set of right-hand square threads 334 for engagement with internal threads (not shown) of the R/L adjusting knob 270. Similar to the square threads on the first and second slides 292, 294, the square threads 334 on the right slide 324 prevent, or at least reduce the likelihood of, thread slippage or back-out.

Similar to the right slide 324, the left slide 326 may also include a proximal tab 336 that extends through a slot 338 in the mounting shaft 284 when a flat portion 340 of the left slide 326 is positioned against the mounting shaft 284. Once positioned, the left slide 326 and the proximal tab 336 may also translate proximally and distally in relation to the mounting shaft 284. When both right and left slides 324, 326 are positioned against the mounting shaft 284, the proximal tab 336 of the left slide 326 may sit below the proximal tab 328 of the right slide 324. Similarly, the left slide 326 may also include a set of left-hand square threads 342 for engagement with internal threads of the R/L adjusting knob 270. Hence the R/L adjusting knob 270 may have right-handed and left-handed internal threads similar to those shown in FIG. 28, except that the threads in the R/L adjusting knob 270 may be square threads. Rotating the R/L adjusting knob 270 about the longitudinal axis 274 may cause the right and left slides 324, 326 to translate in opposite directions along the length of the handle 266.

The proximal tabs 328, 336 may provide points of attachment for deflection wires, such as the pair of deflection wires 276a, 276b shown in FIG. 51, for example. Just like the first and second slides 292, 294, deflection wires may be attached to the proximal tabs 328, 336 through a number of techniques including, for example, using a retention screw or soldering. Hence when the R/L adjusting knob 270 translates the right and left slides 324, 326 in opposite directions, a tensile force on at least one of the two attached deflection wires—different than those controlled by the A/P adjusting knob 272—is either increased or decreased.

It should be noted that although the terms "first," "second," "right," "left," "R/L," and "A/P" are used herein, such terms are merely for the benefit of this detailed description. Hence the first and second slides could be referred to as a first pair of slide members, for example, and the right and left slides could be referred to as a second pair of slide members. Likewise, the same can be said for the adjusting knobs, deflection wires, and so on. Moreover, some embodiments of the multi-directional catheter control handle may operate without two pairs of slide members. Rather, two slide members may be used. By way of example, a first slide member may be operably coupled to a first pair of deflection wires and to one adjusting knob, while a second slide member may be operably coupled to a second pair of deflection wires and to another adjusting knob. One exemplary way a single slide member could control a pair of deflection wires is to attach the deflection wires to opposite sides of the slide member. Attaching the slide member at a point between the opposite sides to a pivot would allow for converse movement of the attached deflection wires.

Once the right and left slides 324, 326 are positioned alongside the mounting shaft 284, the R/L adjusting knob 270 may be rotatably coupled to the mounting shaft 284. In one embodiment, the R/L adjusting knob 270 may be assembled around the right and left slides 324, 326 and the mounting shaft 284. The internal threads of the R/L adjusting knob 270 may engage or partially engage the right-hand and left-hand square threads 334, 342. To keep the R/L adjusting knob 270 from translating along the mounting shaft 284, stop blocks 344 may be inserted through apertures 346 in the R/L adjusting knob 270 and openings 348 in the mounting shaft 284. As such, the stop blocks 344 may ride along the surface of the hub portion 304 of the adjusting knob insert 302. More specifically, the stop blocks 344 may be positioned in a ring groove (not shown) disposed within the R/L adjusting knob 270 such that the R/L adjusting knob 270 may rotate about the mounting shaft 284, but is prevented from translating along the length of the mounting shaft 284. In other words, the stop blocks 344 may extend away from the hub portion 304 and into a ring groove within the R/L adjusting knob 270, but the stop blocks 344 do not occupy the apertures 346 of the R/L adjusting knob 270. To cover the apertures 346 and prevent contaminants from entering the handle 266, caps 350 may be placed over the apertures 346.

In one embodiment, the multi-directional catheter control handle 266 may also include at least one deflection stop pin 352, which may extend fully or partially within the mounting shaft 284. Deflection stop pins 352 may be positioned between the proximal portions 296 of the first and second slides 292, 294 and the proximal tabs 328, 336 of the right and left slides 324, 326. The deflection stop pins 352 may prevent the slides 292, 294, 324, 326 from being over-displaced so as to strain, stretch, deform, break, or otherwise damage one of the deflection wires. Accordingly, when at least one of the slides 292, 294, 324, 326 contacts the deflection stop pins 352, one or both of the pairs of deflection wires may be fully deflected and thus the adjusting knobs 272, 270 may not be rotated further in that direction. In another embodiment, the stop pins 352 may limit the movement of only the first and second slides 292, 294.

Referring now to FIG. 53, components of one embodiment of the multi-directional catheter control handle 266 are shown in a state of sub-assembly. Namely, the mounting shaft 284, the first and second slides 292, 294, and the adjusting knob insert 302 are shown to be partially assembled. The hub portion 304 of the adjusting knob insert 302 may extend through the distal opening 306 of the mounting shaft 284. The dowel pin 308, however, has not yet been inserted. The distal portion 298 of the second slide 294 has been fully inserted within the adjusting knob insert 302, with the proximal portion 296 of the second slide 294 protruding. With the second slide 294 fully inserted into the adjusting knob insert 302, the first slide 292 may be inserted into the adjusting knob insert 302. As the adjusting knob insert 302 is rotated within the mounting shaft 284, the second slide 294 is backed out of the adjusting knob insert 302 and the first slide 292 is drawn into the adjusting knob insert 302. The slides 292, 294 translate in opposite directions due to the right-hand square threads on the first slide 292, the left-hand square threads on the second slide 294, and the right- and left-hand internal threading within the adjusting knob insert 302.

The second slide 294 may be backed out of the adjusting knob insert until it is generally even with the first slide 292, as shown in FIG. 54. The first and second slides 292, 294 come to a neutral position where they are equally inserted within the adjusting knob insert 302. This position is neutral because from this point each slide 292, 294 can move an equal distance proximal to or distal from the adjusting knob insert 302. This means that each slide 292, 294 can cause an attached deflection wire to deflect the catheter body's distal end to the same degree, albeit in opposing directions.

FIG. 54 shows one embodiment of the mounting shaft 284 in a state of sub-assembly similar to that of FIG. 53. In FIG. 54, though, the right and left slides 324, 326 are shown alongside the mounting shaft 284. Further, the proximal tabs 328, 336 of the right and left slides 324, 326 are shown extending through the slots 330, 338 in the mounting shaft 284. The right slide 324 is shown to be offset from the left slide 326 because the R/L adjusting knob 270 may be assembled around the right and left slides 324, 326 much like the adjusting knob insert 302 is assembled around the first and second slides 292, 294.

Figure 55:
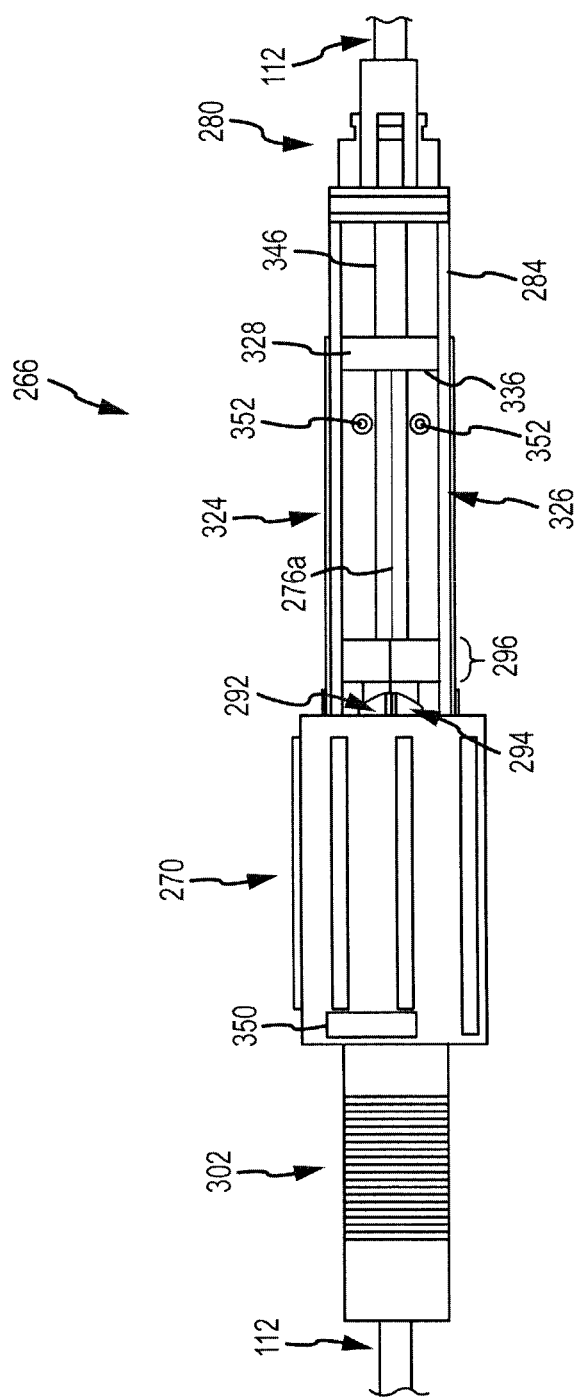

As can be understood from FIG. 55, the R/L adjusting knob 270 may be positioned around the mounting shaft 284. To secure the R/L adjusting knob 270, the stop blocks may be inserted through the apertures in the R/L adjusting knob 270 and openings in the mounting shaft 284. Once the caps 350 are placed over the apertures, the right and left slides 324, 326 may be positioned within the R/L adjusting knob 270. Like the first and second slides 292, 294, the right and left slides 324, 326 may also be brought to a neutral position. There, each slide 324, 326 may extend generally equally within the R/L adjusting knob 270, and one proximal tab 328 may be positioned over the other proximal tab 336, as shown in FIG. 55.

FIG. 55 also illustrates the catheter body 112 extending through the length of a partially-assembled multi-directional catheter control handle 266. This portion of the catheter body 112 that may extend through, or generally couple to, the multi-directional catheter control handle 266 or the mounting shaft 284 can be referred to as the proximal end of the catheter body 112. Specifically, the proximal end of the catheter body 112 may extend through the clip feature 280, between the proximal tabs 328, 336, through the gap 300 formed by the first and second slides 292, 294, and through the adjusting knob insert 302. As discussed with reference to the embodiments shown in FIGS. 15-49, the proximal end of the catheter body 112 may have various openings or discontinuities to allow deflection wires into the catheter body 112. The deflection wire 276a, which may be attached to the proximal tab 328, may extend along the outside of the proximal end of the catheter body 112 and into the passage 300 formed by the first and second slides 292, 294. The deflection wire 276a and other deflection wires (not shown) may enter the proximal end at one or more discontinuities in the catheter body 112, as described above.

Figure 56:
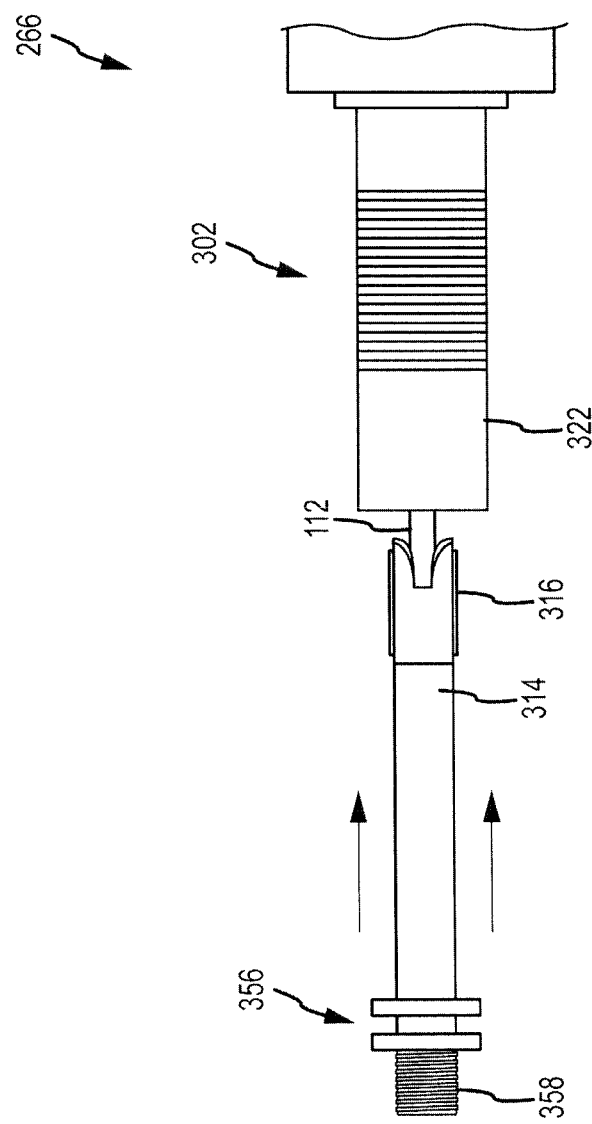
FIG. 56 is a top view of an embodiment of a multi-directional catheter control handle in a state of sub-assembly where a wire guide is being located within an adjusting knob insert.

Now referring to FIG. 56, the wire guide 314 may be positioned around the catheter body 112, with the end of the wire guide 314 having the projections 316 being placed into the distal portion 322 of the adjusting knob insert 302. The wire guide 314 may slide into the adjusting knob insert 302 such that the projections 316 slide into the slots in the first and second slides. Ultimately, the distal end 356 of the wire guide 314 may be positioned within the distal portion 322 of the adjusting knob insert 302. To secure the distal end 356, the at least one washer and retaining ring (not shown) may be used to maintain the distal end 356 within the distal portion 322 of the adjusting knob insert 302. In a final assembly, threads 358 of the distal end 356 may engage with internal threads on the nozzle-like projection to further retain the components of the handle 266.

Figure 57:
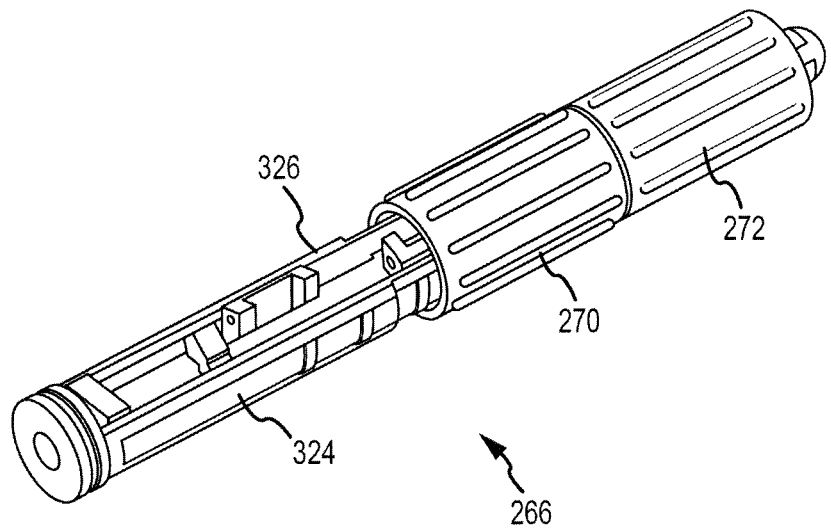
FIG. 57 is an isometric view of an embodiment of a multi-directional catheter control handle with a grip removed.
Figure 58:
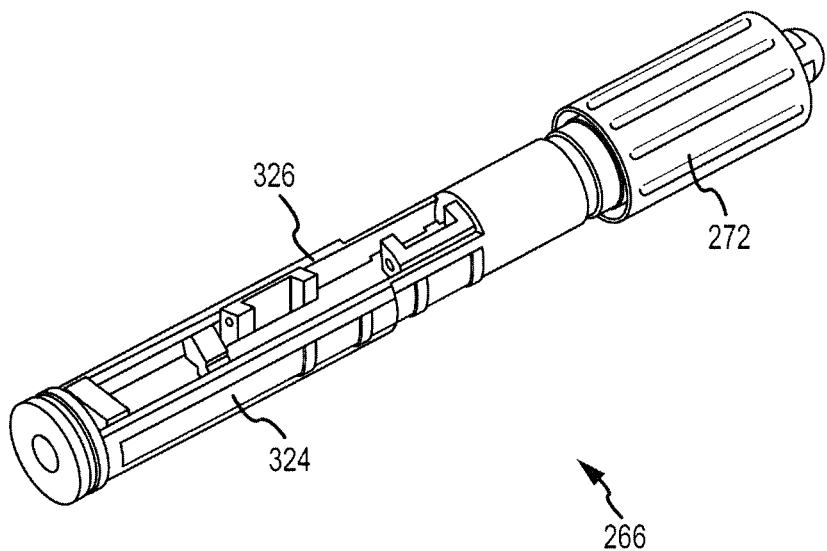
FIG. 58 is an isometric view of an embodiment of a multi-directional catheter control handle with a grip and an adjusting knob removed.

FIG. 57 shows one embodiment of the multi-directional catheter control handle 266 in which the handle grip is removed for purposes of clarity. Moreover, the embodiment shown in FIG. 57 utilizes many of the components that were discussed with reference to FIGS. 37-39. By contrast, however, the embodiment shown here includes two adjusting knobs 270, 272 and the right and left slides, 324, 326. This embodiment exemplifies how some of the embodiments discussed with reference to FIGS. 15-49, or at least the components contained therein, may be adapted for use with the multi-directional catheter control handle 266. Moreover, FIG. 58 shows the same embodiment as that in FIG. 57, except that the handle grip and the R/L adjusting knob are removed for an additional perspective.

Although the multi-directional catheter control handle is described herein for use with a catheter body, such a handle could be used in conjunction with any medical device or flexible elongate member, even in applications beyond the medical field. Moreover, the multi-directional catheter control handle may be compatible with virtually all of the embodiments discussed with reference to FIGS. 15-49. For example, electrodes may be disposed along the catheter body or along the distal portion of the catheter body for delivering therapy, performing ablative procedures, mapping internal organs, and the like.

With reference to FIGS. 59A-59E and corresponding FIGS. 60A-60E, the catheter body's distal end 126 is shown in a variety of orientations that are caused by the multi-directional catheter control handle. FIGS. 59A-59E show side views of the distal end 126, while FIGS. 60A-60E show corresponding top views of the distal end 126. FIGS. 59A, 60A show the distal end 126 in a straight, undeflected position 390. Here, although not shown, both the first and second slides and the right and left slides may be in neutral positions. As a user rotates the R/L adjusting knob, the right and left slides translate in opposite directions, with one of the slides pulling a deflection wire (e.g., deflection wire 276a in FIG. 51) away from the distal end 126. The result of this tension in the deflection wire is shown in FIGS. 59B, 60B, with the distal end 126 deflected to the right 392. From there, the user may rotate the A/P adjusting knob to cause the first and second slides to translate in opposite directions. Similarly, one of the first or second slides may pull a deflection wire (e.g., deflection wire 276c in FIG. 51) away from the distal end 126. FIGS. 59C, 60C show the result of this sequence, with the distal end 126 deflected in a posterior direction 394. To progress to a deflection 396 shown in FIGS. 59D, 60D, the user may deflect the R/L adjusting knob in a direction opposite that which was used to initially deflect the distal end 126. As such, the right and left slides may respectively translate in directions opposite those taken to arrive at the orientation shown in FIGS. 59B, 60B. With the distal end 126 now deflected to the left 396, the user may rotate the A/P adjusting knob in a different direction to arrive at an anterior deflection 398 shown in FIGS. 59E, 60E.

Without reiterating the full sequence taken to achieve the various deflections shown in FIGS. 59A-5E, 60A-60E, similar steps may be taken to achieve the deflections shown in FIGS. 61A-61E, 62A-62E. FIGS. 61A-61E show side views of the distal end 126, while FIGS. 62A-62E show corresponding top views of the distal end 126. FIGS. 61A, 62A show the distal end 126 in the straight, undeflected position 390. The primary difference between FIGS. 59B-59E, 60B-60E and FIGS. 61B-61E, 62B-62E is that the distal end 126 shown in FIGS. 61B-61E, 62B-62E is deflected further than the distal end 126 shown in FIGS. 59B-59E, 60B-60E. Instead of approximately 90 degree states of deflection, the distal end 126 is shown to be in approximately 180 states of deflection. Thus, FIGS. 61B, 62B show the distal end 126 in a rightward deflection 400; FIGS. 61C, 62C show an anterior deflection 402; FIGS. 61D, 62D show a leftward deflection 404; and FIGS. 61E, 62E show a posterior deflection 406.

Although the adjusting knobs 270, 272 may need to be rotated further to deflect the distal end 126 to 180 degrees, a similar sequence of rotations of the adjusting knobs 270, 272 may be used to achieve each deflection.

One skilled in the art will understand that the distal end 126 is capable of deflection at all different angles under the control of the multi-directional catheter control handle. For example, the distal end 126 may be held at a position between FIG. 59D and FIG. 61E, or the distal end 126 may be deflected less than 90 degrees or greater than 180 degrees. Thus FIGS. 59-62 show merely exemplary embodiments of the distal end 126.

Furthermore, one skilled in the art will understand that a multi-directional catheter control handle may be combined with different catheter shaft configurations and constructions to create catheters with various numbers and configurations of deflectable segments. For example, a multi-directional catheter control handle may be combined with an embodiment of a catheter shaft, such as one of the embodiments shown in FIGS. 6-12, and may be used to effect the shaft deflections shown in FIGS. 6-9.

One skilled in the art will also understand how deflecting the distal end (or distal portion) of the catheter may be accomplished with structures other than those described and depicted above. For example, if push/pull deflection wires (sometimes referred to as tension/compression wires) are employed, a first and second pair of deflection wires may not be necessary. Rather, a first deflection wire and a second deflection wire could be positioned 90 degrees apart about the lumen, similar to two (e.g., 276a, 276d) of the four generally orthogonal-configured pairs of wires shown in FIG. 51. Since each push/pull deflection wire can carry tensile and compressive loads, there is no need to pair each deflection wire with an additional, opposing deflection wire.

In still another embodiment, the multi-directional catheter control handle could function without adjusting knobs. Instead, the slide members could have protrusions that extend from the mounting shaft. A user could use the protrusions to translate, or axially displace, the slides within the mounting shaft. In yet another embodiment, the multi-directional handle could use adjusting knobs that rotate at the surface of the mounting shaft or handle grip. For example, one adjusting knob operatively connected (e.g., through a gear system) to one pair of slides could be placed on the top of the handle such that it does not rotate about a longitudinal axis of the handle. Another adjusting knob operatively connected to another pair of slides could be placed on the side of the handle. Thus, the two adjusting knobs could be positioned at 90 degrees from one another. Moreover, the adjusting knob on the top of the handle could control R/L deflection while the adjusting knob on the side of the handle could control A/P deflection. This configuration could enhance the intuitiveness of the handle, as rotating the top adjusting knob clockwise and counterclockwise would deflect the distal portion of the catheter right and left, and rotating the side adjusting knob forward and backward would deflect the distal portion of the catheter posterior and anterior. Each of the above-described adjusting knobs and protrusions are encompassed in the term "manual actuation mechanism," though a manual actuation mechanism is not limited to such knobs and protrusions.

Even further, the present disclosure contemplates an embodiment where the degree of rotation of the adjusting knobs can be made to be substantially similar to the degree of deflection in the distal portion of the catheter. For example, rotating a R/L adjusting knob 90 degrees to the right may cause the distal portion of the catheter to deflect about 90 degrees to the right. This characteristic may be accomplished by using proper thread angles, gear ratios, or the like.

The aforementioned catheter handles may operate with a variety of catheter systems such as visualization systems, mapping systems, and navigation support and positioning systems (i.e., for determining a position and orientation (P&O) of a flexible elongate member or other medical device). For example, the catheter handles may be used with an ENSITE™ VELOCITY™ system running a version of NAVX™ software commercially available from St. Jude Medical, Inc., of St. Paul, Minn. and as also seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present disclosure, and hereby incorporated by reference in its entirety. These exemplary systems with which the catheter handles may be utilized can comprise conventional apparatus known generally in the art, for example, the ENSITE™ VELOCITY™ system described above or other known technologies for locating/navigating a catheter in space (and for visualization), including for example, the CARTO™ visualization and location system of Biosense Webster, Inc., (e.g., as exemplified by U.S. Pat. No. 6,690,963 entitled "System for Determining the Location and Orientation of an Invasive Medical Instrument" hereby incorporated by reference in its entirety), the AURORA™ system of Northern Digital Inc., a magnetic field based localization system such as the GMPS™ system based on technology from MediGuide Ltd. of Haifa, Israel and now owned by St. Jude Medical, Inc. (e.g., as exemplified by U.S. Pat. Nos. 7,386,339, 7,197,354 and 6,233,476, all of which are hereby incorporated by reference in their entireties) or a hybrid magnetic field-impedance based system, such as the CARTO 3 visualization and location system of Biosense Webster, Inc. (e.g., as exemplified by U.S. Pat. No. 7,848,789, which is hereby incorporated by reference in its entirety). Some of the localization, navigation and/or visualization systems can involve providing a sensor for producing signals indicative of catheter location and/or distal portion orientation information, and can include, for example one or more electrodes in the case of an impedance-based localization system such as the ENSITE™ VELOCITY™ system running NAVX™ software, which electrodes can already exist in some instances, or alternatively, one or more coils (i.e., wire windings) configured to detect one or more characteristics of a low-strength magnetic field, for example, in the case of a magnetic-field based localization system such as the GMPS™ system using technology from MediGuide Ltd. described above.

Although a number of embodiments of this invention have been described above with a certain degree of particularity, those skilled in the art could make numerous alterations to the disclosed embodiments without departing from the spirit or scope of this invention. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An elongate medical device comprising:
a shaft comprising a distal segment and proximal segment and defining a longitudinal axis;
at least one proximal segment deflection wire adapted to deflect said proximal segment;
at least one distal segment deflection wire adapted to deflect said distal segment independent of said proximal segment; and
a handle portion comprising a first manual actuation mechanism coupled to said at least one distal segment deflection wire and a second manual actuation mechanism coupled to said at least one proximal segment deflection wire;
wherein actuation of said first manual actuation mechanism imparts a tensile force on said distal segment deflection wire thereby causing said distal segment to deflect and actuation of said second manual actuation mechanism imparts a tensile force on said proximal segment thereby causing said proximal segment to deflect;
further wherein at least one of said first manual actuation mechanism and said second manual actuation mechanism comprises an adjusting knob configured to impart a tensile force on the deflection wire with which it is coupled by rotating about the longitudinal axis of said shaft.

2. The elongate medical device of claim 1, wherein said first manual actuation mechanism comprises a first adjusting knob configured to impart a tensile force on said first deflection wire by rotating about the longitudinal axis of said shaft and said second manual actuation mechanism comprises a second adjusting knob configured to impart a tensile force on said second deflection wire by rotating about the longitudinal axis of said shaft.

3. The elongate medical device of claim 1, wherein said at least one distal segment deflection wire comprises two distal segment deflection wires.

4. The elongate medical device of claim 3, wherein actuation of said first manual actuation mechanism in a first actuation direction imparts a tensile force on a first of said two distal segment deflection wires, thereby causing said distal segment to deflect in a first deflection direction, further wherein actuation of said first manual actuation mechanism in a second actuation direction imparts a tensile force on a second of said two distal segment deflection wires, thereby causing said distal segment to deflect in a second deflection direction.

5. The elongate medical device of claim 4, wherein said first deflection direction is substantially opposed to said second deflection direction.

6. The elongate medical device of claim 1, wherein said at least one proximal segment deflection wire comprises two proximal segment deflection wires.

7. The elongate medical device of claim 6, wherein actuation of said second manual actuation mechanism in a first actuation direction imparts a tensile force on a first of said two proximal segment deflection wires, thereby causing said proximal segment to deflect in a first deflection direction, further wherein actuation of said second manual actuation mechanism in a second actuation direction imparts a tensile force on a second of said two proximal segment deflection wires, thereby causing said proximal segment to deflect in a second deflection direction.

8. The elongate medical device of claim 7, wherein said first deflection direction is substantially opposed to said second deflection direction.

9. An elongate medical device comprising:
a shaft comprising a unitary wall comprising a distal segment and a proximal segment;
a distal segment steering mechanism embedded in said wall distal segment;
a proximal segment steering mechanism embedded in said wall proximal segment;
a distal segment deflection member, coupled to said distal segment steering mechanism, configured to deflect said distal segment independent of said proximal segment, said distal segment deflection member having a distal end coupled with said shaft distal segment and a proximal end;
a proximal segment deflection member, coupled to said proximal segment steering mechanism, configured to deflect said proximal segment, said proximal segment deflection member having a distal end coupled with said shaft proximal segment and a proximal end; and
a handle, coupled to said proximal segment deflection member proximal end and said distal segment deflection member proximal end, and configured to control the deflection of said shaft proximal segment and said shaft distal segment.

10. The elongate medical device of claim 9, said proximal segment deflection member extends through said wall.

11. The elongate medical device of claim 9, wherein said shaft proximal segment defines a lumen and said distal segment deflection member extends through said lumen.

12. The elongate medical device of claim 9, wherein at least one of said distal segment steering mechanism and said proximal segment steering mechanism comprises a pull ring.

13. The elongate medical device of claim 12, wherein said distal segment steering mechanism comprises a distal pull ring and said proximal segment steering mechanism comprises a proximal pull ring.

* * * * *